US010595840B2

(12) United States Patent
Bippart et al.

(10) Patent No.: US 10,595,840 B2
(45) Date of Patent: Mar. 24, 2020

(54) WOUND CLOSURE APPARATUS AND METHOD

(71) Applicant: Surgical Innovations LLC, Marysville, CA (US)

(72) Inventors: Peter E. Bippart, Oroville, CA (US); Diane S. Kindred, Yuba City, CA (US)

(73) Assignee: Surgical Innovations LLC, Marysville, CA (US)

( * ) Notice: Subject to any disclaimer, the term of this patent is extended or adjusted under 35 U.S.C. 154(b) by 0 days.

(21) Appl. No.: 16/541,391

(22) Filed: Aug. 15, 2019

(65) Prior Publication Data

US 2019/0365365 A1 Dec. 5, 2019

Related U.S. Application Data

(60) Continuation-in-part of application No. 16/286,507, filed on Feb. 26, 2019, now Pat. No. 10,441,259.
(Continued)

(51) Int. Cl.
| | | |
|---|---|---|
| *A61B 17/00* | (2006.01) | |
| *A61B 90/00* | (2016.01) | |
| *A61B 1/07* | (2006.01) | |

(52) U.S. Cl.
CPC ............ *A61B 17/0057* (2013.01); *A61B 1/07* (2013.01); *A61B 2017/00004* (2013.01);
(Continued)

(58) Field of Classification Search
CPC ...... A61B 17/0057; A61B 2017/00004; A61B 2017/00526; A61B 2017/00871;
(Continued)

(56) References Cited

U.S. PATENT DOCUMENTS

| 2,324,520 A | 7/1943 | Lamson |
| 3,447,533 A | 6/1969 | Spicer |

(Continued)

FOREIGN PATENT DOCUMENTS

| WO | WO-2004/024030 A1 | 3/2004 |
| WO | WO-2005/011352 A2 | 2/2005 |

OTHER PUBLICATIONS

Anonymous. (Aug. 2, 2013). "Increasing Demand for Minimally Invasive Surgeries Drives Growth in the Endoscopy Systems Market, According to New Report by Global Industry Analysts, Inc." Endoscopy Systems: A Global Strategic Business Report. Global Industry Analysts, Inc. San Jose, CA. (PRWEB) WEB www.prweb.com, two pages, date viewed: Feb. 14, 2014.
(Continued)

*Primary Examiner* — Phong Son H Dang
(74) *Attorney, Agent, or Firm* — Morrison & Foerster LLP

(57) ABSTRACT

A wound closure apparatus can be a self-contained device for delivery and deployment of a wound plug. The apparatus can include a post and a wound plug. The post can have a top end, a bottom end, and an interior channel located between the top end and the bottom end. The bottom end of the post can include a plurality of perforations extending from the interior channel to an outer surface of the post. The wound plug can include a body and a bladder, the bladder disposed around the body. In an assembled configuration of the wound closure apparatus, the bottom end of the post is positioned through an opening of the bladder such that the bladder can receive a fluid through the interior channel and the plurality of perforations.

14 Claims, 43 Drawing Sheets

Related U.S. Application Data which is a continuation-in-part of application No. 16/275,222, filed on Feb. 13, 2019, now abandoned, which is a continuation-in-part of application No. 15/449,818, filed on Mar. 3, 2017, now Pat. No. 10,219,797, which is a division of application No. 14/634,421, filed on Feb. 27, 2015, now Pat. No. 9,615,817.

(52) U.S. Cl.
CPC ............ *A61B 2017/00115* (2013.01); *A61B 2017/00526* (2013.01); *A61B 2017/00606* (2013.01); *A61B 2017/00623* (2013.01); *A61B 2017/00871* (2013.01); *A61B 2017/00884* (2013.01); *A61B 2017/00889* (2013.01); *A61B 2090/037* (2016.02)

(58) Field of Classification Search
CPC .... A61B 2090/037; A61B 2017/00115; A61B 2017/00606; A61B 2017/00884; A61B 2017/00623
See application file for complete search history.

(56) References Cited

U.S. PATENT DOCUMENTS

| | | | |
|---|---|---|---|
| 4,007,743 A * | 2/1977 | Blake | A61B 17/0057 606/232 |
| 4,532,926 A * | 8/1985 | O'Holla | A61B 17/0643 606/220 |
| 4,935,028 A | 6/1990 | Drews | |
| 5,192,301 A | 3/1993 | Kamiya et al. | |
| 5,342,393 A * | 8/1994 | Stack | A61B 17/0057 24/453 |
| 5,350,399 A * | 9/1994 | Erlebacher | A61B 17/0057 128/899 |
| 5,366,460 A | 11/1994 | Eberbach | |
| RE34,866 E | 2/1995 | Kensey et al. | |
| 5,419,765 A * | 5/1995 | Weldon | A61B 17/0057 604/507 |
| 5,620,461 A | 4/1997 | Muijs Van De Moer et al. | |
| 5,725,552 A * | 3/1998 | Kotula | A61B 17/0057 604/285 |
| 5,853,422 A | 12/1998 | Huebsch et al. | |
| 5,879,366 A | 3/1999 | Shaw et al. | |
| 5,976,174 A * | 11/1999 | Ruiz | A61B 17/0057 606/151 |
| 6,120,539 A | 9/2000 | Eldridge et al. | |
| 6,241,768 B1 | 6/2001 | Agarwal et al. | |
| 7,798,953 B1 * | 9/2010 | Wilk | A61B 17/0057 600/16 |
| 7,842,069 B2 * | 11/2010 | Widomski | A61B 17/0057 606/213 |
| 8,398,676 B2 | 3/2013 | Roorda et al. | |
| 8,506,593 B2 * | 8/2013 | Klein | A61B 17/0057 606/213 |
| 8,657,852 B2 | 2/2014 | Roorda et al. | |
| 8,821,529 B2 * | 9/2014 | Kariniemi | A61B 17/0057 606/200 |
| 8,992,567 B1 * | 3/2015 | Houser | A61B 17/08 606/213 |
| 9,089,311 B2 | 7/2015 | Fortson et al. | |
| 9,241,696 B2 | 1/2016 | Mehl | |
| 9,295,456 B2 * | 3/2016 | Subramanian | A61B 17/0057 |
| 9,615,817 B2 | 4/2017 | Bippart et al. | |
| 10,219,797 B2 | 3/2019 | Bippart et al. | |
| 10,238,518 B2 * | 3/2019 | Annunziata | A61F 5/0079 |
| 10,441,259 B2 | 10/2019 | Bippart | |
| 2002/0042622 A1 * | 4/2002 | Vargas | A61B 17/11 606/153 |
| 2005/0273135 A1 * | 12/2005 | Chanduszko | A61B 17/0057 606/213 |
| 2006/0015142 A1 * | 1/2006 | Malazgirt | A61B 17/0057 606/213 |
| 2006/0167494 A1 * | 7/2006 | Suddaby | A61B 17/0057 606/213 |
| 2006/0190036 A1 * | 8/2006 | Wendel | A61B 17/0057 606/213 |
| 2006/0206146 A1 * | 9/2006 | Tenerz | A61B 17/0057 606/213 |
| 2007/0073337 A1 * | 3/2007 | Abbott | A61B 17/0057 606/213 |
| 2007/0123817 A1 | 5/2007 | Khosravi et al. | |
| 2007/0135831 A1 * | 6/2007 | Burnett | A61B 5/14539 606/192 |
| 2007/0179527 A1 * | 8/2007 | Eskuri | A61B 17/0057 606/213 |
| 2007/0185529 A1 * | 8/2007 | Coleman | A61B 17/0057 606/213 |
| 2007/0276415 A1 * | 11/2007 | Kladakis | A61B 17/0057 606/151 |
| 2008/0208226 A1 * | 8/2008 | Seibold | A61B 17/0057 606/158 |
| 2008/0215089 A1 | 9/2008 | Williams et al. | |
| 2009/0043314 A1 * | 2/2009 | Sevensson | A61B 17/3417 606/108 |
| 2009/0088795 A1 * | 4/2009 | Cahill | A61B 17/0057 606/215 |
| 2009/0312789 A1 * | 12/2009 | Kassab | A61B 17/0057 606/213 |
| 2010/0016885 A1 | 1/2010 | Eidenschink et al. | |
| 2010/0114156 A1 | 5/2010 | Mehl | |
| 2010/0114159 A1 * | 5/2010 | Roorda | A61B 17/0057 606/215 |
| 2010/0179590 A1 * | 7/2010 | Fortson | A61B 17/0057 606/216 |
| 2010/0185233 A1 * | 7/2010 | Thommen | A61B 17/0057 606/213 |
| 2011/0077683 A1 * | 3/2011 | Huss | A61B 17/0057 606/213 |
| 2011/0082495 A1 * | 4/2011 | Ruiz | A61B 17/0057 606/213 |
| 2011/0184439 A1 * | 7/2011 | Anderson | A61B 17/0057 606/151 |
| 2012/0078295 A1 * | 3/2012 | Steiner | A61B 17/0057 606/213 |
| 2013/0012987 A1 | 1/2013 | Klein | |
| 2013/0165963 A1 * | 6/2013 | Coleman | A61B 17/12022 606/192 |
| 2014/0200597 A1 * | 7/2014 | Klein | A61B 17/0057 606/142 |
| 2015/0231374 A1 * | 8/2015 | Kassab | A61M 25/1011 604/101.01 |

OTHER PUBLICATIONS

Cell. Incorporated, Matristem ®, Acell Inc., located at: www.ACell.com, two pages.
Chinese Search Report dated Aug. 10, 2018, for CN Patent Application 201580079181.4, four pages with English translation.
CONNEKT, LLC. (Dec. 11, 2017). "A Revolutionary Patented Surgical Apparatus Designed by CONNEKT, LLC," YouTube, located at: https://www.youtube.com/watch?v=deZLLd8j8Gk&feature=youtu.be, last visited on Feb. 13, 2019, one page.
Delancey, J. O. M.D., et al. "Operations on the Abdominal Wall." Glob.libr.women's med., (ISSN:1756-2228) 2008; WEB. www.glowm.com (DOI 10.3843/GLOWM.10038), 20 pages, date viewed: Oct. 12, 2013.
Dhandayuthapani, B., et al. (Jul. 9, 2011)."Polymeric Scaffolds in Tissue Engineering Application: A Review," International Journal of Polymer Science: vol. 2011, Article ID 290602, Hindawi Publishing Corp. WEB (Locate by DOI No. 10.1155/2011/290602), 20 pages, date viewed: Feb. 14, 2014.
Extended European Search Report dated Oct. 25, 2018, for EP Application No. 15883638.7, six pages.
Gamal EM, et al., (1997). "Late Epigastric Incisional following Laparoscopic Cholecystectomy." Acta Chir Hung. 36 (1-4) 1997.

(56) References Cited

OTHER PUBLICATIONS pp. 95-96. PubMed-NCBI US National Library of Medicine National Institutes of Health (NCBI) WEB www.PubMed.gov<http://www.PubMed.gov>, two pages, date viewed: Mar. 10, 2014.

Hamood, A. M., et al. (Sep.-Dec. 2009). "Different Port Closure Techniques in Laparoscopy Surgery, World Journal of Laparoscopic Surgery," vol. 2 (3), p. 29-38; (Total 60 pages) International Scientific Journals from Jaypee (Jaypee Brothers Medical Publishers (P) Ltd. WEB www.jaypeejournals.com (DOI No. for PDF is DOI 10.5005/jp-journals-10007-1003), ten pages, date viewed: date Feb. 13, 2014.

Horst, M., et al. "A Bilayered Hybrid MicroFibrous PLGA-Acellular Matrix Scaffold for Hollow Organ Tissue Engineering," Biomateriais, 34 (5). 2013. pp. 1537-1545. Posted at the Zurich Open Repository and Archive, Un. of Zurich WEB www.ScienceDirect.com (DOI 10.5167/uzh-70363), 21 pages, date viewed: Mar. 13, 2014.

Hussain, A. et al. (Jul.-Sep. 2009 ). "Long Term Study of Port-Site Incisional Hernia after Laparoscopic Procedures," Journal of the Society of Laparoendoscopic Surgeons 13 (3), pp. 346-349, the Publisher Society of Laparoendoscopic Surgeons, Inc., PMC-US National Library of Medicine National Institutes of Health, WEB www.PubMed.gov.<http://www.PubMed.gov>, five pages, date viewed Mar. 1, 2014.

Hutmacher, D. et al, (2000). "Scaffolds in Tissue Engineering Bone and Cartilage," Laboratory for Biomedical Engineering, Institute of Engineering Science, Department of Orthopedic Surgery, National University of Singapore, Singapore, Elsevier Science Ltd, 2529-2543, WEB <http://158.110.32.35/download/CURCIO/Hurtmacher-BIO-2000.pdf>, 15 pages, date viewed: Nov. 2013.

International Search Report dated May 13, 2016, for PCT application No. PCT/US2015/067489, five pages. (1.40).

Lawrence, B.J. (Jul. 2006). "Composite Scaffolds of Natural and Synthetic Polymers for Bladder Tissue Engineering," Documentation submitted to the Faculty of the Graduate College of the Oklahoma State Un. for the Degree of Master of Science, , Stillwater, Ok. WEB www.digital.library.okstate.ed <http://www.digital.library.okstate.ed>, 63 pages, date viewed: Mar. 3, 2014.

Nezhat, C.H. et al. (Mar. 3, 2011). "Adhesions Prevention and Management," Prevention and Management of Laparoendoscopic Surgical Complications: Society of Laparoendoscopic Surgeons-Focus Clarity Innovation. 3rd Edition, WEB: www.laparoscopy.blogs.com <http://www.laparoscopy.blogs.com>, 16 pages, date viewed: Nov. 12, 2013.

Non-Final Office Action dated Jun. 20, 2019, for U.S. Appl. No. 16/286,507, filed Feb. 26, 2019, eleven pages.

Notice of Allowance dated Feb. 22, 2017, for U.S. Appl. No. 14/634,421, filed Feb. 27, 2015, ten pages.

Notice of Allowance dated Oct. 23, 2018, for U.S. Appl. No. 15/449,818, filed Mar. 3, 2017, eight pages.

Notice of Allowance (corrected) dated Dec. 5, 2018, for U.S. Appl. No. 15/449,818, filed Mar. 3, 2017, four pages.

Petro, C. et al. (2010). "Repair of Ventral Abdominal Wall Hernias," Chapter 27, Gastrointestinal Tract and Abdomen—Section 05, ACS Surgery: Principles and Practice, Decker Intellectual Properties Inc., Scientific American Surgery, <http://www.sciamsurgery.com/sciamsurgery/institutional/regGetFile.action?fileName=part05_ch21.pdf>, 30 pages, date viewed: Feb. 20, 2014.

Seamon, L.G., et al. (2008)/ "Robotic Trocar Site Small Bowel Evisceration after Gynecologic Cancer Surgery," Journal of Obstetrics and Gynecology 112.2 Part 2, pp. 462-464, The American Obstetricians and Gynecologists. <http://journals.lww.com/greenjournal/Abstract/2008/08001/Robotic_Trocar_Site_Small_B>, abstract, one page, date viewed: Feb. 11, 2014.

Tonouchi, H., et al. (Nov. 1, 2004). "Trocar Site Hernia." JAMA Surgery 139 (11), American Medical Association, pp. 1248-1256. JAMA Networks, www.jamanetwork.com <http://www.jamanetwork.com>, (DOI: 10.1001/arch.surg.139.11.1248 JAMA Networks WEB), nine pages, date viewed: Oct. 12, 2013.

Viju, S. (Jun. 2008). "Biodegradable Polyesters for Medical Applications." The Indian Textile Journal, vol. 118, Issue 9, p. 75: Features/Nonwoven and Technical Textiles., (ISSN 0019-6436), www.indiantextilejournal.com <http://www.indiantextilejournal.com>, two pages, date viewed: Feb. 20, 2014.

Wikipedia. Search: 'Electrospinning,' and 'Extracellular matrix', www.Wikipedia.org <http://www.Wikipedia.org>, 15 pages.

Yamamoto, M., et al. (Jan.-Mar. 2011). "Laparoscopic 5mm Trocar Site Herniation and Literature Review," Journal of the Society of Laparoendoscopic Surgeons, pp. 122-126, US National Library of Medicine National Institutes of Health (NCBI), www.PubMed.gov<http://www.PubMed.gov/>, five pages, date viewed: Feb. 13, 2014.

Notice of Allowance dated Aug. 27, 2019, for U.S. Appl. No. 16/286,507, filed Feb. 26, 2019, seven pages.

* cited by examiner

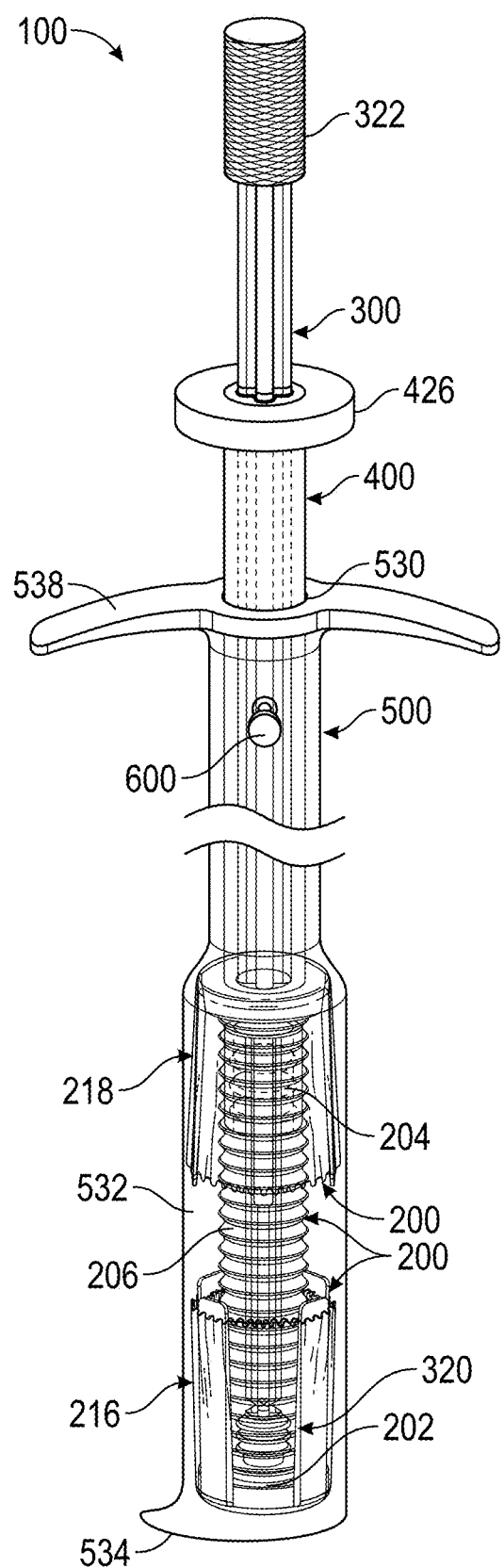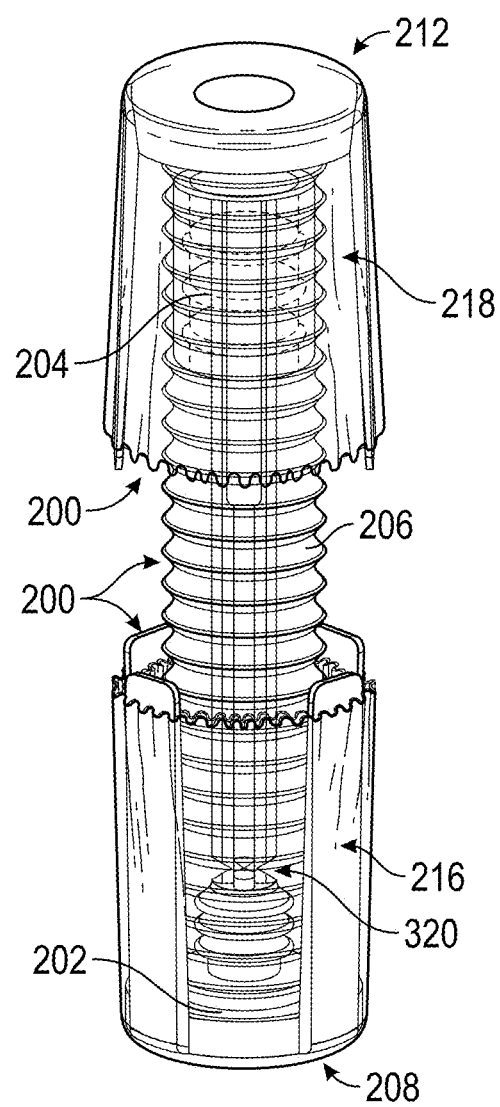
FIG. 1A     FIG. 1B

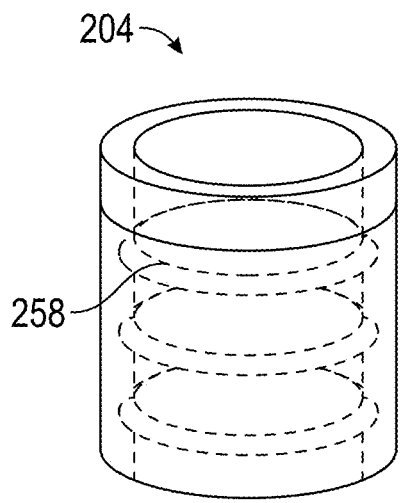
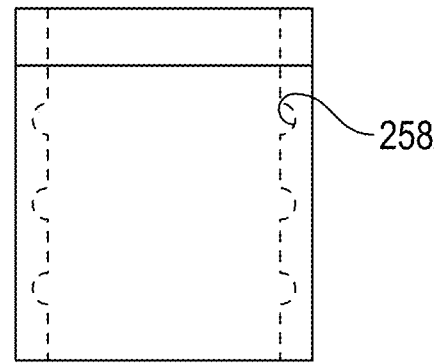
FIG. 2A          FIG. 2B
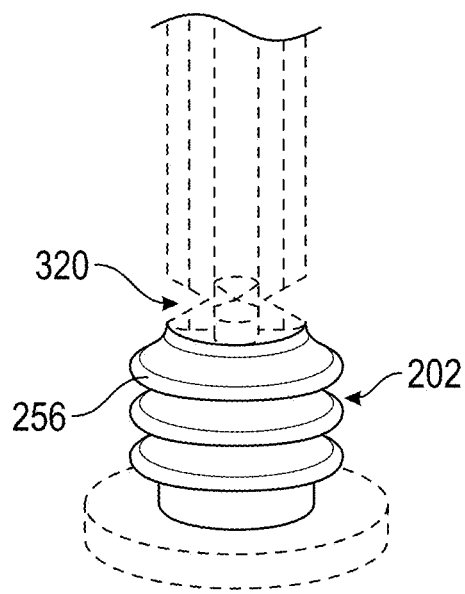
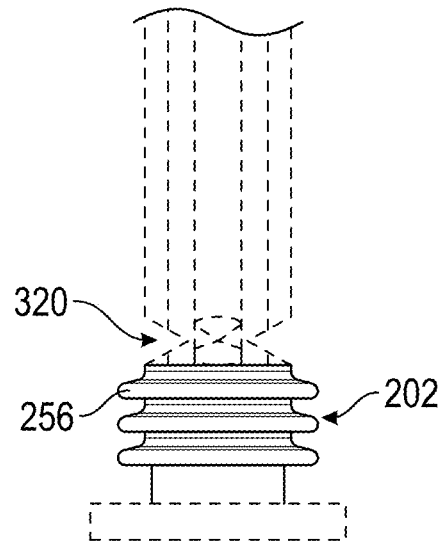
FIG. 2C          FIG. 2D

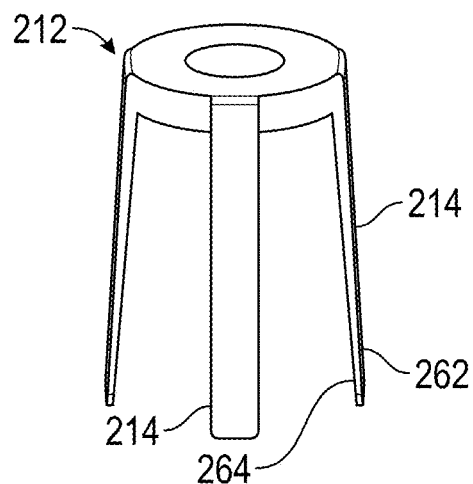
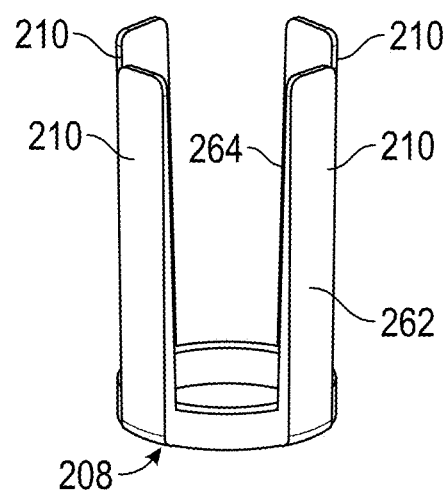
FIG. 2E
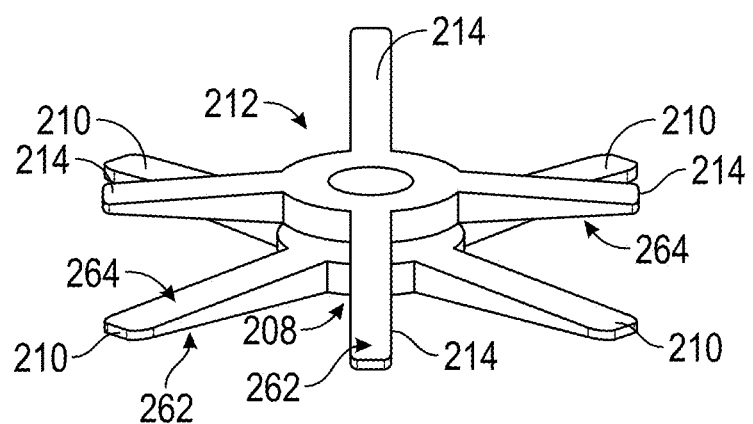
FIG. 2F

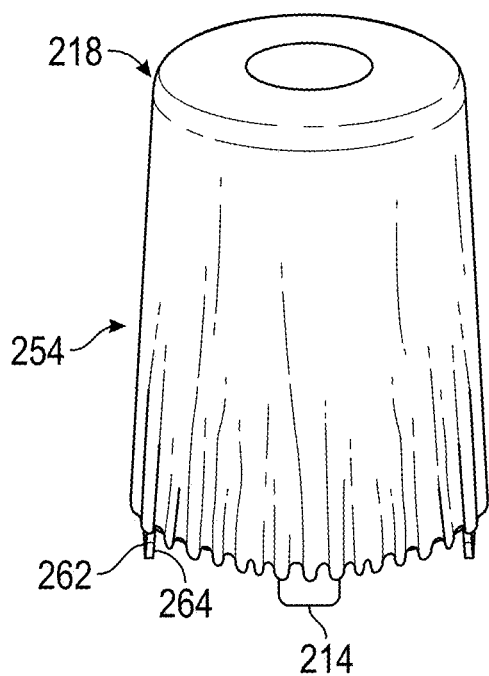
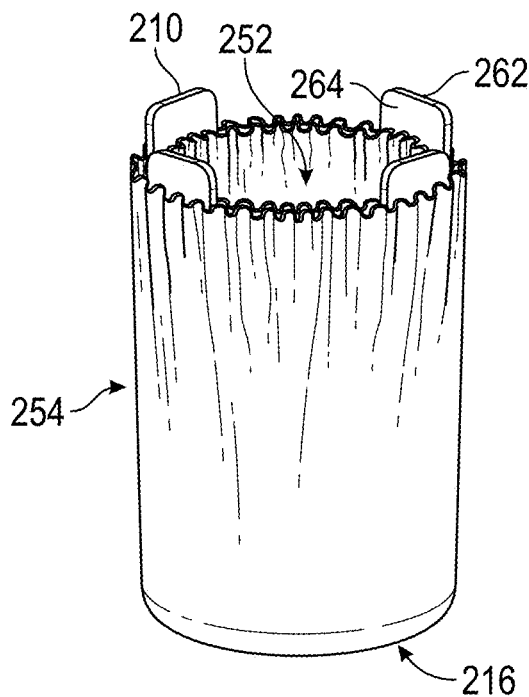
FIG. 2G  FIG. 2H
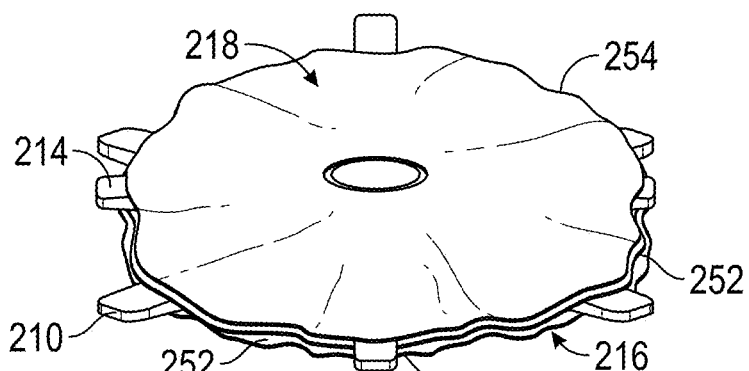
FIG. 2I
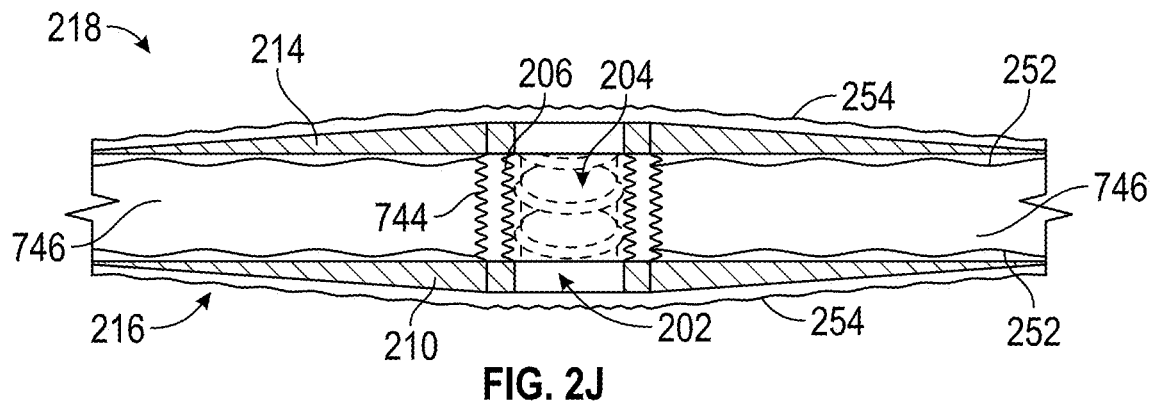
FIG. 2J

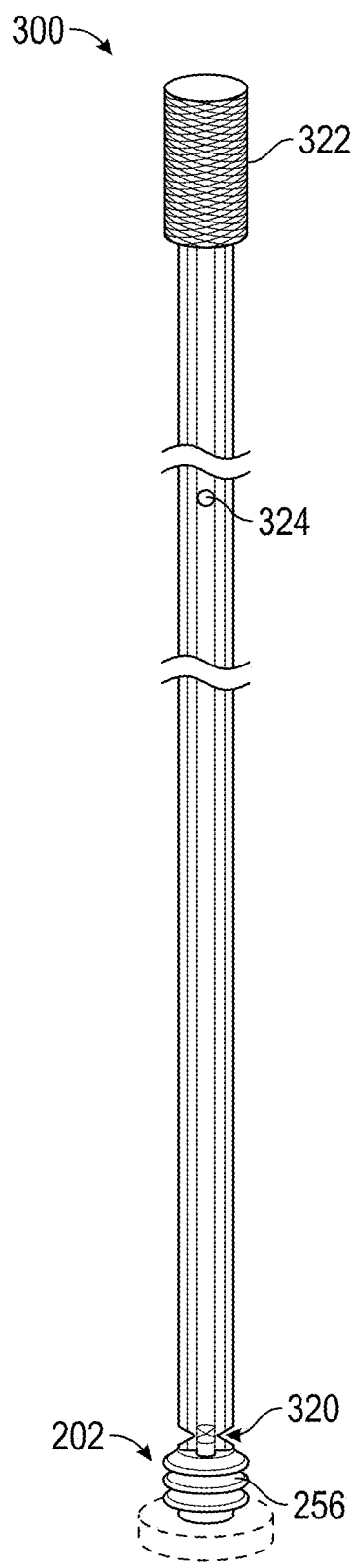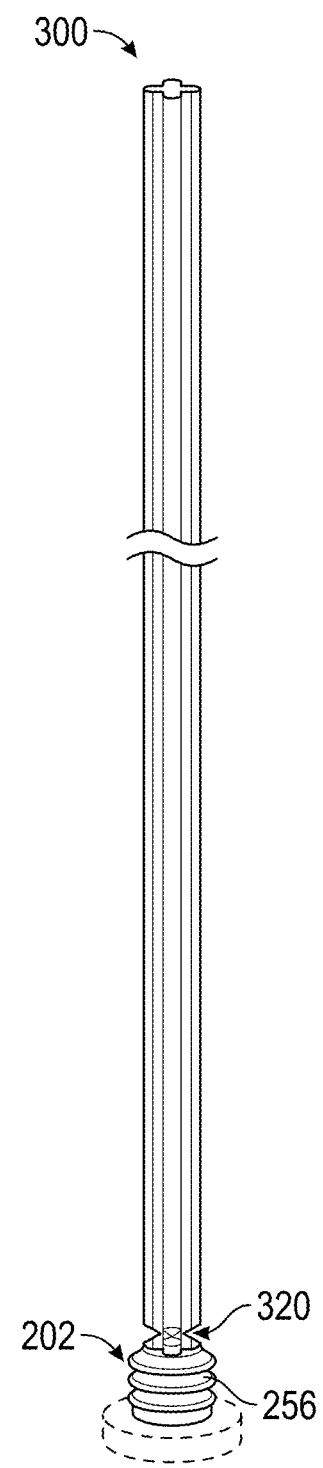
FIG. 3A
FIG. 3B

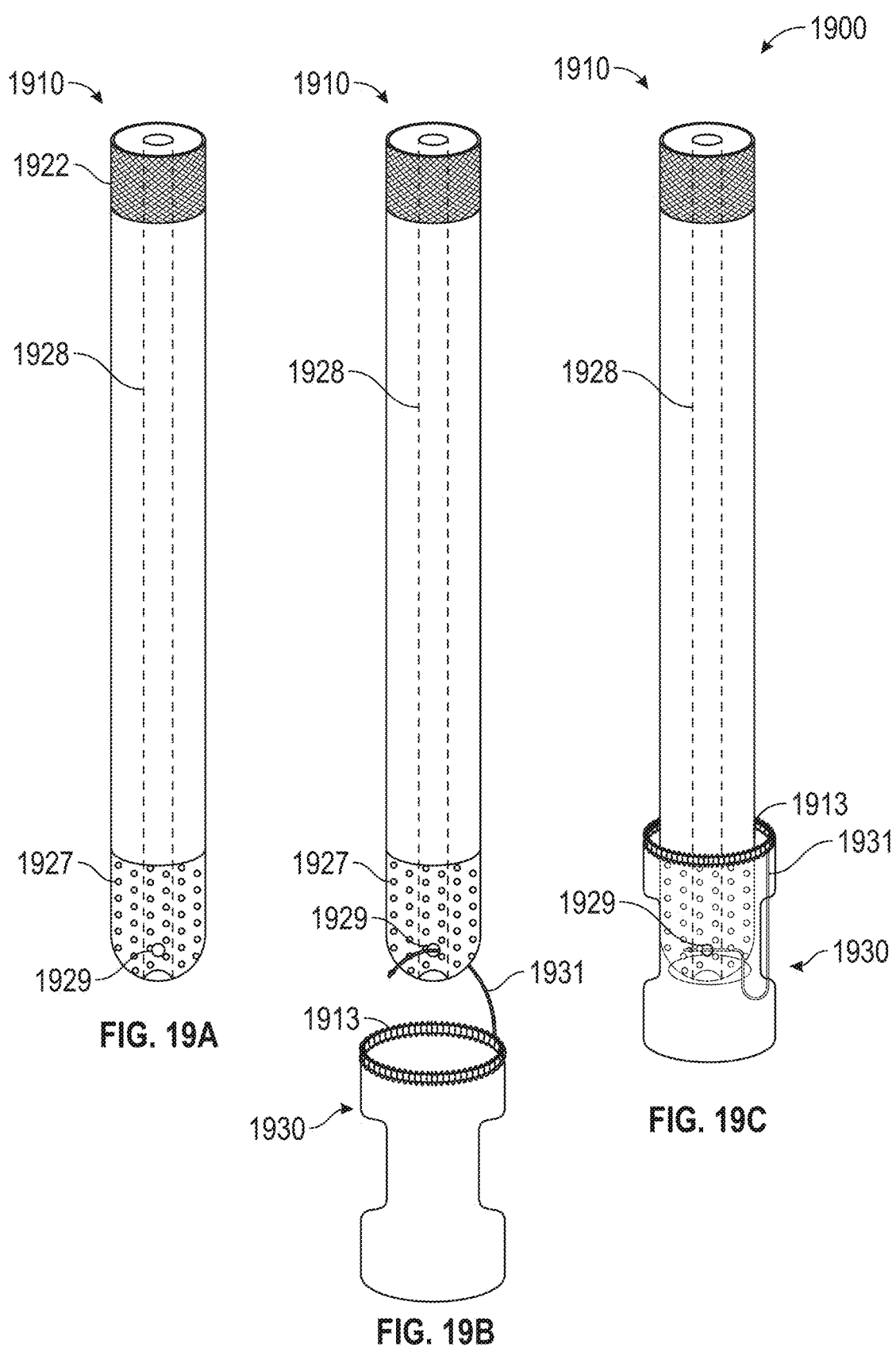

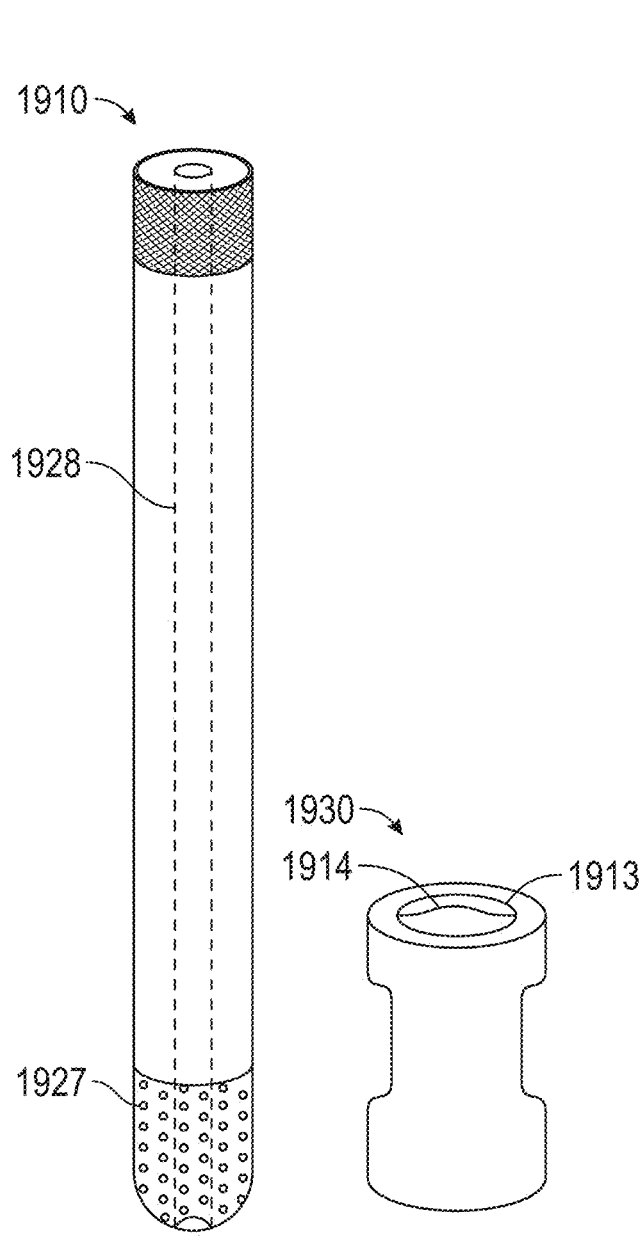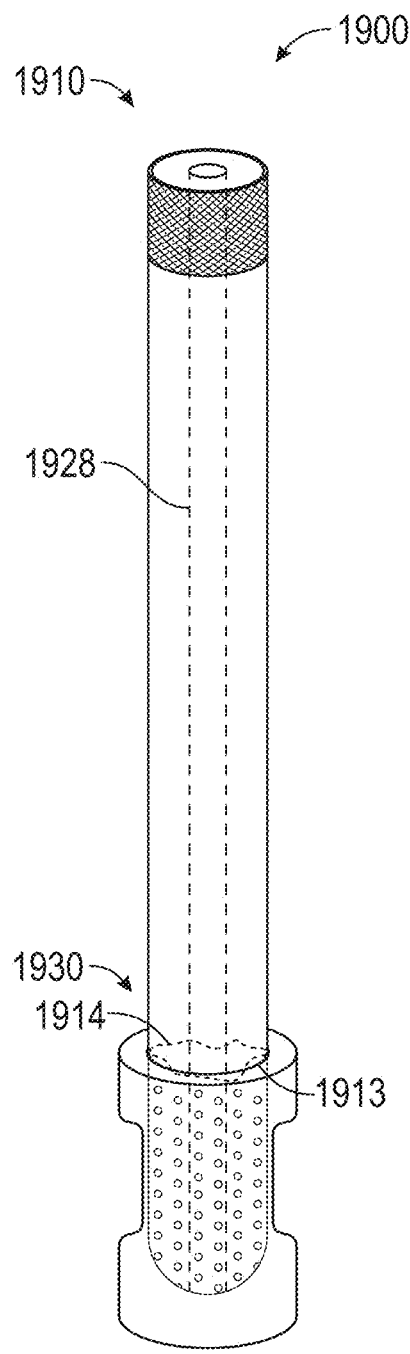
FIG. 19D
FIG. 19E

WOUND CLOSURE APPARATUS AND METHOD

CROSS-REFERENCE TO RELATED APPLICATION

This application is a Continuation in part of U.S. patent application Ser. No. 16/286,507; filed Feb. 26, 2019, which is a Continuation-in-Part of U.S. patent application Ser. No. 16/275,222, filed Feb. 13, 2019; which is a Continuation-in-Part of U.S. patent application Ser. No. 15/449,818, filed Mar. 3, 2017 and issued on Mar. 5, 2019 as U.S. Pat. No. 10,219,797; which is a Divisional Application of U.S. patent application Ser. No. 14/634,421, filed Feb. 27, 2015 and issued on Apr. 11, 2017 as U.S. Pat. No. 9,615,817, the contents of which are incorporated herein by reference in their entirety for all purposes.

FIELD OF THE DISCLOSURE

The present disclosure relates generally to a wound closure apparatus and method.

BACKGROUND OF THE DISCLOSURE

Minimally invasive surgery (MIS), also referred to as laparoscopic or endoscopic surgery, has experienced spectacular growth worldwide over the past few decades for the diagnosis and treatment of a variety of acute and chronic pathologies. Endoscopic procedures are economical, safer, and promote a more rapid recovery in contrast to conventional surgical approaches. Technological advancements in MIS are expected to have robust growth in the future. As endoscopic technologies develop and become the standard of care for most types of surgical interventions, the continued development of innovative quality tools to address the unique problems associated with this type of surgery must be vigorously pursued.

A laparoscopic surgery is performed by inserting a cannula (a hollow plastic or metal tube) through the abdominal wall, either by scalpel dissection or by blunt penetration with a piercing instrument (a trocar) occupying the central lumen of the cannula. When the cannula is placed through the skin and into the abdomen, the surgical blade or central trocar is withdrawn, leaving a cannula that is designed to inflate the abdominal cavity with carbon dioxide gas in order to distend the anterior abdominal wall away from the internal organs. The presence of this gas in the abdominal cavity is known as a pneumoperitoneum.

Once the pneumoperitoneum is established, a fiber optic endoscope (which may either be attached to a high-definition video camera or guided by direct vision) is inserted safely into the abdomen allowing visualization of the abdominal viscera. When complete visualization of the abdomen is accomplished, a number of secondary cannulae are placed via the previously described technique. The surgery is then performed through these cannulated passageways, referred to as ports. The ports function as conduits for the insertion and exchange of various specialized hand-held or robotic-assisted instruments and devices to accomplish the laparoscopic procedure, which would otherwise be performed by an open surgical incision.

The observed benefits of MIS include reduced blood loss, lower risk of infection, more rapid recovery rates, and reduced postoperative pain. These benefits have caused laparoscopy to become the preferred method for an ever-increasing number of surgical procedures. As with any other surgery, however, MIS is not without its share of complications. Two common complications relevant to MIS surgeries are the formation of abdominal adhesions and/or hernia development.

While laparoscopic adhesion formation occurs less frequently than those related to open surgeries, the risk remains omnipresent as a result of the cumulative effect of the fibrin-forming inflammatory process. Factors that predispose the development of adhesions include: ischemia (poor blood supply), obesity, malnutrition, diabetes, or the devascularization of the peritoneum caused by the surgery itself. The development of adhesions generally occurs between the fifth and seventh postoperative day, resulting in scar-like bands. These adhesive bands may surround the intestine and adhere them either together, or to the peritoneum of the interior abdominal wall. However, months to years later after the initial surgery, these constrictive bands may form a thickened fibrous web which, when fully compact, are capable of inflicting severe pain or causing an intermittent-to-complete bowel obstruction. These two unfortunate scenarios will likely translate into higher medical costs related to emergency surgical procedures, lengthy hospital admissions, and prolonged recovery periods.

The other complication related to minimally invasive procedures is the port-site wound hernia, also referred to as an incisional or ventral hernia. The port-site wound hernia is defined as the abnormal protrusion of abdominal viscera through the wound's fascial defect. This type of hernia commonly develops in the first four years after the index surgery. At present, there is a problematic lack of long-term data on the incidence and natural history of port-site hernia development. Significant contributing factors for port-site wound herniation relate to the size and location of the fascial defect.

Obese patients, with a body mass index (BMI) of thirty or greater, are more susceptible to port-site wound herniation regardless of the fascial defect's size. This may be attributed to the obese patient's enlarged pre-peritoneal space and/or tendency toward elevated intra-abdominal pressures. Extensive manipulation and stretching of the instrument port during the MIS procedure (i.e. retrieval of specimens, multiple re-insertions, or aggressive use of laparoscopic instruments or devices) may enlarge the size of the fascial defect beyond the wound's initial diameter thus rendering the fascial defect vulnerable to port-site wound herniation.

With regards to location, herniation occurs more frequently when the fascial defect is located in the midline of the abdomen, especially in the upper midline area or at the umbilicus, possibly due to the absence of supporting musculature in these areas. In contrast, port-site wound hernias occur less often when they are located below the umbilicus or more laterally on the abdomen.

Another contributing factor for the development of a port-site wound hernia is known as the Chimney Effect. This describes a partial vacuum that is created as the surgical cannula is withdrawn from the wound, much like a piston. As this negative pressure increases within the narrow perimeter of the wound, it is capable of drawing abdominal viscera through the fascial defect and in the subcutaneous tissue or out of the body, thus creating the port-site wound hernia.

There are two technical risk factors for port-site wound hernia: the surgical trocar design used for creating the wound, and/or the suture used for closing the fascial defect. With regards to the former, the bladed trocar presents a greater risk for port-site wound hernia development than non-bladed trocars. Port-site wound herniation may also be related to the repair of the fascial defect with suture, as exemplified by suture fractures, slipping of suture knots, excessive suture tension, or sutures that absorb too rapidly. Suture closure of these wounds can be time consuming and difficult whether the suturing method is performed by the traditional approach (a needle attached to a suture and operated by a needle holder held in the operator's hand), or by a contemporary method using wound closure devices. The latter generally incorporates a needle or sharp tool with a suture affixed to one end in order to approximate and close the fascial defect.

Regardless of the method, the application involves the same time-consuming and cumbersome approach for employing a needle (or sharp tool) with a suture affixed to one end in order to approximate and close the fascial defect within the narrow recesses of the port-site wound. Moreover, these suture techniques have the predictable risk of injuring the underlying bowel, omentum, or other organs as the needle is swept through the fascial tissues.

In obese patients these suturing methods can be painstakingly difficult, since the fascia is obscured from view by adipose tissue. If the fascial defect is too deep and/or is located at a steep angled trajectory in relation to its small skin incision, a blind attempt (e.g., with no direct vision) is the only option for closing the fascial defect. This risky suturing effort generally fails to capture a sufficient margin of the wound's edge.

With regards to the contemporary devices, they may share the same vexing difficulties as the traditional method. However, a specific drawback with these devices relates to their requirement for a pneumoperitoneum and direct visualization during their surgical application. This time-consuming requirement proves problematic, since all of these devices are unable to close the port operating the telescopic lens.

These technical challenges can compromise the wound's integrity, resulting in complications such as poor wound healing, suture failure, and port-site wound herniation, all of which will inadvertently negate the advantages of the MIS procedure. Ultimately, these complications will lead to increased pain and loss of productivity for the patient, while at the same time reducing efficiency with increased costs to the health care system in general.

SUMMARY OF THE DISCLOSURE

Since the advent and proliferation of minimally invasive surgeries there has been a longstanding need for a rapid, safe and effective means of closing the strongest and most complete tissue layer of the port-site wound, specifically the anterior fascia of the abdominal wall. Embodiments of the disclosure are directed to an apparatus and method for the optimal closure of minimally invasive port-site wounds that, in contrast to traditional and contemporary approaches for closing the fascial defect, include enhancements to prevent complications while facilitating wound healing.

By virtue of its unique one-piece design, the apparatus can function as its own insertion device, deployment tool, and highly sophisticated tissue engineered implant. Regenerative medicine may play a role in the development of the wound plug's bio-chemical properties by exhibiting characteristics that, when exposed to living tissues of the body, may not cause damage or adverse biological reactions (e.g., it may be biocompatible); may physiologically degrade and may be absorbed during a specific period of time (e.g., it may be bioabsorbable); and may be completely eliminated by the body's natural processes with no residual side effects (e.g., it may be bioresorbable). These essential characteristics may synergistically regenerate and heal the damaged tissues of the wound. The process can sustain the wound plug's durability and strength for the period of time deemed necessary for the wound plug to be absorbed by the body as the new tissues take its place. In this way, the apparatus can effectively, safely, and easily seal and close the fascial defect of the port-site wound.

The apparatus can be inserted and deployed within any size, depth or angle of port-site wound. Due to its highly versatile design, the apparatus can accurately locate the anterior abdominal fascia surrounding the fascial defect. The apparatus can ensure optimum application and deployment of its wound plug without necessitating the use of any surgical cannula, pneumoperitoneum, or telescopic lens to aid in its insertion, delivery, or deployment.

The apparatus can secure closure of the fascial defect by deployment of a unidirectional ratchet-rivet mechanism that engages the tissues of the fascial defect gently between two rivet heads. The apparatus can be deployed above, below, and within the anterior fascial defect, causing the defect to become gently sandwiched within the non-traumatic clamping force of the apparatus's wound plug. This three-dimensional approach for closing and sealing the defect echoes three basic tenets proposed in hernia mesh science. The first is the apparatus's suprafascial rivet head, which can secure the anterior fascial defect from above as an overlay. The second is the apparatus's subfascial rivet head, which can affix below the defect as an underlay. The third tenet can be achieved by the inlay position of the wound plug's shape memory column (stationed between the two rivet heads) that can fill and seal the void from within the fascial defect. The column can be compressible to fill any size wound and to keep body tissue from entering the wound. Further, it can fill in any gaps to prevent the other elements of the wound plug from shifting.

The tissues of the fascial defect may not be strictly fixed by the apparatus, which significantly reduces the detrimental effects of tissue ischemia (poor blood supply) or necrosis (tissue death) within the wound. The wound plug can spread over a wide surface area, beyond the circumference of the wound, to secure and promote tissue adherence and cellular growth. Another benefit of the wound plug's comprehensive overlay, underlay and inlay of the fascial defect and surrounding tissues is to prevent the plug from migrating or dislodging from its deployed position.

The straightforward and simple application of the apparatus may greatly reduce operating room expenditures in time, efficiency and labor; reduce risk of future adhesions and herniation; facilitate healing and regeneration of the tissues; reduce pain in the patient; and promote optimal patient outcomes with a rapid recovery rate. The apparatus may incorporate a wound plug that, by virtue of its varied chemical and biological composition, may be capable of providing structural and mechanical support for the ingrowth and regrowth of native tissues by interacting with the body's natural intra-cellular processes vital for wound healing.

BRIEF DESCRIPTION OF THE DRAWINGS

For a better understanding of the various described embodiments, reference should be made to the Detailed Description below, in conjunction with the following drawings in which like reference numerals refer to corresponding parts throughout the figures.

FIG. 1A-1B illustrate the wound closure apparatus according to embodiments of the disclosure.

FIGS. 3A-3B illustrate a post according to embodiments of the disclosure.

FIGS. 19A-19E illustrate a wound closure apparatus according to embodiments of the disclosure.

DETAILED DESCRIPTION

Figure 2K:
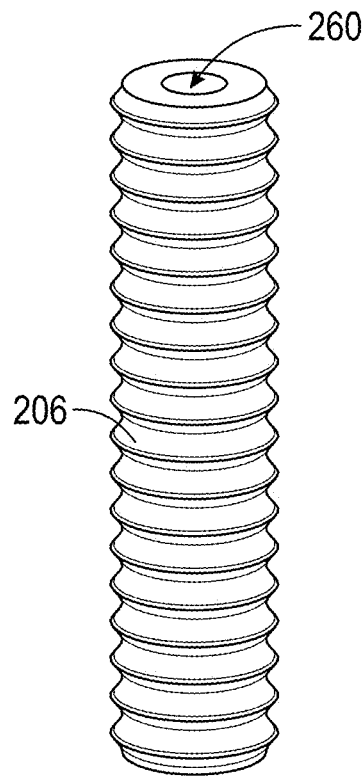
FIGS. 2A-2N illustrate the wound plug according to embodiments of the disclosure.
Figure 2L:
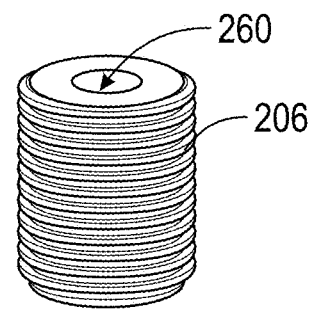
Figure 2M:
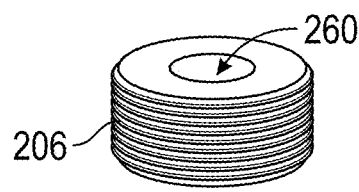

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

Since the advent and proliferation of minimally invasive surgeries there has been a longstanding need for a rapid, safe and effective means of closing the strongest and most complete tissue layer of the port-site wound, specifically the anterior fascia of the abdominal wall. Embodiments of the disclosure are directed to an apparatus and method for the optimal closure of minimally invasive port-site wounds that, in contrast to traditional and contemporary approaches for closing the fascial defect, include enhancements to prevent complications while facilitating wound healing.

By virtue of its unique one-piece design, the apparatus can function as its own insertion device, deployment tool, and highly sophisticated tissue engineered implant. Regenerative medicine may play a role in the development of the wound plug's bio-chemical properties by exhibiting characteristics that, when exposed to living tissues of the body, may not cause damage or adverse biological reactions (e.g., it may be biocompatible); may physiologically degrade and may be absorbed during a specific period of time (e.g., it may be bioabsorbable); and may be completely eliminated by the body's natural processes with no residual side effects (e.g., it may be bioresorbable). These essential characteristics may synergistically regenerate and heal the damaged tissues of the wound. The process can sustain the wound plug's durability and strength for the period of time deemed necessary for the wound plug to be absorbed by the body as the new tissues take its place. In this way, the apparatus can effectively, safely, and easily seal and close the fascial defect of the port-site wound.

The apparatus can be inserted and deployed within any size, depth or angle of port-site wound. Due to its highly versatile design, the apparatus can accurately locate the anterior abdominal fascia surrounding the fascial defect. The apparatus can ensure optimum application and deployment of its wound plug without necessitating the use of any surgical cannula, pneumoperitoneum, or telescopic lens to aid in its insertion, delivery, or deployment.

The apparatus can secure closure of the fascial defect by deployment of a unidirectional ratchet-rivet mechanism that engages the tissues of the fascial defect gently between two rivet heads. The apparatus can be deployed above, below, and within the anterior fascial defect, causing the defect to become gently sandwiched within the non-traumatic clamping force of the apparatus's wound plug. This three-dimensional approach for closing and sealing the defect echoes three basic tenets proposed in hernia mesh science. The first is the apparatus's suprafascial rivet head, which can secure the anterior fascial defect from above as an overlay. The second is the apparatus's subfascial rivet head, which can affix below the defect as an underlay. The third tenet can be achieved by the inlay position of the wound plug's shape memory column (stationed between the two rivet heads) that can fill and seal the void from within the fascial defect. The column can be compressible to fill any size wound and to keep body tissue from entering the wound. Further, it can fill in any gaps to prevent the other elements of the wound plug from shifting.

The tissues of the fascial defect may not be strictly fixed by the apparatus, which significantly reduces the detrimental effects of tissue ischemia (poor blood supply) or necrosis (tissue death) within the wound. The wound plug can spread over a wide surface area, beyond the circumference of the wound, to secure and promote tissue adherence and cellular growth. Another benefit of the wound plug's comprehensive overlay, underlay and inlay of the fascial defect and surrounding tissues is to prevent the plug from migrating or dislodging from its deployed position.

The straightforward and simple application of the apparatus may greatly reduce operating room expenditures in time, efficiency and labor; reduce risk of future adhesions and herniation; facilitate healing and regeneration of the tissues; reduce pain in the patient; and promote optimal patient outcomes with a rapid recovery rate. The apparatus may incorporate a wound plug that, by virtue of its varied chemical and biological composition, may be capable of providing structural and mechanical support for the ingrowth and regrowth of native tissues by interacting with the body's natural intra-cellular processes vital for wound healing.

Apparatus

FIGS. 1A-1B illustrate a wound closure apparatus 100 according to embodiments of the disclosure. The apparatus can be a self-contained device for delivery and deployment of a tissue engineered wound plug 200 that can secure fascial closure of laparoscopic port-site wounds. The wound plug 200 can include a subfascial rivet head 202, a suprafascial rivet head 204, and a compressible column 206, wherein the compressible column surrounds and is coupled to each of the subfascial rivet head and the suprafascial rivet head.

The apparatus may include a post 300, a rod 400, and a shield 500 for delivery and deployment of the wound plug 200. The post 300 can include the subfascial rivet head 202 at a first end of the post and a handle 322 at a second end of the post. The rod 400 can have a rod cavity 466 through which the post 300 is positioned. A first end of the rod 400 can be in contact with the suprafascial rivet head 204 of the wound plug 200, and the rod can include a plate 426 at a second end of the rod. The shield 500 can include portions of the wound plug 200, the post 300, and the rod 400 in a shield cavity 530.

Once in the wound, these components can deploy the wound plug 200 with the subfascial rivet head 202 below the fascia 750 of the wound and the suprafascial rivet head 204 above the fascia of the wound 748. As this occurs, the column 206 of the wound plug 200 can be stationed within the opening of the wound. Once the wound plug 200 is secured above, below, and within the fascial defect, the two components of the rivet heads 202 and 204 may be interlocked within an inner channel 260 of the column 206. As a result, the wound plug 200 may be implanted into the port-site wound's fascial defect, while the post 300, the rod 400, and the shield 500 may be removed from the wound and safely discarded.

The apparatus's design, consisting of its own deployment device and implant, creates a mechanical symbiosis that precludes the need for any other additional accessories (e.g., other tools or instruments), or conditions of the wound (e.g., pneumoperitoneum, telescopic visualization, wound retraction, or increasing the length of the skin incision).

Wound Plug

Figure 2N:
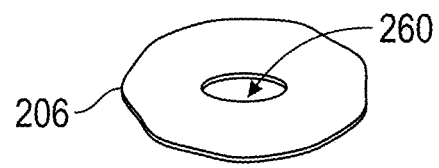

FIGS. 1B and 2A-2N illustrate a wound plug 200 according to embodiments of the disclosure. In some embodiments the wound plug includes a subfascial rivet head 202, a suprafascial rivet head 204, and a compressible column 206. In some embodiments, the subfascial rivet head 202 includes a subfascial extension 208 comprising a plurality of stays 210, and the suprafascial rivet head 204 includes a suprafascial extension 212 including a plurality of stays 214. In some embodiments, the wound plug 200 further includes a subfascial biohybrid scaffold 216 coupled to the subfascial extension 208 and a suprafascial biohybrid scaffold 218 coupled to the suprafascial extension 212.

FIGS. 2A-2D illustrate subfascial and suprafascial rivet heads 202 and 204 according embodiments of the disclosure. The rivet heads 202 and 204 may be composed of natural polymers or copolymers like chitosan, gelatin, alginate, collagen and/or other wound healing promoters; as well as synthetic polymers or copolymers such as Polyglycolide (PGA), Polylactide (PLA), Polydioxanone (PDO), Polycaprolactone (PCL), or synthetic copolymers like L-lactide-co-glycolide (PLGA). The possibilities for such fabrication techniques may include but are not limited to polymeric blends, dip coating, adhesive layering, copolymerization, grafting, homogeneous mixtures, and/or electrospinning for creating a biosynthetic composite material.

This skeletal architecture can be manufactured from a polymeric composite for superior tissue engineering. A synthetic polymer or copolymer may be desirable because it demonstrates mechanical and physiochemical characteristics similar to those of the biological tissue it will temporarily replace. Additionally, synthetics can be tailored to control their microstructure and degradation rate. In contrast, however, natural polymers can have bioactivity-possessing growth factors and pertinent signals that may facilitate cellular adhesion, growth, and proliferation. Consequently, the strength of the former, and the bioactivity of the latter may mutually provide intrinsic benefits while diminishing each other's deficiencies.

The semi-rigid polymer composite of this skeletal architecture can be designed with microscopic perforations, which provide a gradient through which the native tissue cells may proliferate. As the device degrades within the body these perforations may be critical for tissue adherence and optimal cellular response and healing. Moreover, a natural polymer may be adhered as a layer upon the synthetic polymer construct.

The subfascial rivet head 202 may be a part of the post 300 at a first end of the post, separated from the rest of the post by a breakaway point 320. The post 300 can be used to position the subfascial rivet head 202 below the fascia 750 into the pre-peritoneal space, and the post can be broken at the breakaway point 320 to separate the subfascial rivet head 202 from the rest of the post after the wound plug 200 is deployed in its entirety.

In some embodiments, the subfascial rivet head 202 may comprise an engaging ratchet configured to engage with a hollow receiving pawl of the suprafascial rivet head 204. For example, the engaging ratchet may include a number of flanges 256 configured along its exterior that correspond to a number of reciprocal annular grooves 258 within the interior of the receiving pawl. Once the rivet heads 202 and 204 are deployed, the subfascial and suprafascial portions of the wound plug 200 become interlocked by deployment of the unidirectional mechanism.

In some embodiments, the suprafascial rivet head 204 may comprise a hollow receiving pawl configured to engage with an engaging ratchet of the subfascial rivet head 202. For example, the receiving pawl may include a number of reciprocal annular grooves 258 configured within its interior that correspond to a number of flanges 256 on the exterior of the engaging ratchet. Further, the suprafascial rivet head 204 may be configured with a channel to allow the post 300 to pass through its hollow core.

In some embodiments, engagement of the subfascial and the suprafascial rivet heads 202 and 204 may be confirmed by three audible clicks synchronized with three tactile sensations. These effects confirm that the reciprocal annular grooves 258 of the receiving pawl have successfully interlocked with the flanges 256 of the engaging ratchet.

In some embodiments, extensions 208 and 212 surround the outer perimeters of each rivet head 202 and 204. For example, FIGS. 2E-2F illustrate each extension 208 and 212 including a plurality of stays 210 and 214. In some examples, the number of stays on each rivet head can be chosen relative to the size of each rivet head extension 208 and 212, as well as to the weight and size of their associated biohybrid scaffold 216 and 218. The cross sectional profile of each stay may be tapered on one side 262 and non-tapered (e.g., flat) on the opposing side 264. This profile can be consistent throughout the length of each stay, terminating into a blunt-point end.

The stays 210 and 214 may be fabricated using shape memory properties, allowing for two different configurations during the implant's surgical application. Prior to deployment, the stays may project at 90° angles from the outer perimeter of each rivet head, offset relative to each other at a 45° angle of arc. In this second configuration, the stays may be superiorly and inferiorly convergent as they enclose an outer wall of the column 206 in an alternating fashion. Further, each stay may include two distinct surfaces 262 and 264. Within the apparatus 100, a first non-tapered surface 264 may be adjacent to the wall of the column 206, whereas a second tapered surface 262 may encircle an outer perimeter of the column 206 exteriorly.

Once the rivet heads 202 and 204 are deployed, however, the shape memory properties of the stays 210 and 214 can be immediately affected by the body's temperature and/or pH relative to a pre-determined time interval also inherent in their chemical properties. These physical and biological properties can cause each stay to automatically deploy its corresponding biohybrid scaffold (e.g., biohybrid scaffolds 216 and/or 218) into a full radial expansion above and below the fascial defect, thus orienting the stays' non-tapered surfaces 264 toward the abdominal fascia, while their tapered surfaces 262 are adjacent to the native tissues surrounding the port site wound (e.g., native tissues 768 in FIGS. 6C and 6D).

Although FIG. 2E illustrates just the subfascial extension 208 including the plurality of stays 210, in some embodiments, the subfascial extension 208, the plurality of stays 210, the subfascial rivet head 202, and the post 300 are all formed of a single piece. Further, although FIG. 2E illustrates just the suprafascial extension 212 including the plurality of stays 214, in some embodiments, the suprafascial extension 212, the plurality of stays 214, and the suprafascial rivet head 204 are all formed of a single piece.

In some embodiments, the rivet heads 202 and 204 may include a disc shape as illustrated in the figures. In some embodiments, the rivet heads may alternatively include other shapes, such as rectangular, oval, hexagonal, octagonal, star, square, etc.

In some embodiments, the rivet heads 202 and 204 may be manufactured from the same shape memory blend of natural and synthetic polymers (or copolymers) as the extensions 208 and 212. In this way, the rivet heads can change to a smaller or more compact profile, such as a cone or ball.

In some embodiments, the stays 210 and 214 may be profiled to be tapered or non-tapered, thick or thin, wide or narrow, etc. In some embodiments, the stays may be profiled in such a way that their central convergence forms the receiving pawl and engaging ratchet. In this embodiment, the stays may be configured in linear geometric shapes (i.e., spokes on a bicycle wheel, or a lattice-like network), or as a mosaic of crisscrossing curves (i.e., lace-like or snowflake designs) for establishing the skeletal framework of the rivet heads 202 and 204, as well as the rivet head extensions 208 and 212.

Although embodiments of the disclosure are described in terms of rivet heads comprising a receiving pawl and an engaging ratchet, embodiments are not so limited. Other embodiments are contemplated for attaching the suprafascial and subfascial portions of the wound plug 200, such as superior and inferior clasps, mechanical fasteners, crimp engagements, mechanical latches, suture tie(s) with a type of slip knot(s), post or bead-like snaps, a tapering pin that engages within a narrowing hole, hook and eye attachments, a type of buckling apparatus, or even a chemical tissue adhesive disseminating from the column 206.

FIGS. 2G-2J illustrate biohybrid scaffolds 216 and 218 according to embodiments of the disclosure. In some embodiments, the scaffolds 216 and 218 may comprise a collagen rich acellular non-crosslinked tissue sheet that is replete with vital components for wound healing, such as laminin, biometric proteins, carbohydrates, etc. When these multi-layered tissue sheets are applied to a wound site, a synergy between its scaffold and the native tissues can develop, causing specialized living cells to proliferate and regenerate new tissue into the wound site.

In some embodiments, the biohybrid scaffolds 216 and 218 include two distinct surfaces. A first surface 252, the lamina propria layer, may be conducive for tissue regeneration and healing. In contrast, the second surface 254, the epithelial basement membrane, may be beneficial as a collagen rich tissue scaffold. The scaffolds may be deployed such that the first surface 252 is in contact with the abdominal fascia around the fascial defect 748 and 750, while the second surface 254 is in contact with surrounding native tissues of the wound (e.g., native tissues 768 in FIGS. 6C and 6D).

In some embodiments, the biohybrid scaffolds 216 and 218 may cover and embed only the flatter, larger surfaces of the rivet heads 202 and 204 and both sides of each of the stays 210 and 214 with the exception of the stays' distal blunt ends. The scaffolds 216 and 218 may include centralized openings to allow portions of the rivet heads 202 and 204 and the vertical axis of the post 300 to pass through the centers of the scaffolds.

In some embodiments, an electrospun layer may be applied between the tissue surfaces of each biohybrid scaffold 216 and 218 directly contacting the shape memory components of the stays 210 and 214. This may further promote cohesiveness between the two layers for strength and manageability.

Prior to deployment biohybrid scaffolds 216 and 218 can conform to the same constricted configuration presented by the embedded stays 210 and 214. In this deformed profile, the lamina propria layer 252 can be adjacent to the wall of the column 206, while the epithelial basement membrane 254 can encircle the column exteriorly. In this pre-deployment profile, the scaffold tissue sheets may appear as multiple vertical pleats, in the likeness of a pleated paper coffee filter, although pleats may be more rounded or larger in nature.

Once the rivet heads 202 and 204 are deployed, the bio-reactivity of the surrounding stays 210 and 214 can simultaneously spread its corresponding biohybrid scaffold 216 and 218 into full radial expansion. As a result, the lamina propria layer 252 that encases the inner (fascial) surfaces of the rivet heads and stays (e.g., the non-tapered surfaces 264) may be juxtaposed to one another as they cover the subfascial and suprafascial surfaces 750 and 748 surrounding the wound 744. Further, the epithelial basement membrane 254 covering the exterior sides of the rivet heads and the tapered surfaces 262 of the stays can buttress the surrounding native tissues (e.g., native tissues 768 in FIGS. 6C and 6D). Consequently, following deployment each rivet head's outer diameter may be large enough to thoroughly cover both sides of the defect.

In some embodiments, the scaffolds may be produced with other types of biological or synthetic (absorbable or nonabsorbable) scaffolding materials.

In some embodiments, the skeletal framework of the rivet heads and the stays may not be included, and instead the shape memory biohybrid scaffolds of each rivet head may be resilient enough to deform into a pre-deployment configuration without the necessity of any supportive skeletal framework.

In the absence of the skeletal framework, it may be beneficial for a tissue adhesive to be dispersed from the column 206 to cause the two biohybrid scaffolds to adhere locally to the wound. If a tissue adhesive is used for securing the wound plug to the wound, there may be no need for a mechanical fixation apparatus such as an engaging ratchet or a receiving pawl. As a result, this alternative suggests only a simple open-ended central opening within the suprafascial rivet head 204. Likewise, the post 300 may be a plain shaft (without an engaging ratchet or a breakaway point 320). The distal end of the post may need to be tenuously anchored to the electrospun network within the two layers 252 and 254 of the subfascial biohybrid scaffold 216 covering the subfascial rivet head 202. After deployment, and the local tissue adhesive from the column 206 is dispersed, the terminal end of the post may be twisted, torqued, pulled, or snapped from its temporary electrospun attachments within the subfascial biohybrid scaffold of the subfascial rivet head.

In some embodiments, the biohybrid scaffold 216 and 218 may be uniform, and may have wide or narrow shapes that may include oval, rectangular, star-like or flower-petal projections, etc. In some embodiments, the subfascial and suprafascial biohybrid scaffolds may be profiled in two entirely different geometric shapes and widths. Further, each scaffold may be fabricated from identical biological or chemical properties to that of other elements of the wound plug 200.

FIGS. 2K-2N illustrate a compressible column 206 according to embodiments of the disclosure. The column 206 may be a highly porous shape-memory structure, in the form of a sponge or foam, which provides a large surface area to promote cellular ingrowth, uniform cellular distribution, and neovascularization. The column may be centered between the two rivet heads 202 and 204. Prior to deployment, the receiving pawl and the engaging ratchet may be recessed within an inner channel 260 of the column. In some embodiments, the column may further include an electrospun network between the terminal borders of the column and the fascial surfaces 252 of the biohybrid scaffold 216 and 218 to achieve an integrated fusion between these structures, thus uniting them together as a single unit. As a result, the column's inferior section may be deployed in unison with the subfascial rivet head 202, while the superior portion of the column may be deployed with the suprafascial rivet head 204. After deployment, the column's initial tube-like profile may be positioned within the border of the wound.

The wall of the column 206 may be constructed with multiple compact circumferential pleats, such that the column compresses in an accordion-like fashion as the subfascial and suprafascial portions of the wound plug become interlocked. Accordingly, the length of the column compresses while maintaining its outer diameter so as to not interfere with the interlocking of the rivet heads.

In some embodiments, once the pleats are mechanically compressed, the body's temperature and/or pH can affect shape memory properties of the column 206, causing the column to automatically expand and pervade the interior of the wound in a washer-like profile with an outer diameter that does not fill the central defect. This smaller diameter of the column's washer-like profile can allow for the porous network to absorb blood and body fluids, increasing in size to swell and pervade the wound like a seal. The final configuration of the column, therefore, may fill the central defect like a low-pressure seal or plug without exerting pressure on the bordering tissues of the wound. As a result of this seal, the inner channel 260 of the column may become completely obliterated, thus resulting in an adherence between the column and the engaged components of the rivet heads 202 and 204. The benefit of this adherence is that dead space and vacuums are averted within the interior of the wound plug 200, thereby encouraging tissue regeneration.

In some embodiments, the size, distribution, volume, shape, and roughness of pores within the column 206 may have a powerful influence on cellular penetration and growth. Further, the pores may be interconnected in order to facilitate the essential transfer of oxygen, nutrients, and other physiochemical elements and biological exchanges to and from the living cells.

In some embodiments, the porous structure of the column 206 may be saturated with either a bioactive cellular matrix powder or a biocompatible hydrogel. Saturating the column with one or more of these materials can promote a synergistic interplay between it and the surrounding native tissues of the port-site wound. Additionally, the column's porous construction can incorporate pharmaceutical enhancements into its design, such as tissue adhesives, stem cell recruitment adjuncts, regenerative biochemical factors, insulin growth factor, anesthetic or antibiotic time-released drugs, etc.

In some embodiments, the inner channel 260 of the column 206 surrounding the post 300 and portions of the rivet heads 202 and 204 may be filled with a tissue-healing hydrogel or liquefied state of the same. Following deployment, the locally applied tissue adhesive may be dispersed from the column to function as a chemical securing mechanism for sealing the wound plug to the wound. In some embodiments, the column 206 itself may be made of the hydrogel with an outer wall made of denser gelatinous material (or skin) which encases the more viscous and/or liquefied form.

In some embodiments, the column 206 may include a finely shredded or spider web-like form of the bioactive acellular tissue matrix and/or liquefied form of the same. In some embodiments, the column may be fabricated from any number of materials including a sponge, foam, hydrogel, acellular pig bladder xenograft, any other type of xenografts, synthetic-absorbable scaffolding material, or any combination of these options. In some embodiments, the column may occur as a hollow chamber (i.e., a small bladder) formed by either a xenograft or other type of tissue engineered material that may include pharmaceutical and bioactive substances, hydrogel, and/or the possibility of a tissue adhesive within its interior.

In some embodiments, the column 206 may be formed by stacking multiple centrally-perforated washers, one on top of the other, around the post 300 and the mechanical securing mechanisms of the rivet heads 202 and 204.

In some embodiments, the pleats of the column 206 may be arranged in vertical columns, or curving these vertical columns into a spiraling, candy cane-like design. By arranging the folds or pleats in these configurations, the column may compress like a collapsed spring. Moreover, it may be advantageous to cut these vertical or horizontal lines rather than utilizing pleats and/or folds within the wall of the column. Additionally, a combination of cuts and/or pleats or folds may contribute to a more successful compression for the column during deployment.

Delivery and Deployment Apparatus

The post 300, the rod 400, and the shield 500 form an apparatus 100 for delivery and deployment of the wound plug 200. These three components may reside at different radial levels in the apparatus. The post 300 may be located in the core of the apparatus and may be the longest of the three components, with its handle 322 rising higher than the other two components. The rod 400 surrounds portions of the post 300 and includes a plate 426 at one end (e.g., approximately midway between the handle 322 of the post 300 and grips 538 of the shield 500). The shield 500 surrounds portions of the rod 400 and the post 300 in its shield cavity 530. The shield includes an implant chamber 532 that includes portions of the wound plug 200 before deployment. Each of the post, the rod, and the shield may include an alignment pin hole through which an alignment pin 600 may be placed to align the various components with respect to each other. The alignment pin 600 may be removed prior to deployment, as described below.

In some embodiments, each of the post 300, the rod 400, and the shield 500 may be made of synthetic polymers without the essential blends of polymer composites comprising the wound plug 200. As a result, the overall rigid construction of these elements (e.g., the elements that will not be implanted within the body) may be fabricated from non-critical, bio-safe materials. Once the post, the rod, and the shield are separated from the wound plug and removed from the wound, their byproducts may be safely discarded as environmentally friendly, non-toxic wastes.

FIGS. 3A-3B illustrate a post 300 according to embodiments of the disclosure. The post may be a vertical and most internal axis by which all the components of the apparatus 100 may be collectively aligned and integrated for deployment. In this unique position, the post may traverse proximally throughout a series of internal conduits of the column 206 (e.g., the inner channel 260 of the column), the suprafascial rivet head 204, the rod 400 (e.g., the inner channel 466 of the rod), and the shield 500 (e.g., the shield cavity 530). The alignment of these cannulated components can create a common passageway through which portions of the post 300 can move.

The post 300 may be an injected molded structure comprised of several diverse profiles along its vertical construct, including a subfascial rivet head 202 (e.g., the engaging ratchet) at a first end, and a handle 322 at a second end. The post may further include a breakaway point 320 between the subfascial rivet head and the handle. The breakaway point distinguishes the portion of the post included in the wound plug (i.e., the subfascial rivet head) from the rest of the post. In some embodiments, the breakaway point 320 may be configured to provide vertical stability and strength, thereby resisting compression or elongation during insertion and deployment. However, following the application of minimal twisting torque to the handle 322, the post 300 can break at the breakaway point.

In some embodiments, the post 300 retains a cruciate profile until it transitions into the inferior flanges 256 and distal base of the engaging ratchet. Although the subfascial rivet head 202 is illustrated as having three flanges 256, embodiments are not so limited and can have any number of flanges. The handle 322 may be knurled to facilitate gripping and cylindrical to prevent its descent into the rod 400. In some embodiments, the post 300 further includes an alignment pin hole 324.

In some embodiments, the handle 322 may be profiled in different shapes which include, but are not limited to, a round, flat plate or disc, T-handle, thumb plate, ball, bulb, laterally contoured projections, finger-ring holes, diamond, ribbed finger grip, a rod-like handle, etc. In some embodiments, the shaft of the post 300 may be formed in other non-cruciate shapes, such as geometric shapes like a triangle or diamond, or a simple round or oval profile. Moreover, one or more of the four cruciate crossarms may be added to or removed from the cruciate profile, thus allowing for a variety of shapes which include, but are not limited to, one crossarm projection, two crossarms similar to a dumb-bell shape, three crossarms like a rounded three-leaf clover or a pointed triangular shape, a diamond shape, or multiple rounded or pointed projections as seen in various flower or star-like profiles.

In some embodiments, the breakaway point 320 may be designed to sever either by a snap release, by pulling and/or twisting, or by other physical means, instead of the application of torque discussed above. Additionally, since many of the apparatus's components respond to the body's pH and/or temperature, the breakaway point's chemical properties may be engineered to release within a specific period of time, shortly after deploying the wound plug 200 within the wound.

Figure 4:
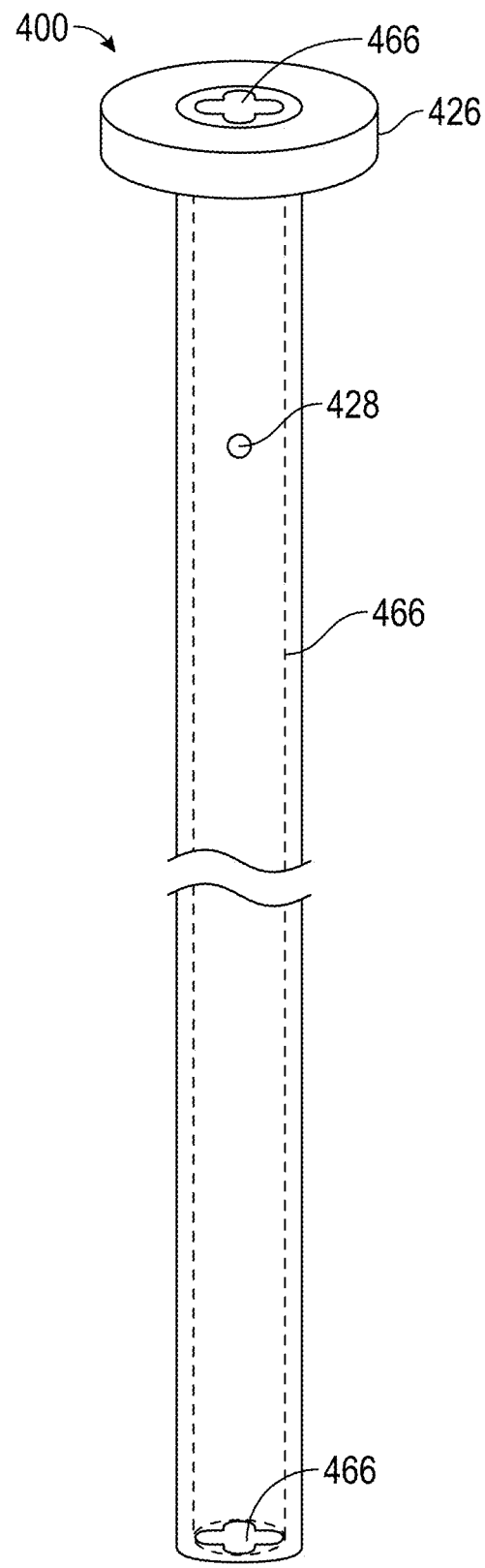
FIG. 4 illustrates a rod according to embodiments of the disclosure.

FIG. 4 illustrates a rod 400 according to embodiments of the disclosure. The rod 400 can include a plate 426 at a second end of the rod, and a first end of the rod can be in contact with the suprafascial rivet head 204 (e.g., the receiving pawl). Prior to deployment, the plate 426 may be positioned midway between the handle 322 of the post 300 and the grips 538 of the shield 500. The rod may further include an alignment pin hole 428. An inner channel 466 of the rod can match a cruciate profile of the post 300, allowing for the vertical movement of the post and the rod without twisting during deployment of each associated rivet head (subfascial rivet head 202 deployed by the post 300, and suprafascial rivet head 204 deployed by the rod 400). Further, the cruciate profile can facilitate fixation of the post 300 above its breakaway point 320, permitting the application of torque to sever the post at the breakaway point.

In some embodiments, the combination of the plate 426 of the rod 400 and the grips 538 of the shield 500 can allow for a syringe-like hold to deploy the suprafascial rivet head 204 and the superior section of the column 206, as described below. In some embodiments, the inner channel 466 of the rod 400 has a non-cruciate shape to match a corresponding non-cruciate shape of the post 300. In some embodiments, the suprafascial rivet head 204 can be a part of the rod 400, separated from the plate 426 by a breakaway point that functions similarly to the breakaway point 320 of the post 300. The breakaway point of the rod can align with the breakaway point of the post after deployment such that a single twisting motion can sever both.

Although the figures illustrate a single shape for the plate 426, variations in shapes, thicknesses, sizes, etc. are contemplated by this disclosure.

Figure 5A:
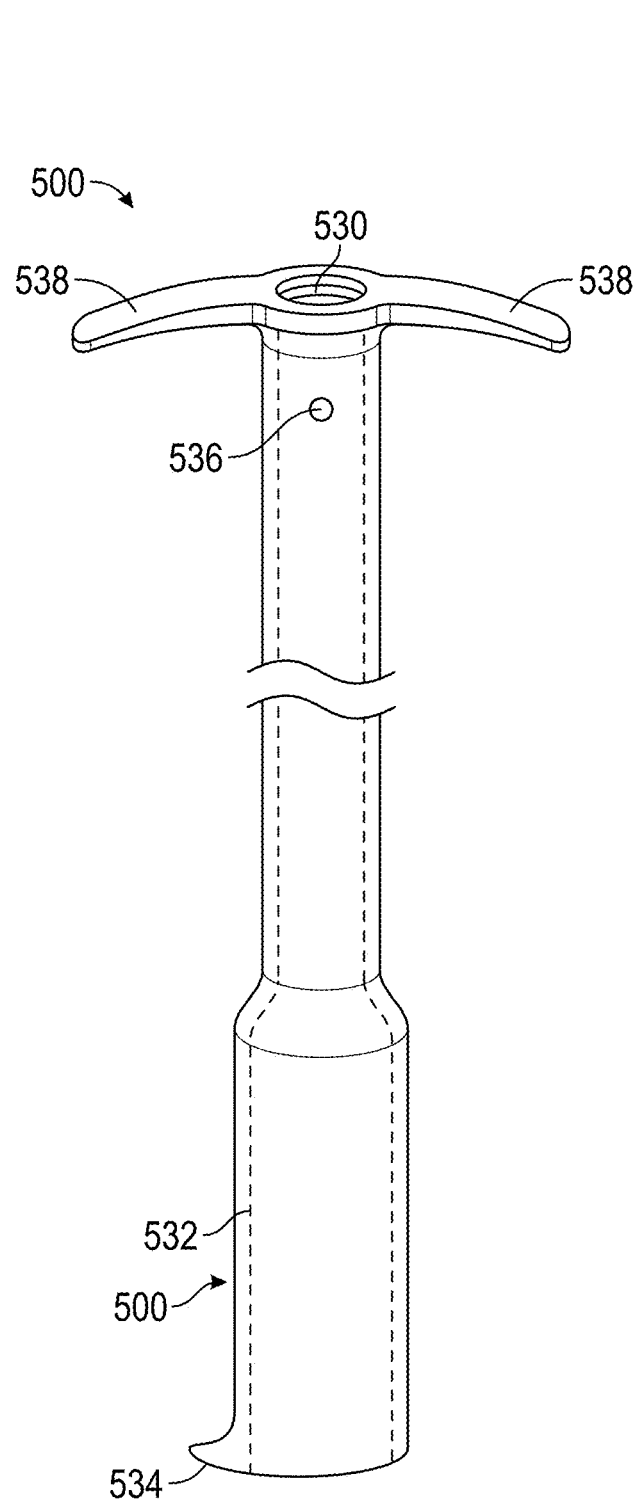
FIGS. 5A-5C illustrate a shield according to embodiments of the disclosure.
Figure 5B:
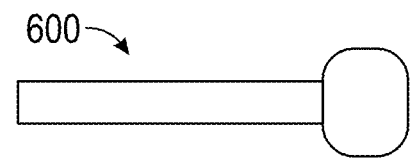
Figure 5C:
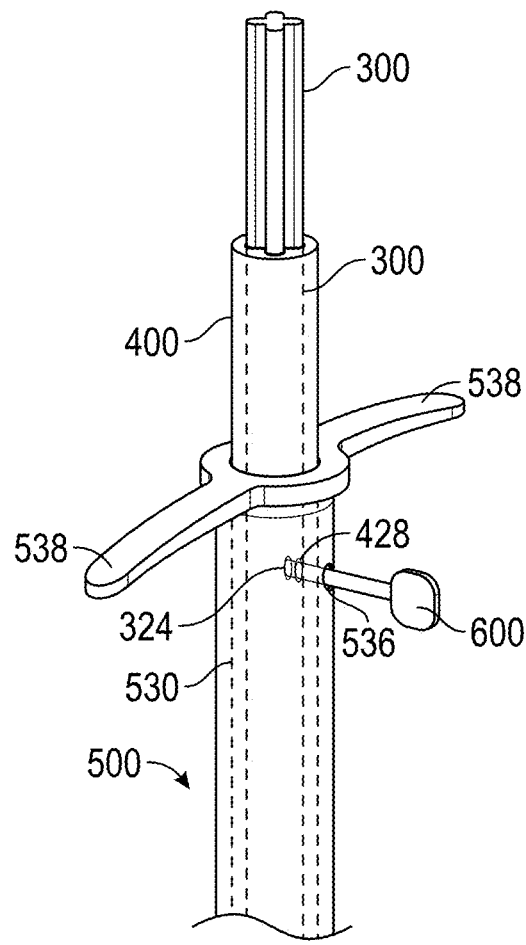

FIGS. 5A-5C illustrate a shield 500 according to embodiments of the disclosure. The shield 500 can include a shield cavity 530 and an implant chamber 532 that houses portions of the wound plug 200 prior to deployment. In some embodiments, the shield further includes grips 538 to allow a user to hold the device like a syringe with a comfortable grip for the deployment of the suprafascial rivet head 204 and the column 206. The implant chamber 532 may be profiled in an inverted cup-like configuration. A rim of the implant chamber may be wider than the wound in the fascia, such that the shield 500 can rest on the fascia without entering the wound 744, and so that the contact between the fascia and the rim provides physical feedback to the user indicating that the wound plug is correctly positioned with respect to the depth of the fascia beneath the skin, allowing for use of the apparatus without internal or external direct vision of the wound 744. Further, the rim of the implant chamber may include an insertion lip 534 to facilitate easy insertion of the apparatus beneath a narrow skin incision.

In some embodiments, the shield 500 may further include an alignment pin hole 536. The linear arrangement of the three alignment pin holes in the post 300, the rod 400, and the shield 500 can create a common opening for insertion of an alignment pin 600 to keep the components in place until ready for deployment, as illustrated in FIG. 5C. The alignment pin may be removed once the rim of the implant chamber 532 is centered over the wound in the fascia.

In some embodiments, the insertion lip 534 of the implant chamber 532 may project in shapes including a quarter or half circle, a quarter or half oval, a more pointed design, an encircling band or brim, a ring, or a ridge. One or more additional insertion lips may also be included on the rim of the implant chamber 532.

In some embodiments, a $CO_2$ sensor or pressure gauge may be devised along the rim and/or lip of the implant chamber 532 which can register a visual cue in a window constructed within the wall of the shield 500.

In some embodiments, concentric grooves appearing as screw-like threads or spiral-like grooves may be profiled to the exterior wall of the shield 500. The purpose of these grooves may be to promote an easier insertion of the device within the subcutaneous tunnel of the wound. However, it may be determined that vertically aligned grooves, in contrast to the horizontal grooves, like the screw or spiral-like profiles, may effect easier insertion of the apparatus into the wound.

In some embodiments, some or all of the shield 500 may be profiled in numerous shapes, sizes, thicknesses, etc. For example, the grips 538 may be profiled in any geometric shape for designing the laterally oriented projections or rings, and any number of grips are contemplated.

Method of Deployment

Figure 6A:
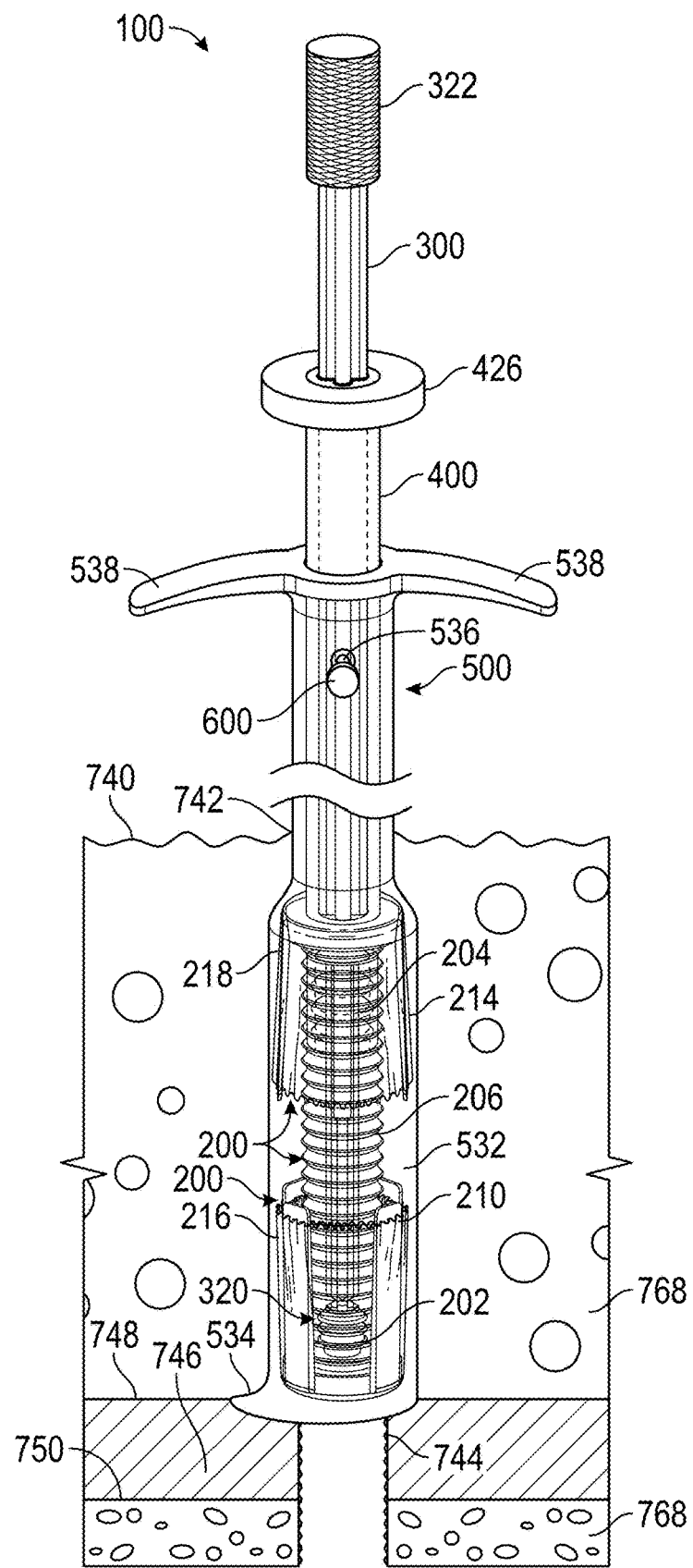
FIGS. 6A-6D illustrate the apparatus during stages of deployment of the wound plug according to embodiments of the disclosure.
Figure 6B:
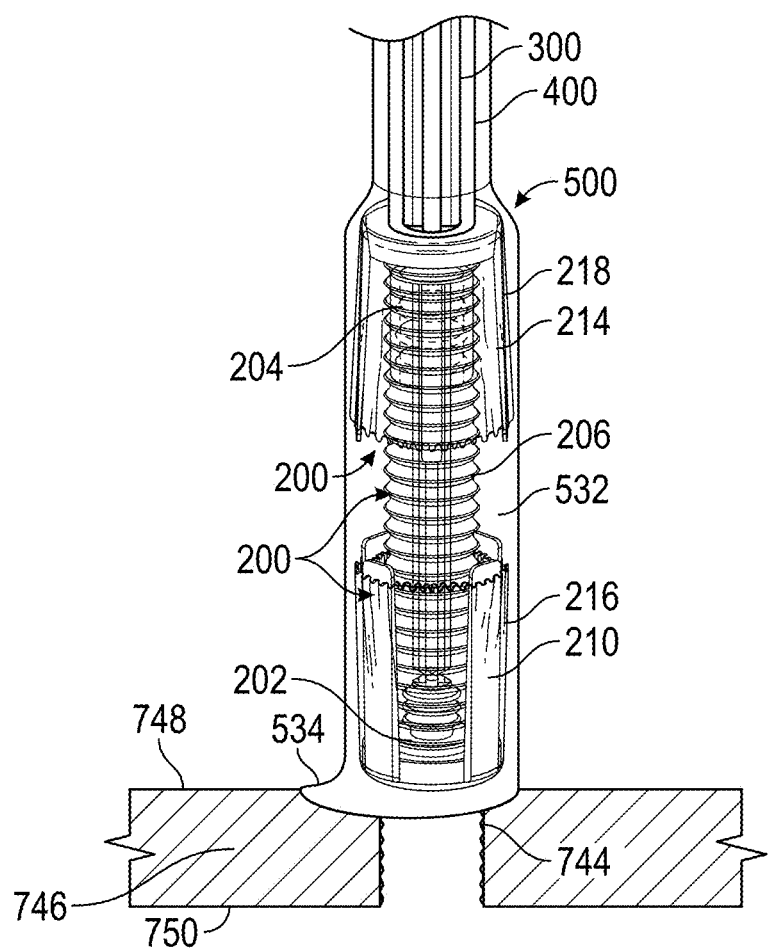
Figure 6C:
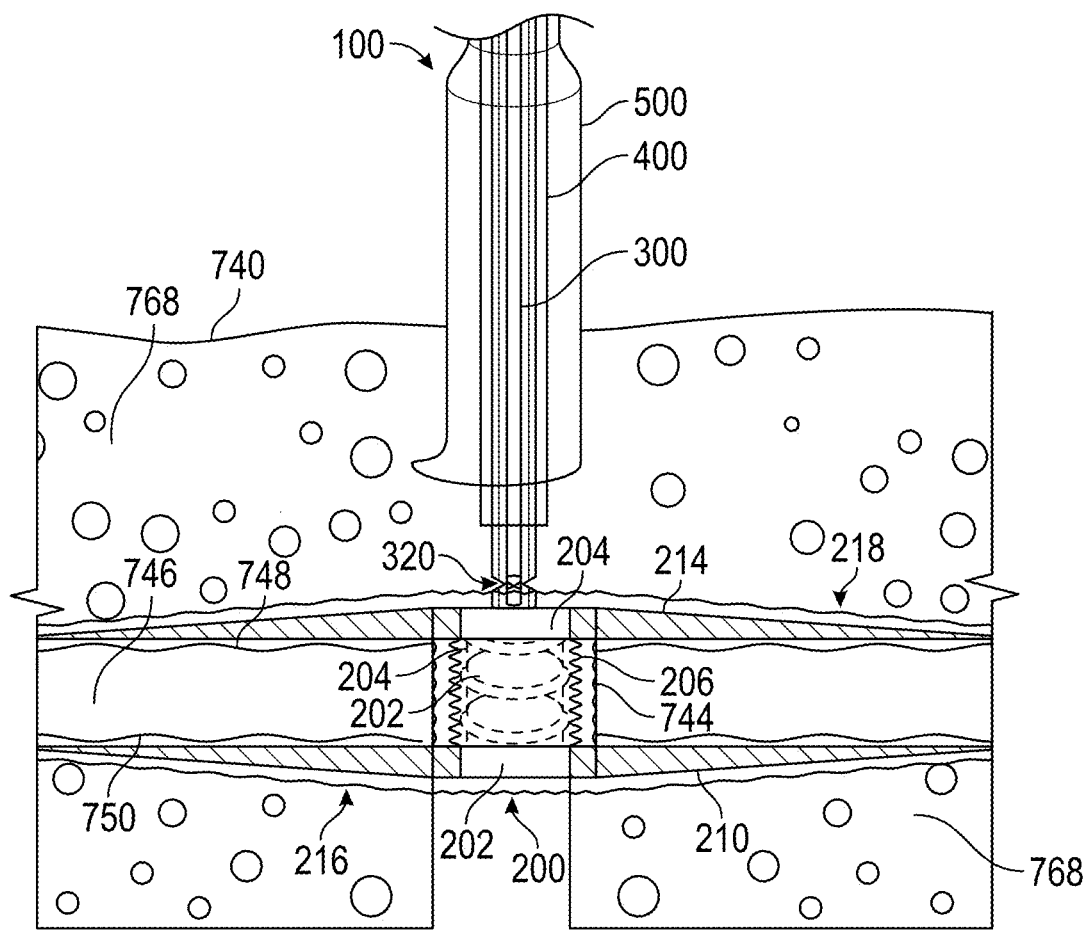
Figure 6D:
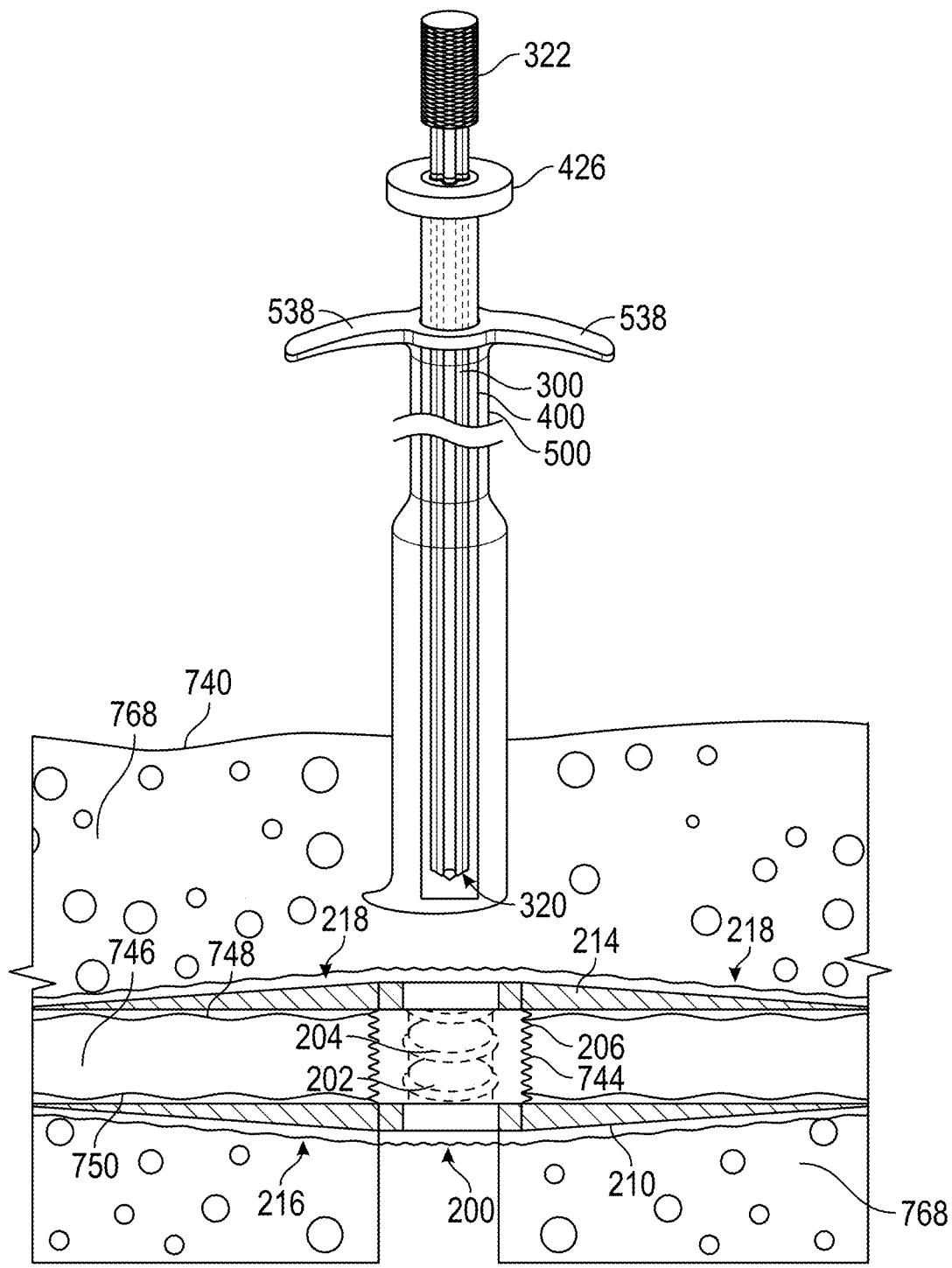
Figure 7:
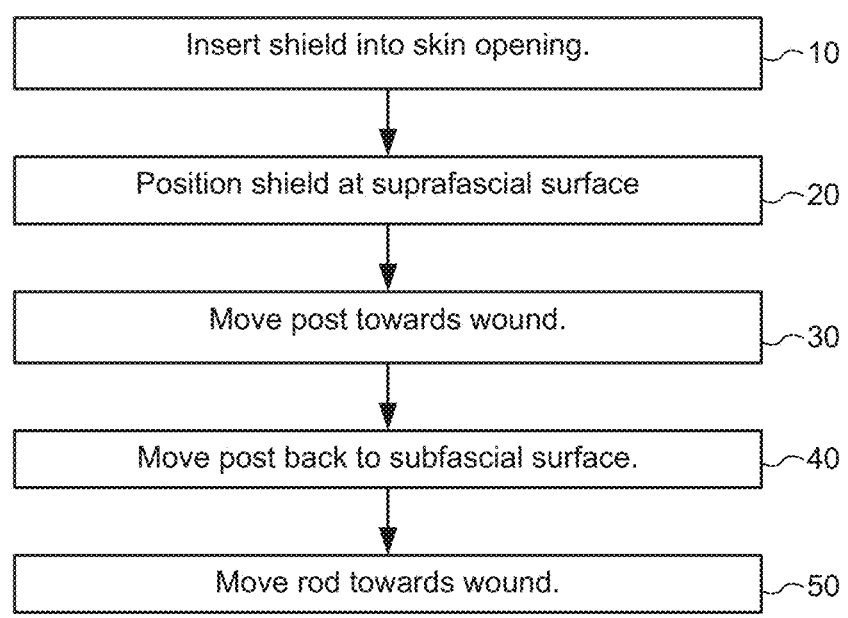
FIG. 7 is a block diagram of a method for deploying a wound plug according to embodiments of the disclosure.

FIGS. 6A-6D illustrate the apparatus 100 during stages of deployment of the wound plug 200, and FIG. 7 is a block diagram of a method for deploying a wound plug according to embodiments of the disclosure.

The shield 500 may be inserted (10) into a skin opening 742 in the skin 740. The shield's implant chamber 532 may be slightly larger than the skin opening 742, so holding the apparatus at a 45° angle may allow the apparatus to slip easily beneath the skin incision without extension of the wound or the need for skin retraction.

The shield may be positioned (20) such that the rim of the implant chamber 532 is in contact with a suprafascial surface 748 of fascia 746 surrounding a wound 744 in the fascia, as illustrated in FIGS. 6A-6B. In some embodiments, the rim of the implant chamber may be wider than the wound in the fascia, such that the shield can rest on the fascia 746 without entering the wound 744, and allowing for use of the apparatus without internal or external direct vision of the wound in the fascia. Further, the contact between the fascia and the rim may provide physical feedback to the user that the wound plug is correctly positioned with respect to the depth of the fascia 746 beneath the skin 740.

In some embodiments, the alignment pin 600 may be removed from the alignment pin holes 324, 428, and 536 of the post 300, the rod 400, and the shield 500, respectively.

The post 300 may be moved (30) towards the wound 744 (e.g., by gripping and moving the handle 322 of the post) such that a subfascial extension 208 coupled to the subfascial rivet head 202 (e.g., engaging ratchet) at the first end of the post passes through the wound. The subfascial rivet head 202, the subfascial biohybrid scaffold 216, and an inferior portion of the column 206 may thereby pass into the native tissues 768 of the pre-peritoneal space.

After the subfascial extension 208 passes through the wound 744, the post 300 may be moved (40) such that the subfascial extension is in contact with a subfascial surface 750 around the wound 744 (e.g., by gripping and pulling the handle 322 of the post until resistance is felt when the subfascial extension comes into contact with the subfascial surface). The subfascial biohybrid scaffold 216 and corresponding subfascial plurality of stays 210 of the subfascial extension may be fully radially expanded at this point below the fascial defect within the pre-peritoneal space. Further, the inferior portion of the column 206 including a portion of the subfascial rivet head 202 may positioned within the wound.

The rod 400 may be moved (50) toward the wound 744 (e.g., by holding the handle 322 of the post 300 in a stationary position with one hand, and with the opposite hand pushing together in a syringe-like manner the grips 538 of the shield 500 and the plate 426 of the rod). As a result of this motion, the receiving pawl 204 may be pushed by the rod towards the engaging ratchet 202, the engaging ratchet may interlock within the receiving pawl, the compressible column 206 may be compressed within the wound, and a suprafascial extension 212 (e.g., including a plurality of stays 214) coupled to the receiving pawl may be in contact with a suprafascial surface 748 around the wound 744, as illustrated in FIG. 6C. The interlocking of the receiving pawl and the engaging ratchet within the inner channel 260 of the column 206 may cause the mechanical compression of the column within the wound 744, as illustrated in FIG. 6D. Further, the suprafascial biohybrid scaffold 218 and corresponding suprafascial plurality of stays 214 of the suprafascial extension may be fully radially expanded at this point. As a further result of this motion, portions of the wound plug 200 may be driven out of the implant chamber 532, and the implant chamber may be lifted off the suprafascial surface 748 to allow for unrestricted clearance of the suprafascial rivet head 204 and the column 206 into the wound 744. Further, three consecutive clicks may be heard and felt by a user to indicate that the wound plug is fully deployed.

In some embodiments, the post 300 may be twisted to break the post at the breakaway point 320 such that the engaging ratchet is separated from the post, as illustrated in FIG. 6D. In some embodiments, both an outer profile of the post and an inner profile of the rod cavity have a cruciate shape, such that post is prevented from rotating within the rod cavity (e.g., to facilitate the application of torque to a breakaway point of the post when the rod is twisted).

In some embodiments, any or all components of the apparatus may be assembled within any disposable or non-disposable surgical gun or applier, and these may be designed with automatic reloads of the wound plug, either within the apparatus or applied separately to it, for sequential and repetitive deployment.

In some embodiments, the wound plug 200 may afford stabilization and/or healing of any type of penetrating wound caused by traumatically impaling the fascia anywhere on the body. The wound plug may appropriately address various types of hernias within the abdominal wall. The wound plug's postoperative antimicrobial benefits may be feasible for the primary closure of fistulated tracks or other types of reoccurring infected wounds. The wound plug's antimicrobial and anesthetic advantages, as well as its ability for completely healing these chronic wounds, may eliminate lengthy secondary or tertiary healing attempts, which often succumb to re-infection and reoccurrence. By application of the apparatus 100, the wound plug 200 may be considered possible for closing the abdominal fascial defect of a stoma (i.e., colostomy) following surgical re-anastomosis of the bowel. The wound plug may close any fascial defect following the removal of any large drainage tube, surgical tube, or port that is at high risk for herniation or poor wound healing, in general.

In some embodiments, the wound plug 200 may be made to address any length or shape of fascial incision anywhere on the body, with or without the incorporation of sutures for reinforcement. For example, the wound plug may be in a more rectangular and linear profile, thus allowing for its repetitive and sequential application along the fascial incision line. Fascial incisions may include, but are not limited to, any region of the abdomen (i.e., midline or transverse laparotomy incisions), any location on the extremities (i.e., incisions for repairing fractured bones or joint replacement arthroplasties), posterior or flank regions of the torso (i.e., spinal or kidney incisions), or fascial planes covering the anterior, lateral, or posterior areas of the chest wall (i.e., video assisted open thoracostomy port-site wounds or thoracostomy incisions).

In some embodiments, the apparatus 100 may be designed to incorporate a fiber optic cable with an optical lens to allow for direct visualization of the subcutaneous tunnel and anterior abdominal fascia during its insertion and deployment within the wound. Although embodiments of the disclosure are described without requirement of a pneumoperitoneum, intra-abdominal telescopic lens, or any other instrumentation, the apparatus may be used in conjunction with such devices.

In some embodiments, the apparatus 100 may further include one or more elements to enhance light (or visual), auditory, or palpatory sensations when the rim of the shield 500 reaches the wound in the fascia 746 and/or as confirmation of accurate completion of other various steps during deployment. For example, a rim or lip 534 of the shield 500 may further include a touch-sensitive surface (mechanical, capacitive, and/or resistive, among other possibilities) to confirm that the rim has reached the wound in the fascia. Further, an audible sound may confirm the subfascial rivet head's placement below the fascia, and a light sensor may confirm engagement of the suprafascial and subfascial rivet heads (or any combination of sensor feedback).

In some embodiments, the apparatus 100 may further include a button-type retaining pin (either spring or manually designed) which, by virtue of its configuration, could function to lock and unlock the post 300. Once this retaining pin is pushed in to become flush with an external wall of the shield 500, a grooved configuration would release only the post 300, allowing its downward movement for deploying the subfascial rivet head 202.

In this embodiment, the alignment pin 600 can interlock the actuator rod 400 and shield 500 together prior to their deployment. After a user pushes the button of the retaining pin forward (toward the shield 500), the post 300 is released and may slide down as previously described. When the user pulls the post 300 upward in order to palpate the subfascial tissue 750, the retaining pin of the post may be pulled back toward the operator, out of its hole, until it engages the post in its locked configuration. Following the aforementioned activity of the post's retaining pin, the alignment pin 600 can be pulled out to release the rod 400 and the shield 500 for their deployment of the suprafascial rivet head 204. Naturally, with regards to this alternative, the profiles of the rod 400 and shield 500 would need to incorporate some sort of detent/horizontal slots or grooves to allow for their deployment activities over and alongside the presence of this stationary retaining pin. Such a configuration may allow for a more controlled and sequential release of the elements incorporated within the apparatus 100, freeing the user from needing to hold the post 300 stationary during the activation of the rod 400 and shield 500.

Additional Embodiments

Figures 8A, 8B:
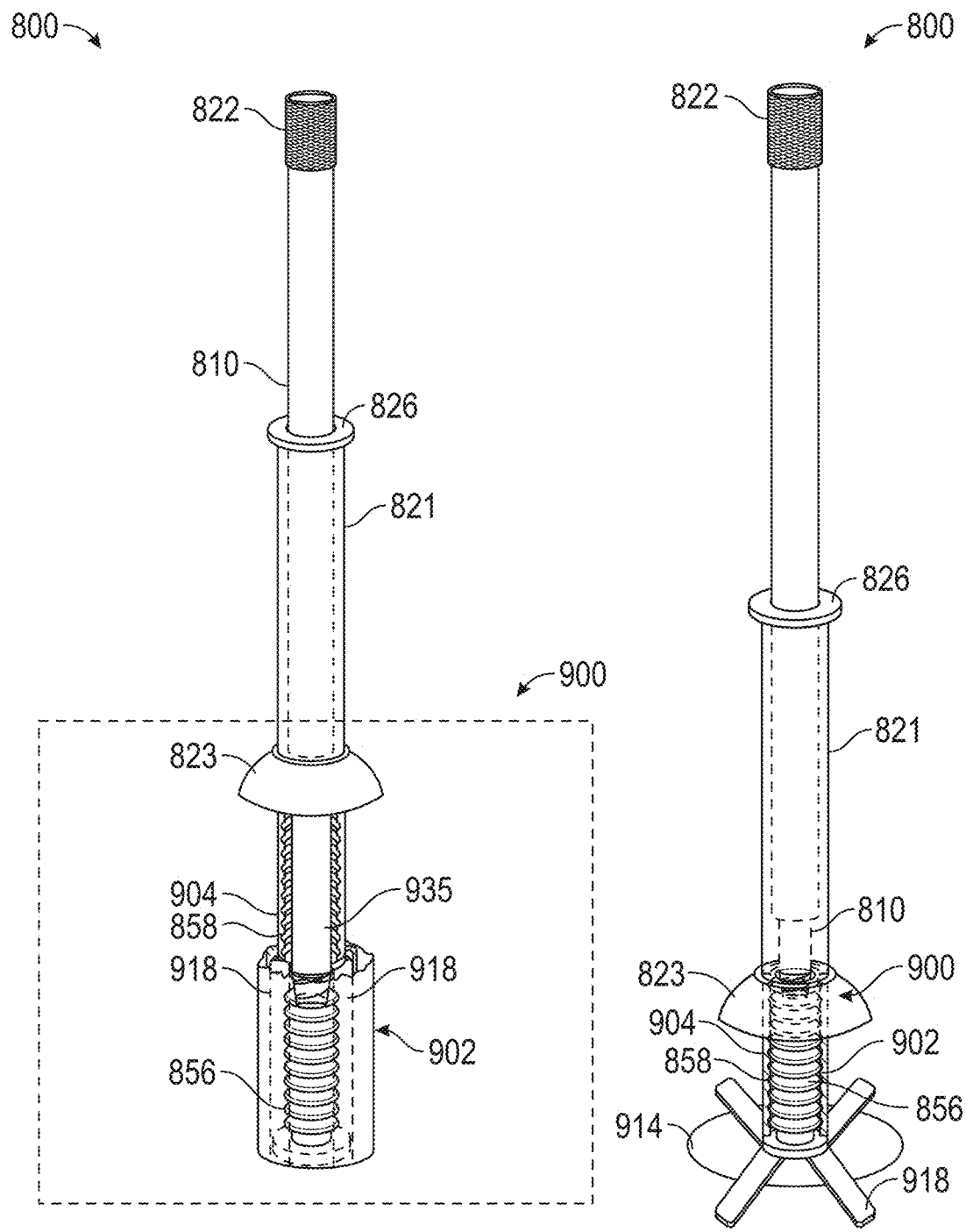
FIGS. 8A-8B illustrate a wound closure apparatus including wound plug according to embodiments of the disclosure.

FIG. 8A illustrates a wound closure apparatus 800 and wound plug 900 in an assembled configuration according to embodiments of the disclosure. The apparatus 800 may be a self-contained device for delivery and deployment of a tissue engineered wound plug 900 that can secure fascial closure of wounds. The wounds can be laparoscopic port-site wounds, fistulas, sinus tract wounds, traumatic wounds or the like. FIG. 8B illustrates a wound closure apparatus 800 and wound plug 900 in a deployed configuration according to embodiments of the disclosure.

Figure 9A:
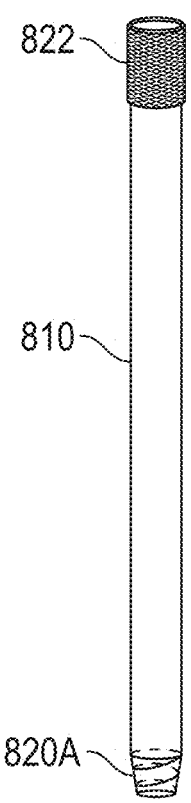
FIG. 9A illustrates a post according to embodiments of the disclosure.

The apparatus 800 may include a post 810 and a rod 821 for delivery and deployment of the wound plug 900. In some embodiments, the apparatus 800 may exclude a shield and an alignment pin (discussed above). FIG. 9A illustrates a post according to embodiments of the disclosure. The post 810 may include a coupling attachment 820A at a first end of the post and a handle 822 disposed at a second end. The coupling attachment 820A may be configured to temporarily attach to the wound plug 900. The handle 822 of the post 810 may be knurled and cylindrical. In some embodiments, the handle 822 may be profiled in different shapes which include, but are not limited to, a round, flat plate or disc, T-handle, thumb plate, ball, bulb, laterally contoured projections, finger-ring holes, diamond, ribbed finger grip, a rod-like handle and the like.

In some embodiments, the shaft of the post 810 may be circular and smooth. In some embodiments, the post may be formed in other non-cruciate shapes, such as geometric shapes like a triangle, diamond, a simple round or oval profile, a semi-circle shape, etc. In some embodiments, the post may be formed in a cruciate shape. Moreover, one or more of the four cruciate cross-arms may be added to or removed from the cruciate profile, thus allowing for a variety of shapes which include, but are not limited to, one cross-arm projection, two cross-arms similar to a dumb-bell shape, three cross-arms like a rounded three-leaf clover or a pointed triangular shape, a diamond shape, or multiple rounded or pointed projections as seen in various flower or star-like profiles. In some embodiments, the post 810 may exclude an alignment pinhole.

Figure 9B:
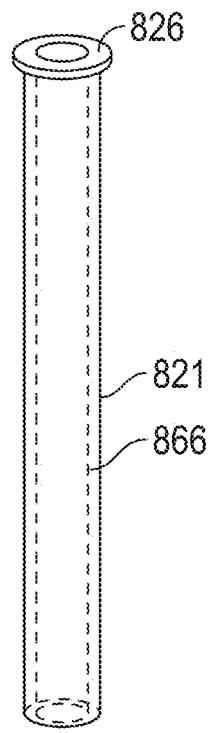
FIG. 9B illustrates a rod according to embodiments of the disclosure.

FIG. 9B illustrates a rod 821 according to embodiments of the present disclosure. The rod 821 may have a rod cavity 866 through which the post 810 is positioned. Thus, the post 810 and the rod 821 can form an apparatus 800 for delivery and deployment of the wound plug 900. In an assembled configuration, a first end of the rod 821 may be in contact with a first end of the wound plug 900 as shown in FIG. 8A. A second end of the rod 821 may include a plate 826. The plate 826 may act as a handle for the rod, thereby allowing a user to more easily manipulate the rod 821.

Figure 9C:
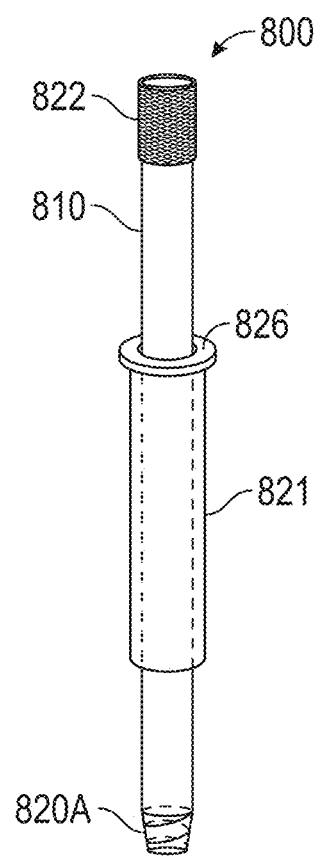
FIG. 9C illustrates a wound closure apparatus according to embodiments of the disclosure.

Referring to FIG. 9C, the post 810 and the rod 821 may reside at different radial levels in the apparatus 800. The post 810 may serve as an axis that is vertical and innermost to which the components of the apparatus 800 and wound plug 900 may be collectively aligned and integrated for deployment. For example, the alignment of the cannulated components of the rod 821 and wound plug 900, e.g., suprafascial rivet head 204, can create a common passageway through which portions of the post 810 can move for deployment of the wound plug 900.

The post 810 may be located in the core of the apparatus 800 and may be the longest of the components, with its handle 822 rising higher than the other components. Referring again to FIG. 8A, in some embodiments, the plate 826 of the rod 821 may be positioned at one end approximately midway between the handle 822 and the subfascial rivet head 902 when the apparatus 800 is coupled to the wound plug 900, i.e., when coupling attachment 820A of the post 810 is coupled to the breakaway connection 820B of subfascial rivet head 902 described in further detail with respect to FIGS. 11A-11C.

The shaft of the rod 821 may be non-cruciate and smooth to correspond to the shaft of the post 810. For example, the interior of the rod 821 may be smooth and configured to receive the post 810. If the shaft of the post 810 has a cruciate shape, the shaft of the rod 821 would similarly have a cruciate shape. The rod cavity 866 may facilitate the vertical stability and movement of the post 810 before, during, and after deployment of the wound plug 900. In some embodiments, the rod 821 may not include an alignment pinhole.

In some embodiments, the post 810, the rod 821, or both may include rigid materials comprising elements (e.g., the elements that will not be implanted within the body) that may be fabricated from non-critical, bio-safe materials. In some embodiments, portions of the post 810, rod 821, or both may include a flexible or semi-flexible material that can allow the flexible portions to follow the course of a tract, such as a fistulated tract.

Figure 10A:
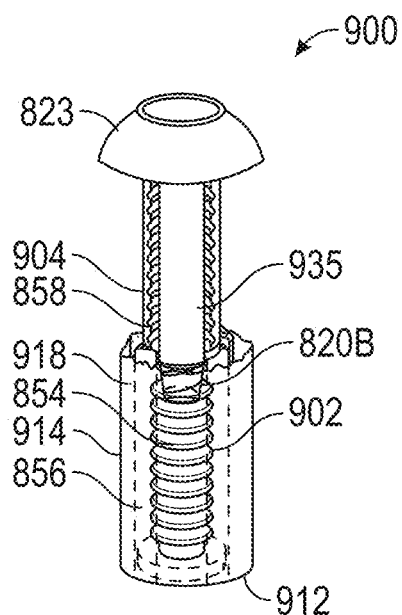
FIG. 10A illustrates a wound plug according to embodiments of the disclosure.

FIG. 10A illustrates a wound plug 900 in according to embodiments of the present disclosure. In some embodiments, the wound plug 900 may be one piece that includes a first portion 904 molded to a second portion 902. The first portion 904 may extend from a first, proximate end of the wound plug to a breakaway connection 920B. In some embodiments, first portion 904 may correspond to a suprafascial rivet head. The second portion may extend from a second, distal end or base 912 of the wound plug to the breakaway connection 920B. The second portion may include the breakaway connection 920B. In some embodiments, the second portion 902 may correspond to a subfascial rivet head. According to some embodiments, the wound plug 900 may not include a compressible column.

Figure 10B:
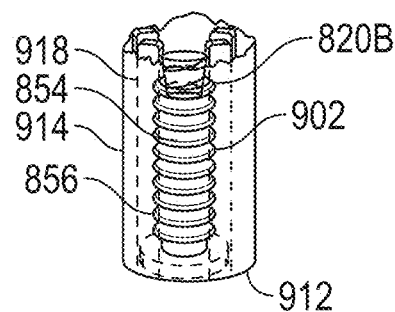
FIG. 10B illustrates a subfasical rivet head according to embodiments of the disclosure.

FIG. 10B is a second portion or subfascial rivet head 902 of the wound plug 900 according to embodiments of the present disclosure. The subfascial rivet head 902 may include a body 854 having a base 912 located at the second end of the wound plug opposite a breakaway connection 820B. The breakaway connection 820B is configured to receive the coupling attachment 820A of the post 810. In some embodiments, the body 854 of the subfascial rivet head 902 may include a plurality of annular flanges 856. The plurality of annular flanges 856 may extend from the base 812 to the breakaway connection 820B. The plurality of annular flanges 856 may allow the subfascial rivet head 902 to act as a ratchet when engaging with the suprafascial rivet head 904. In other words, the engagement of annular flanges 856 and 858 permit movement in one direction.

The subfascial rivet head 902 may also include at least one stay 918 connected to the subfascial rivet head 902 at the base 812. As illustrated in FIG. 10B, the subfascial rivet head 902 includes a plurality of stays 918. The plurality of stays 918 may be fabricated using shape memory properties, allowing for multiple different configurations during the implant's surgical application. Prior to deployment, the plurality of stays 918 may project at 90° angles from an outer perimeter of the subfascial rivet head 902. Once the rivet head 902 is deployed, the shape memory properties of the plurality of stays 918 can be affected by the body's temperature and/or pH relative to a pre-determined time interval also inherent in their chemical properties. These physical and biological properties can cause each stay 918 to automatically deploy into a full radial expansion.

The subfascial rivet head 902 may include a biohybrid scaffold 914. For example, in some embodiments, the biohybrid scaffold may be fully perforated with micro-perorations to allow for the native tissue integration, takeover, and eventual destruction of the scaffold in order for natural materials and tissue to fill the void in the wound. In some embodiments, the biohybrid scaffold 914 may cover and embed portions of the subfascial rivet head 902. In some embodiments, the biohybrid scaffold 914 may cover the stay or plurality of stays 918.

FIGS. 10C-10F illustrate embodiments of the suprafascial rivet head 904 according to embodiments of the present disclosure. The suprafascial rivet head 904 may comprise a hollow receiving pawl configured to engage with an engaging ratchet of the subfascial rivet head 902. For example, the receiving pawl may include a number of reciprocal annular grooves 858 configured within its interior that correspond to a number of flanges 856 on the exterior of the subfasical rivet head 902. Further, the suprafascial rivet head 904 may be configured with a channel 935 to allow the post 810 to pass through its hollow core. In some embodiments, engagement of the subfascial and the suprafascial rivet heads 902 and 904, respectively, may be confirmed by audible clicks synchronized with tactile sensations.

Figure 10C:
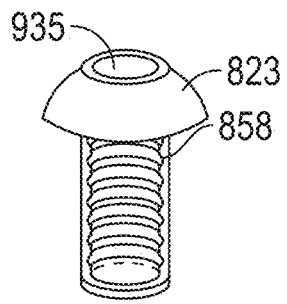
FIGS. 10C-10F illustrates a suprafascial rivet head according to embodiments of the disclosure.

The suprafascial rivet head 204 may also include at least one suprafascial extension disposed on a first end of the wound plug. The extension may abut the first end of the rod 821 when the apparatus 800 and wound plug 900 are in an assembled configuration, e.g., shown in FIGS. 8A-8B. Referring specifically to FIG. 10C, the shape of the suprafascial extension is a cup 823. The suprafascial extension cup 823 may be any size, shape, thickness, or configuration. For example, the suprafascial extension cup 823 may project at an angle (e.g. 80 or 90 degrees, etc.) from an outer perimeter of the suprafascial rivet head 904.

Like the plurality of stays 918 of the subfascial rivet head 902, the suprafascial extension cup 823 may be developed from either biological or chemical polymers. For example, the suprafascial extension cup 823 may be electrospun or dip coated with an absorbable chemical polymer to enhance its full radial expansion on the anterior abdominal fascia. Once the suprafascial rivet head 904 is deployed, the shape memory properties of the suprafascial extension cup 823 may be affected by the body's temperature and/or pH relative to a pre-determined time interval also inherent in their chemical properties. These physical and biological properties may cause the sides of the suprafascial extension cup 823 to automatically deploy into a full radial expansion. In some embodiments, the suprafascial extension cup may serve as a biohybrid scaffold. For example, the suprafascial extension cup 823 may include micro-perforations to allow for native tissue ingrowth and takeover.

Figure 10D:
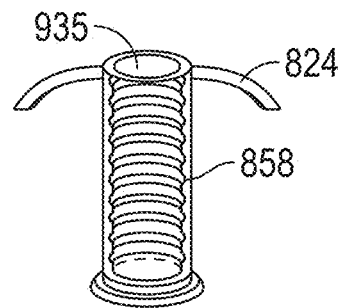
Figure 10E:
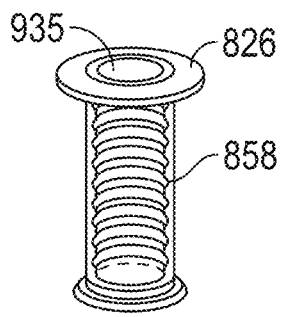
Figure 10F:
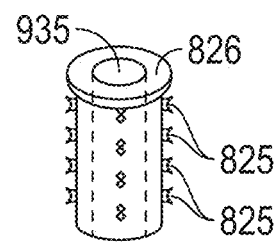

Referring to FIG. 10D, the suprafascial rivet head 904 may include a suprafascial extension in the shape of stays 824. In some embodiments, the suprafascial rivet head 904 may include one large suprafascial stay-extension 824 or multiple suprafascial stay-extensions 824 (not shown). In some embodiments, as depicted in FIGS. 10E and 10F, the suprafascial rivet head 904 may include a suprafascial extension plate 826. The variations of the suprafascial extensions in FIGS. 10D-10F may have the same physical properties and chemical make-up as described with respect to suprafascial extension cup 823.

In some embodiments, as seen in FIG. 10F, an outer surface of the suprafascial rivet head 904 may include a plurality of external polymer barbs 825. External barbs 825 may anchor the suprafascial rivet head 904 to the native tissues of the wound. Specifically, when the wound plug 900 is inserted into a wound and the post 810 is removed, the barbs 825 may catch the tissue of the wound, thereby anchoring the deployed wound plug in the wound. The barbs 825 may allow the wound plug 900 to be embedded in wounds in a variety of tissue types. For example, the barbs 825 can fasten the suprafascial rivet head 904 within the space of the wound and even into the blind-end of the sinus tract.

In some examples, the barbs 825 can be circumferentially oriented features that project from the interior of the wound plug 900. In some embodiments, the barbs 825 can surround the subfascial rivet head 904 of the wound plug 900 in a spiral orientation (not shown). In some embodiments, the barbs 825 may be unidirectional, having features pointing in the same directions such as towards the second end of the wound plug 900. In some embodiments, as illustrated in FIG. 10F, the barbs 825 may be positioned bi-directional or multi-directional.

The wound plug 900 (including the barbs 825) may be composed of natural polymers or copolymers like chitosan, gelatin, alginate, collagen and/or other wound healing promoters; as well as synthetic polymers or copolymers such as PGA, PLA, PDO, PCL, PLLA, or synthetic copolymers like PLGA. The possibilities for such fabrication techniques may include but are not limited to polymeric blends, dip coating, adhesive layering, copolymerization, grafting, homogeneous mixtures, and/or electrospinning for creating a biosynthetic composite material. In some embodiments, the wound plug can comprise one or more surgical dressing materials such as gauze, silicon, rubber, etc.

Figure 11C:
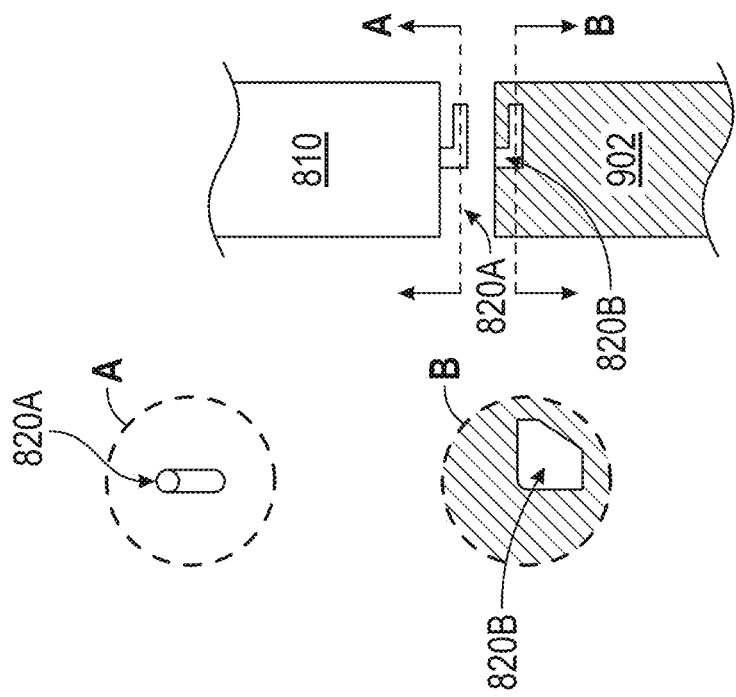
FIGS. 11A-11C illustrate a coupling mechanism according to embodiments of the disclosure.
Figure 11B:
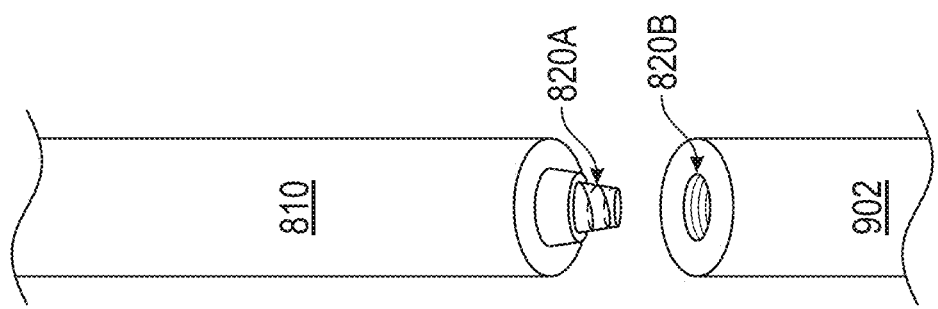
Figure 11A:
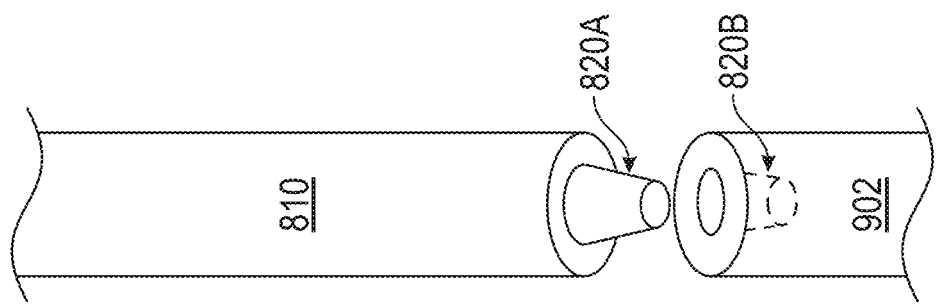

FIGS. 11A-11C illustrate a number of variations of the coupling attachment 820A and the breakaway connection 820B used to couple the apparatus 800 with the wound plug 900. Typically, the coupling attachment 820A will be a male (i.e., protruding) component. This may allow the post 810 to more easily navigate the cannulate cavities of rod 821 and suprafascial rivet head 904 to mate with the corresponding female breakaway connection 820B. In some embodiments, the connection between coupling attachment 820A and the breakaway connection 820B may provide vertical stability and strength to the apparatus 800 and wound plug 900 assembly, thereby allowing the device to resist compression or elongation during insertion and deployment.

Referring to FIG. 11A, the coupling attachment 820A and the breakaway connection 820B may be configured to have a press-fit. In the press-fit configuration, the dimensions of the coupling attachment 820A will be configured to overlap with the dimensions of the breakaway connection 820B. In this manner, an interference fit results when the post 810 and the subfascial rivet head 902 of the wound plug 900 are pressed together.

FIG. 11B illustrates a luer-lock configuration. In the luer-lock configuration, the post 810 is advanced through the interior cannula 866 of the suprafasical rivet head 904 until the coupling attachment 820A abuts the breakaway connection 820B. The post 810 may then be rotated in order to have the coupling attachment 820A rotate and lock into the breakaway connection 820B. In other embodiments, the post 810 may be further pressed in order to have the coupling attachment 820A click and lock into the breakaway connection 820B.

FIG. 11C illustrates a cam-lock configuration. In the cam-lock configuration, the coupling attachment 820A may include a cam protrusion. The cam protrusion 820A may be positioned in a corresponding keyhole shaped breakaway connection 820B disposed on the subfascial rivet head 902. Once in the keyhole shaped breakaway connection 820B, the cam protrusion can be rotated to lock the post 810 of the apparatus 800 to the wound plug 900. Although a specific cam-lock and keyhole shape is illustrated in FIG. 11D, for example, at cross-sections A and B, one skilled in the art will understand that a variety of cam-lock and keyhole shapes may be used without departing from the scope of this disclosure.

According to embodiments of this disclosure, despite the particular variant (pressfit, luer-lock, or cam-lock), the post 810 may be rotated to release or unscrew and detach coupling attachment 820A from the breakaway connection 820B. By this described detachment, the non-critical elements of the apparatus 800 (e.g., the post 810 and rod 821) are separated from the wound plug 900, and removed from the wound.

In some embodiments, the temporary attachment between the coupling attachment 820A and the breakaway connection 820B may be designed to be pre-attached and permanently severed by a physical means such as a ballpoint pin snap release (the button would be constructed in the handle 822), pull, twist, or the like, instead of the application as discussed previously above. Additionally, since many components of the apparatus 800 may respond to the body's pH and/or temperature, the breakaway connection 820B of the subfascial rivet head 902 may be fabricated with chemical properties that are engineered to release within a specific period of time shortly after deploying the wound plug.

The assembly of the apparatus 800 and wound plug 900 may be completed at a sterile operating room table prior to inserting and deploying it within a port site wound, or fistula/sinus track. Specifically, the post 810 may be positioned within the cavity 866 of the rod 821. The post 810 may extend through the rod cavity 866 and into the wound plug 900, where connecting attachment 820A can be coupled to the breakaway connection 820B. In some embodiments, a tactile sensation or audible response may indicate that the apparatus 800 and wound plug 900 are coupled in the assembled configuration.

Figure 12A:
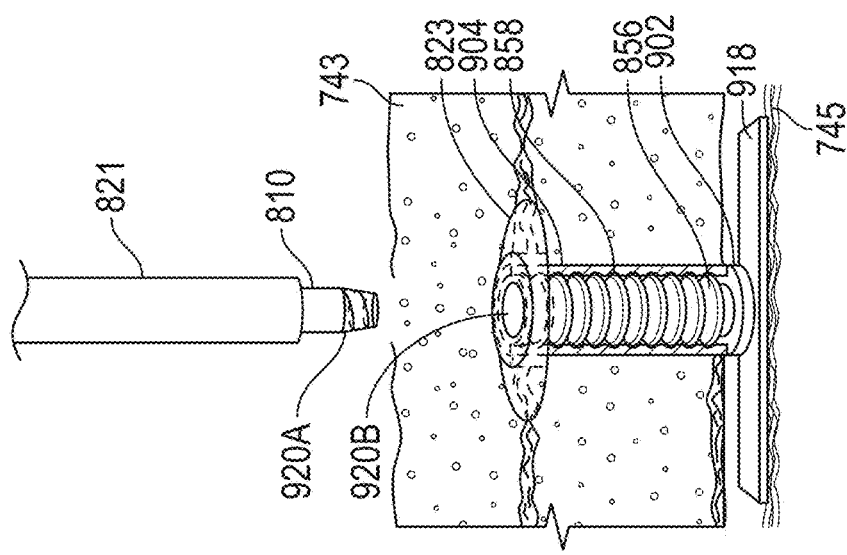
FIGS. 12A-12C illustrate a wound closure apparatus during stages of deployment of the wound plug according to embodiments of the disclosure.
Figure 12B:
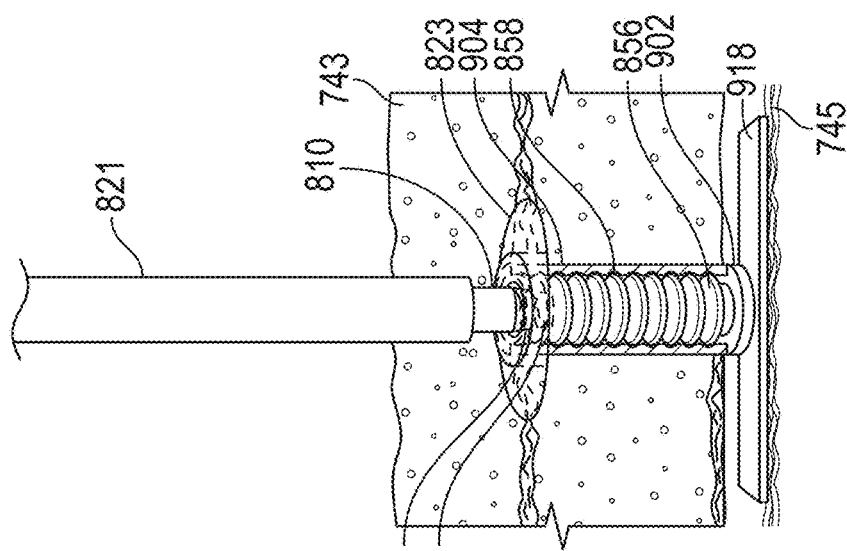
Figure 12C:
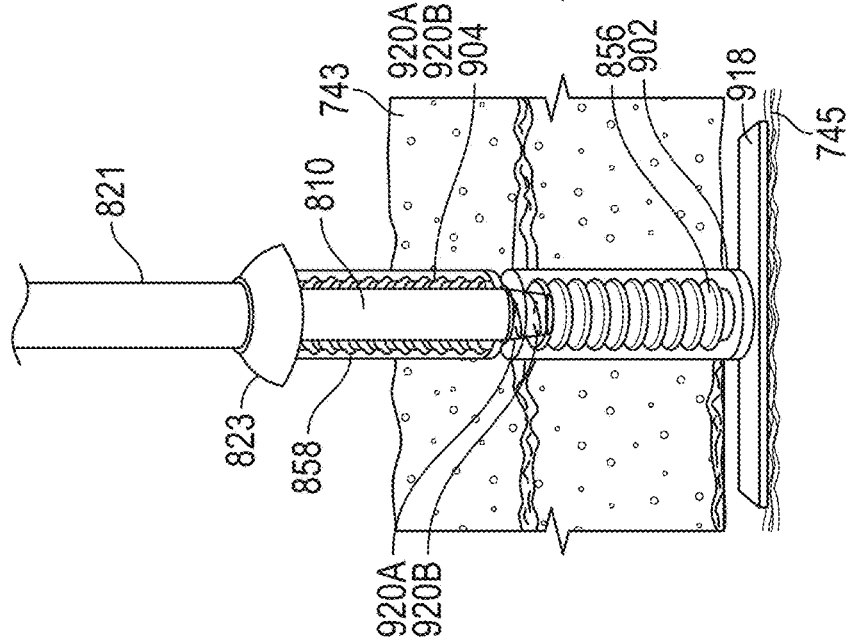
Figure 13:
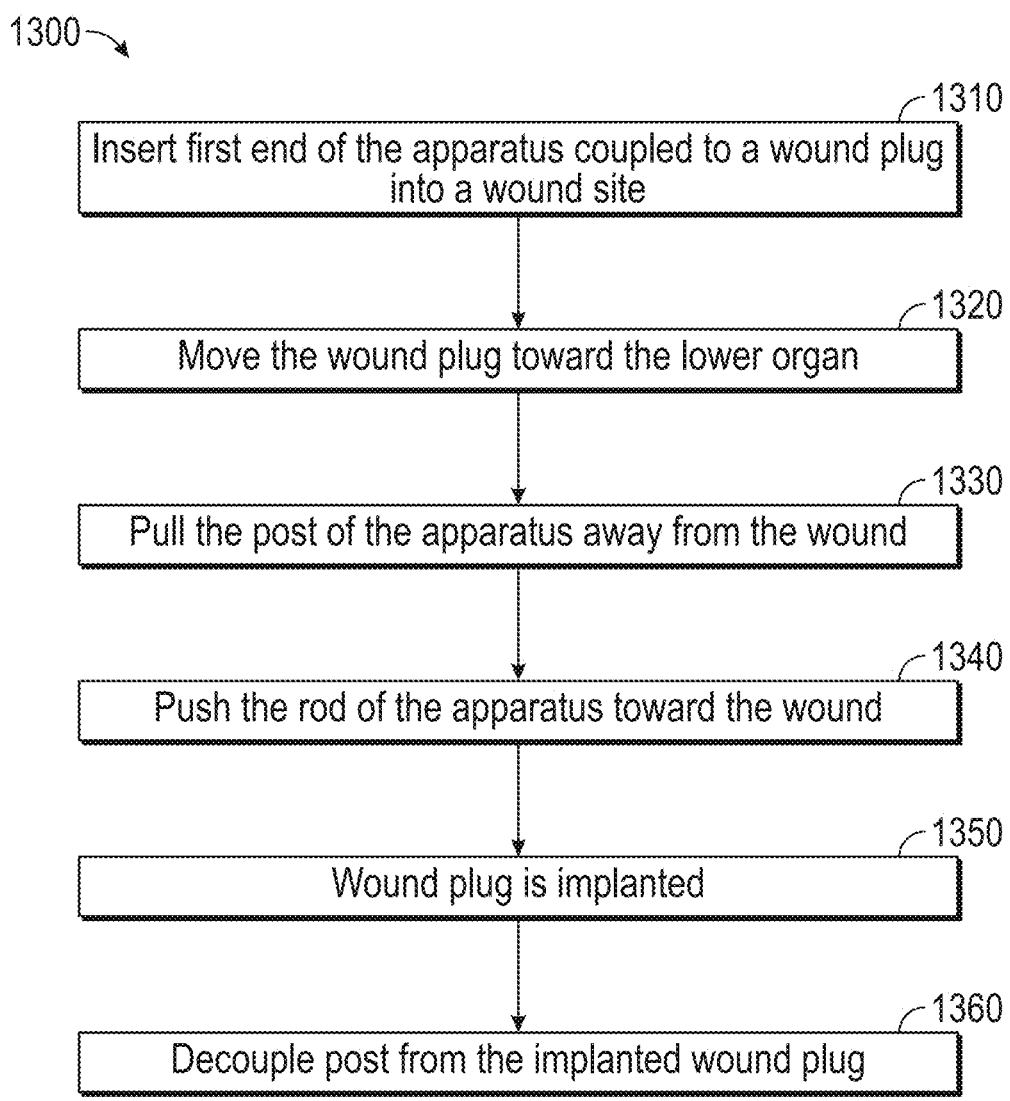
FIG. 13 is a flowchart of a method of deploying a wound plug according to embodiments of the disclosure.

Once the apparatus 800 and wound plug are assembled, e.g., as shown in FIG. 8, the apparatus may be used to deploy the wound plug 900 in a wound site. FIGS. 12A-12C illustrates the deployment of a wound plug according to embodiments of the disclosure. FIG. 13 is a block diagram of a method for deploying a wound plug according to embodiments of the disclosure. The first end of the apparatus 800 can be inserted (step 1310) into a wound site, e.g., near upper organ 743. As shown in FIG. 12A, the wound plug 900 may be moved (step 1320) to a position above lower organ 745. The moving may be performed by gripping the handle (not shown) of the post and maneuvering the wound plug 900 through the wound hole such that the plurality of stays 918 and the biohybrid scaffold located at the first end the wound plug 900 can open in full radial expansion, thereby occluding the wound hole above lower organ 745.

The wound plug may be deployed or implanted in the wound by raising (step 1330) the post 810 up and away from the wound site. For example, the handle 822 may be raised upward. This movement may cause the subfascial rivet head 902 and suprafascial rivet head 904 to interlock. Specifically, the subfascial rivet head 902 coupled to the connecting attachment 820A may move upward such that the plurality of flanges 856 disposed on the subfascial rivet head engage with the plurality of ridges 858 disposed on the suprafascial rivet head 904. The interlocking of the plurality of flanges 856 and the plurality of ridges 858 may create a tactile sensation, which notifies a user that the subfascial rivet head 902 and suprafascial rivet head 904 are interlocked. In some embodiments there will also be an audio cue that accompanies the tactile sensation. In some embodiments the engagement of the plurality of flanges 856 the plurality of ridges 858 acts as a ratchet mechanism, permitting relative movement of the subfascial rivet head 902 in a single direction.

Once the subfascial rivet head 902 and suprafascial rivet head 904 are engaged, the user may push (step 1340) the rod 821 downward toward the wound site to expand the suprafascial extension, e.g., cup 823, radially outward below upper organ 743. In some embodiments, the user may push the plate 826 downward while simultaneously pulling the handle 822 upward to ensure proper placement of the wound plug 900 during deployment. Thus, the wound plug is fully implanted (1350) as shown in FIG. 12B.

Once the wound plug is implanted, the apparatus 800 may be decoupled (Step 1360) from the wound plug 900 as shown in FIG. 12C. For example, the user may rotate and pull the post 810 in order to decouple the connecting attachment 820A from the breakaway connection 820B. The detachment of the connecting attachment 820A from the breakaway connection 820B may be confirmed by a tactile sensation and in some embodiments, audible clicks.

Once the post 810 and the rod 821 are separated from the wound plug and removed from the wound, their byproducts may be safely discarded as environmentally friendly, non-toxic wastes. In some embodiments, the post 810 and the rod 821 can be reloaded and reused multiple times. For example, the apparatus 800 with the same post 810 and rod 821 may be reassembled to be reused with a second wound plug 900. In some embodiments, the apparatus 800 may be cleaned and sterilized prior to assembling the apparatus 800 with the second wound plug 900. Alternatively, the same post 810 and a different rod, or a different post 810 and the same rod 821, may be used for the second wound plug 900.

Rivet Head Extension with a Living Hinge

Figure 14A:
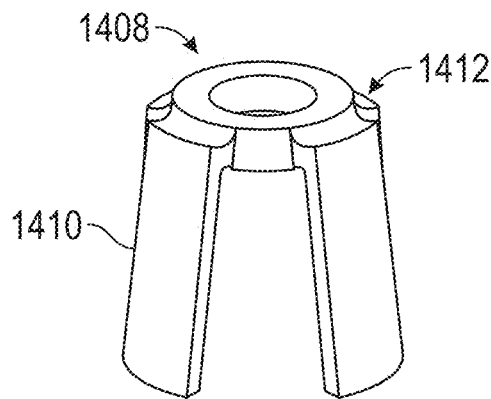
FIGS. 14A-14F illustrate stays of a wound plug according to embodiments of the disclosure.
Figure 14B:
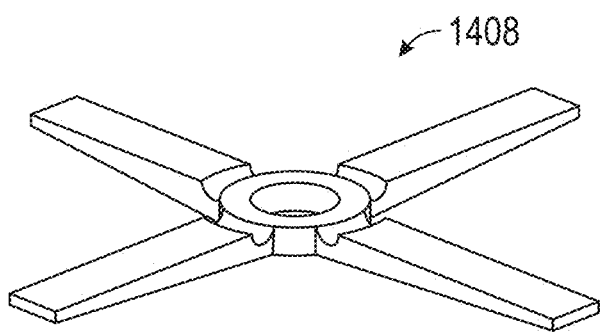

FIGS. 14A-14G illustrate embodiments of the rivet head extensions including a living hinge according to embodiments of this disclosure. For example, each suprafascial rivet head extension 1408 may include a plurality of stays 1410 attached to the extension 1408 with a living hinge. The living hinge may be formed by having a narrowing of the mass where the plurality of stays 1410 attaches to the extension 1408. For example, as seen in FIG. 14A, the living hinge 1412 be formed by having an oval indentation at the attachment point. FIG. 14B illustrates the extension 1408 with living hinges 1412 in a fully extended configuration. Prior to deployment the each of the plurality of stays 1410 may project at a 90° angle from the outer perimeter of each extension 1408, offset relative to each other at a 45° angle of arc. After deployment, the extension 1408 and the plurality of stays 1410 may remain substantially flat.

Figure 14C:
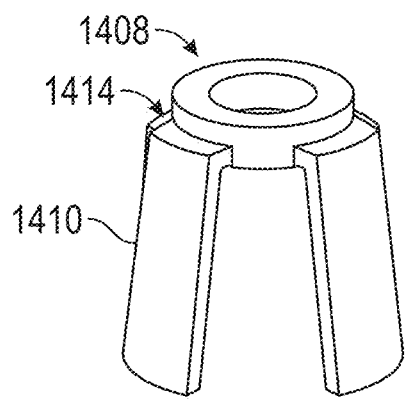
Figure 14D:
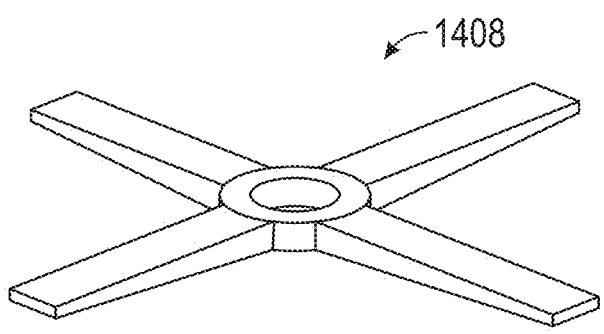
Figure 14E:
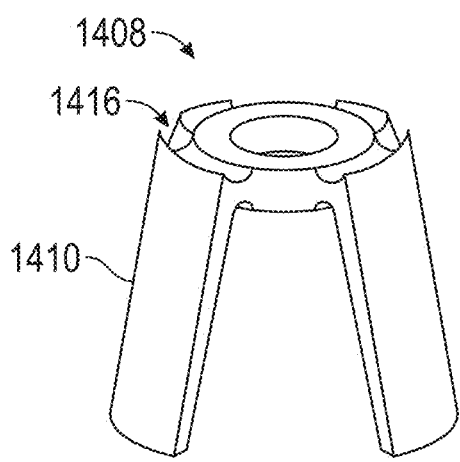
Figure 14F:
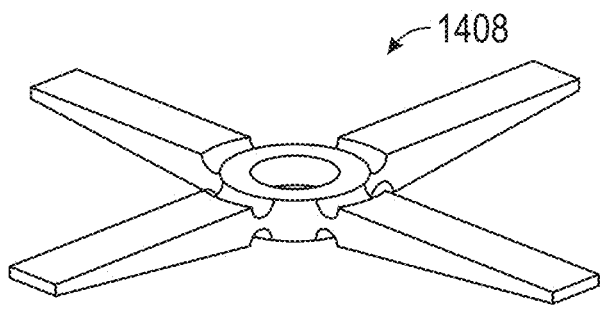

FIG. 14C illustrates an embodiment where the living hinge 1414 is formed by having a square indentation at the attachment point to the extension 1408. FIG. 14D illustrates the extension 1408 with living hinges 1414 in a fully extended configuration. FIG. 14E illustrates another embodiment where the living hinge 1416 is formed by having an inner and outer oval indentation where the plurality of stays 1410 attaches to the extension. FIG. 14F illustrates the extension 1408 with living hinges 1416 in a fully extended configuration. One skilled in the art will understand that the type of living hinge is not intended to be a limitation on this disclosure. For example, in some embodiments, the living hinge may include a manufactured fold. In some embodiments, the living hinge may include a c-shaped pin.

Embodiments of the extensions 1408 with living hinges may otherwise be substantially similar to the extensions 208 described with respect to FIGS. 2E-2F. For example, the extensions 1408 may be composed of natural polymers or copolymers like chitosan, gelatin, alginate, collagen and/or other wound healing promoters; as well as synthetic polymers or copolymers such as PGA, PLA, PDO, PCL, PLLA, or synthetic copolymers like PLGA. As with the extensions 208, in some examples, the number of stays 1410 on each rivet head can be chosen relative to the size of each rivet head extension 1408, as well as to the weight and size of their associated biohybrid scaffold. The cross sectional profile of each stay may be tapered on one side and non-tapered (e.g., flat) on the opposing side. This profile can be consistent throughout the length of each stay, terminating into a blunt-point end.

Although the living hinge has only been illustrated with respect to the suprafascial rivet head extension 1408, one skilled in the art will understand that the subfascial rivet head extension may also include stays with a living hinge according to embodiments of the present disclosure.

Additional Subfascial Rivet-Head Embodiments

Figure 15A:
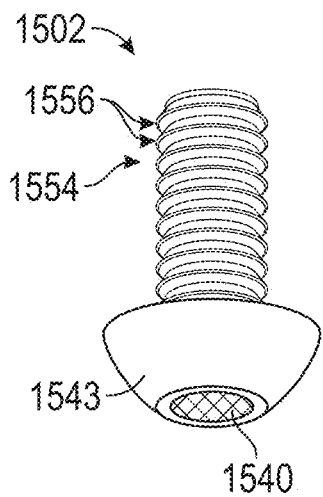
FIGS. 15A-15C illustrate a subfascial rivet head according to embodiments of the disclosure.

In some embodiments, the subfascial rivet head of the wound plug may be a mirror image of the suprafascial rivet head. For example, with reference to FIGS. 15A-15C and 10C-10F, the subfascial rivet head 1502 may include at least one subfascial extension that is a mirror image of a corresponding suprafascial extension located on the suprafascial rivet head 1004. For example FIG. 15A illustrates a subfascial rivet head 1502 according to embodiments of this disclosure that corresponds to the suprafascial rivet head 1004 of FIG. 10C. The subfascial rivet head 1502 may include at least one subfascial extension in the shape of a cup 1543. The suprafascial extension cup 1543 may be any size, shape, thickness, or configuration. For example, the suprafascial extension cup 1543 may project at an angle (e.g. 80 or 90 degrees, etc.) from an outer perimeter of the subfascial rivet head 1502. The subfascial extension cup 1543 may correspond in size and shape to a corresponding suprafascial extension cup (e.g., suprafascial extension cup 823 illustrated in FIG. 10C). An example of this configuration may be seen in FIG. 16A.

Referring to FIG. 15A, the subfascial rivet head may include an engaging ratchet 1554 with a plurality of flanges 1556 arranged circumferentially along the length of the engaging ratchet 1554. The plurality of flanges 1556 are configured to engage with the plurality of reciprocal annular grooves disposed on the interior of the suprafascial rivet head. In some embodiments, engagement of the subfascial and the suprafascial rivet heads may be confirmed by audible clicks synchronized with tactile sensations. In some embodiments, the engaging ratchet 1554 may include a channel that runs the length of the subfascial rivet head 1502. This channel may terminate in a biohybrid scaffold 1540 disposed at a second end of the subfascial rivet head 1502. The bio-hybrid scaffold 1540 may prevent the egress of any biogels or fluids disposed in the wound plug to the surrounding tissue.

Like the suprafascial extension cup 823 described above with respect to FIG. 10C, the subfascial extension cup 1543 may be developed from either biological or chemical polymers. For example, the subfascial extension cup 1543 may be electrospun or dip coated with an absorbable chemical polymer to enhance its full radial expansion on the anterior abdominal fascia. Once the subfascial rivet head 1502 is deployed, the shape memory properties of the subfascial extension cup 1543 may be affected by the body's temperature and/or pH relative to a pre-determined time interval also inherent in their chemical properties. These physical and biological properties may cause the sides of the subfascial extension cup 1543 to automatically deploy into a full radial expansion. In some embodiments, the subfascial extension cup may serve as a biohybrid scaffold. For example, the subfascial extension cup 1543 may include micro-perforations to allow for native tissue ingrowth and takeover.

Figure 15B:
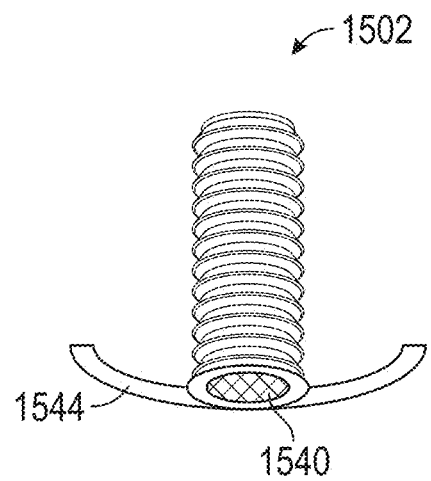

Referring to FIG. 15B, the subfascial rivet head 1502 may include a subfascial extension in the shape of stays 1544. In some embodiments, the subfascial rivet head 1502 may include one large subfascial stay-extension 1544 or multiple subfascial stay-extensions 1544. Much like the extension cup, the stays 1544 may have the same physical properties and chemical make-up as described with respect to the subfascial extension cup. For example, these physical and biological properties may cause the stay-extensions 1544 to automatically deploy into a full radial expansion.

Figure 15C:
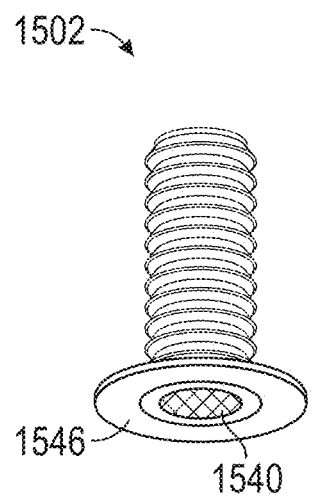

In some embodiments, as depicted in FIG. 15C, the subfascial rivet head 1502 may include a subfascial extension plate 1546. The variations of the subfascial plate may have the same physical properties and chemical make-up as described with respect to subfascial extension cup 1543.

Figure 16A:
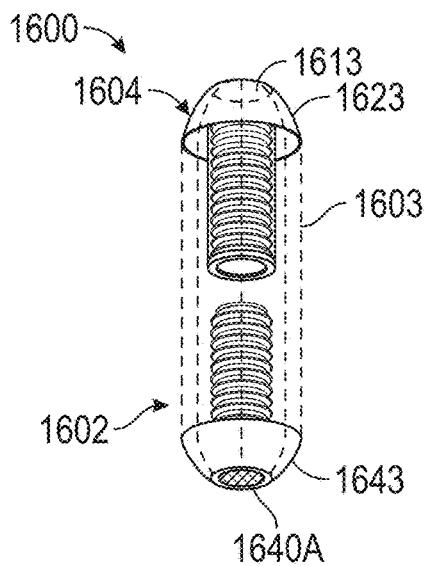
FIGS. 16A-16F illustrate a wound plug according to embodiments of the disclosure.
Figure 16B:
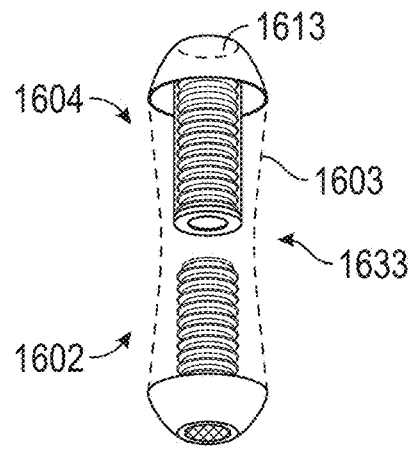

FIG. 16A illustrates a wound plug according to some embodiments including a subfascial rivet 1602 that mirrors the suprafascial rivet 1604. Specifically, as shown in FIG. 16, the suprafascial rivet 1604 with an extension cup 1623 mirrors the subfascial rivet 1602 with an extension cup 1643. One skilled in the art will understand that other embodiments of the wound plug are not limited to this configuration of subfascial and suprafascial rivet heads. For example, the subfascial rivet and suprafascial rivet may both include stays that are a mirror image of each other. In another embodiment, the subfascial rivet and suprafascial rivet may both include an extension plate that are a mirror image of each other. In another embodiment, the subfascial rivet and suprafascial rivet may both include a plurality of barbs that are a mirror image of each other.

Wound Plug with Bladder

Figure 16C:
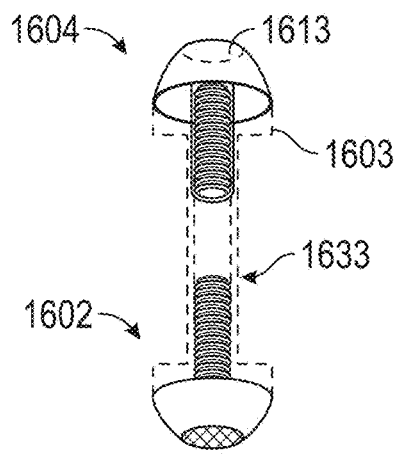
Figure 16D:
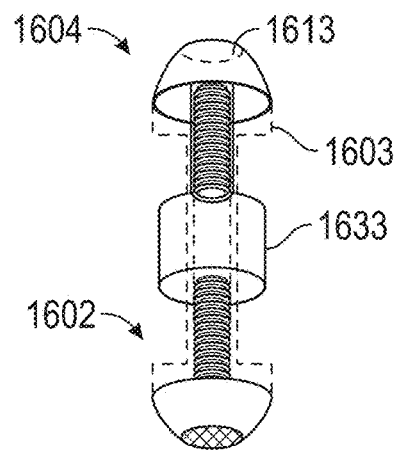

Referring to FIG. 16A, in some embodiments the wound plug may include a bladder 1603. The bladder 1603 may surround the body of the wound plug, e.g., the suprafascial rivet head 1604 and the subfascial rivet head 1602. The first end of the bladder 1603 may include a post-receiving opening 1613. In some embodiments, the post-receiving opening 1613 may include a one-way valve. The bladder 1603 may be formed into various shapes, including but not limited to, an oval (FIG. 16A), a dumbbell, an hourglass (FIG. 16B), and a spool (FIG. 16C-16D). In some embodiments the bladder 1603 may include a waist 1635 where the cross-section of the central portion of the bladder 1603 is narrower than the ends, e.g., the dumbbell, hourglass, and spool shapes. The waist 1635 may reduce pressure on the inside of the wound, and may prevent migration or dislodgment of the wound plug 1630 out of the port site wound. In some embodiments, the bladder 1603 may be shaped (e.g., by a factory or 3D printing) to have a narrow waist.

As seen in FIG. 16D, in some embodiments, the waist 1635 may be formed by positioning a thickened compressible band 1633 or ring around the central portion of the bladder 1603. In such an embodiment, bidirectional barbs may be located on an outer surface of the band 1633 to secure the wound plug 1630 into the wound site and prevent its migration. In other embodiments, the band 1633 may be formed from the same material used to create the bladder 1603. In other embodiments the waist may be narrowed by including an already manufactured and knotted down drawstringed tuff (not shown).

Figure 16E:
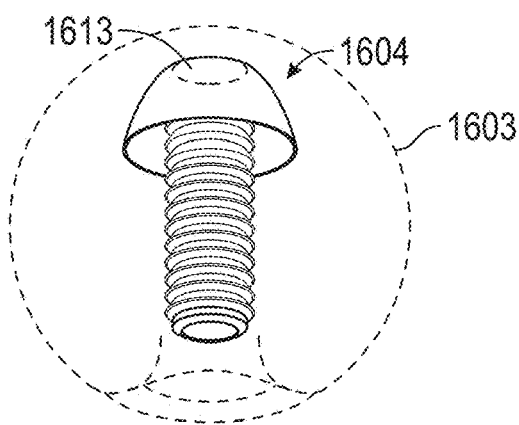
Figure 16F:
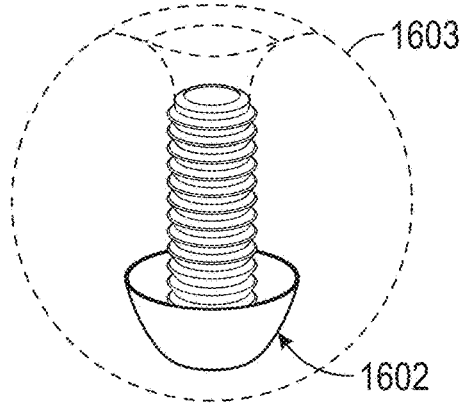

Referring to FIG. 16E, in some embodiments, the bladder 1603 may be fastened to just the suprafascial rivet head 1604, surrounding the receiving pawl. As shown in FIG. 16F, in some embodiments, the bladder 1603 may be fastened to the subfascial rivet head 1602, surrounding the flanges of the ratchet. Although depicted with a wound plug embodiment including an extension cup in FIGS. 16A-16F, one skilled in the art will understand that the bladder 1603 may be implemented with any of the extension configurations described above with respect to FIGS. 10C-10F and 15A-15C. e.g., a plate, stay, and/or barbs.

The post-receiving opening 1613 may allow the post to enter the wound plug 1600 and bladder 1603 unobstructed. Specifically, the post may pass through the suprafascial rivet head 1604 to mate with the subfascial rivet head 1602 as described above with respect to FIGS. 11A-11C. In some embodiments, the post received by the bladder may include a breakaway point as described above with respect to FIGS. 2C, 2D, 3A, and 3D. In embodiments where the subfascial rivet 1602 includes a channel, the post may pass through at least a portion of the subfascial rivet head 1602.

In some embodiments, a hydrogel or liquefied matrix may be provided to the bladder 1603 during deployment the wound plug 1600. For example, once the wound plug 1600 is deployed, hydrogel or fluid may be injected into the wound plug 1600. The bladder 1603 may prevent the immediate egress of the hydrogel or fluids from the wound plug 1600 into the wound site. As the bladder is filled with the hydrogel, the walls of the bladder 1603 may expand laterally into the wound site, as described in more detail below. Moreover, the soft nature of the bladder may feel more comfortable to the patient postoperatively.

In some embodiments, the bladder 1603 may be pressfit to at least one of the suprafascial rivet head 1604 and the subfascial rivet head 1602. In some embodiments, the subfascial and suprafascial rivet heads may be located within the bladder 1603, without being directly coupled to the bladder 1603. In some embodiments, the bladder may be 3D printed, press-molded, cut and sutured.

The bladders may be manufactured in various standardized sizes that correspond to the port size wound diameters (e.g., 5 mm, 8 mm, 10 mm, 12 mm, 14 mm). In other words, the outer diameter of the bladder may be approximately 5 mm, 8 mm, 10 mm, 12 mm, 14 mm. In some embodiments, the wound plug including the bladder may be manufactured in standardized lengths to accommodate variable thickness from the anterior fascia to the parietal peritoneum in different patients (e.g., children, adults, obese individuals). The standardized lengths may be in a range from about 3.5 mm to about 7.0 mm, depending on the size of the patient. The various bladder sizes may each correspond to a predetermined volume of liquefied matrix. In this way, a user will know the volume of fluid necessary to fill the bladder. According to some embodiments, when the wound plug is inserted into a wound, the bladder may be empty. In some embodiments the bladder may be partially pre-filled with a predetermined amount of the liquefied matrix or hydrogel.

The bladder 1603 (including the barbs) may be composed of natural polymers or copolymers like chitosan, gelatin, alginate, collagen and/or other wound healing promoters; as well as synthetic polymers or copolymers such as PGA, PLA, PDO, PCL, PLLA, or synthetic copolymers like PLGA. The matrix or hydrogel may include a biological or synthetic absorbable polymer or copolymer blend. In some embodiments, the liquefied matrix may be formed from the same material as the bladder, but, in liquid form. In some embodiments, the liquefied matrix may also include pharmaceutical agents or enhancers such as analgesics or antibiotics to promote healing and reduce pain and/or inflammation. Examples below may reference either a hydrogel or liquefied matrix. One skilled in the art will understand that either may be used in accordance with embodiments of this disclosure.

Notched Rod and Wound Plug

Figures 17A, 17B:
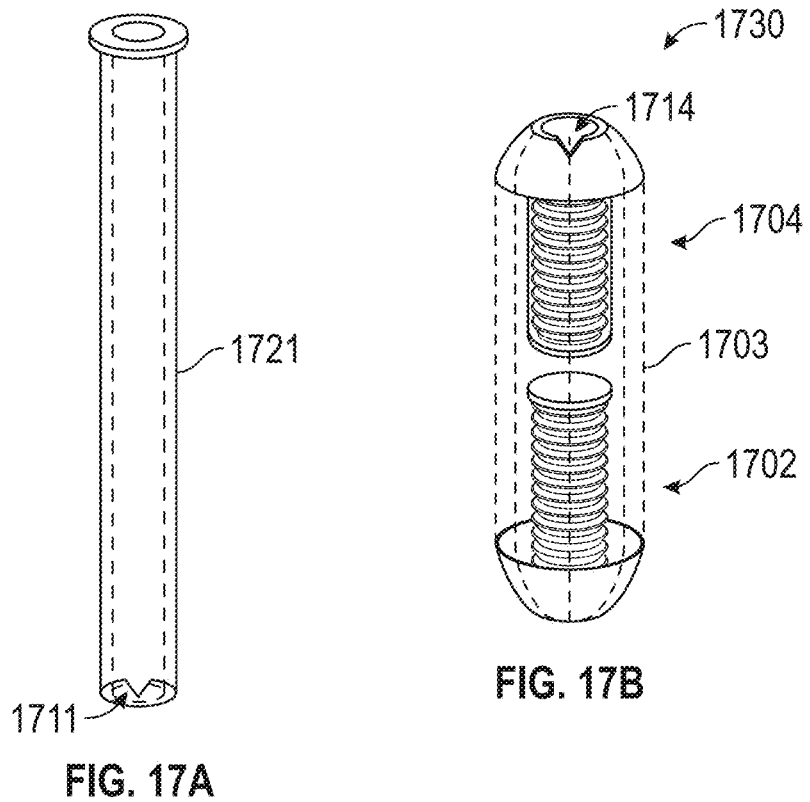
FIGS. 17A-17B illustrate a wound closure apparatus according to embodiments of the disclosure.

According to some embodiments of this disclosure, the rod and wound plug may include reciprocal notches to facilitate alignment. As illustrated in FIG. 17A, a first end of the rod 1721 may include a protruding notch 1711. As illustrated in FIG. 17B, the wound plug 1730 may include a reciprocal notch 1714 configured to receive the protruding notch 1711. Specifically, the suprafascial rivet head 1702 may include the reciprocal notch 1714. For example, when the first end of the rod 1721 abuts a the first end of the wound plug 1730, a user may rotate the rod 1721 such that the protruding notch 1711 mates with the reciprocal notch 1714 to ensure proper alignment of the rod 1721 and the wound plug 1730.

Although illustrated as a triangle in FIGS. 17A-17B, one skilled in the art will understand that the protruding notch 1711 and reciprocal notch 1714 may be any shape such as round, square, rectangular, or another notch shape known in the art that may be used to align the rod 1721 and the wound plug 1714. Although FIG. 17B illustrates an embodiment of a wound plug 1730 that includes a suprafascial rivet head 1704 that is a mirror image of a subfascial rivet head 1702 and a bladder 1703, one skilled in the art will understand that any embodiment of the wound plug described herein may include a reciprocal notch without departing from the scope of this disclosure.

Cannulated Rod and Wound Plug

Figure 18A:
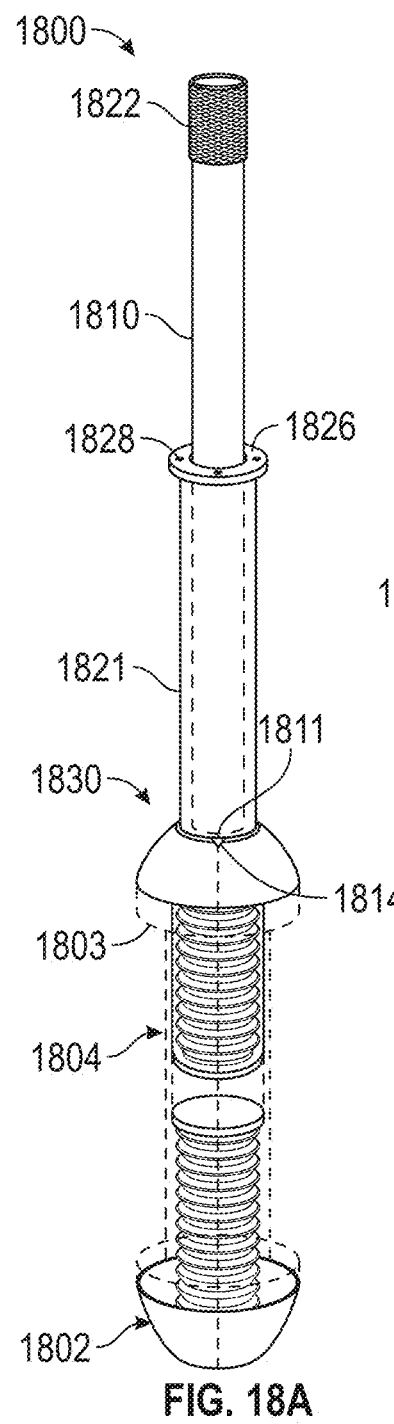
FIGS. 18A-18C illustrate a wound closure apparatus according to embodiments of the disclosure.

FIG. 18A illustrates an assembled wound plug deployment device 1800 according to embodiments of the present disclosure. An assembled wound plug 1830 deployment device may include a cannulated rod 1821 and a wound plug 1830 having a cannulated suprafascial rivet head 1804. The wound plug 1830 having a cannulated suprafascial rivet head 1804 may also include a bladder 1803 as described with respect to FIGS. 16A and 16C. One skilled in the art will understand that any wound plug with a bladder may be used in this embodiment of wound plug deployment device 1800.

Figure 18B:
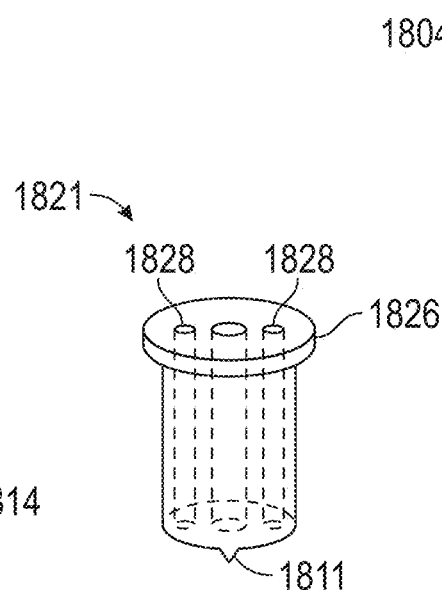
Figure 18C:
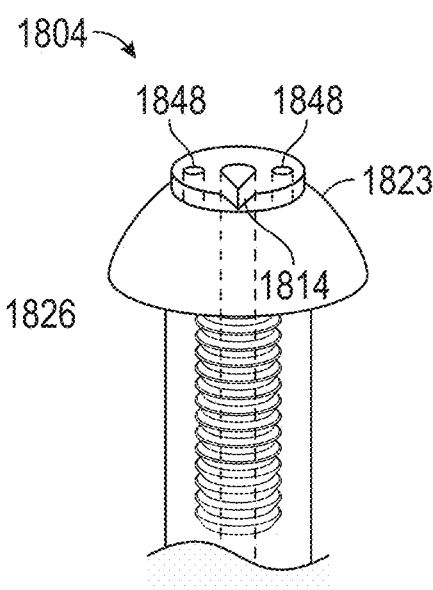

Referring to FIG. 18B (not to scale), the cannulated rod 1821 may include a plurality of cannulae 1828 that run longitudinally within the wall of the rod 1821. The plurality of cannulae 1828 may include a first plurality of openings located on a top surface of the plate 1826 and a second plurality of openings at a first end of the rod 1821 that abuts the subfascial rivet head 1802. One skilled in the art will understand that a cannulated rod 1821 may include at least one cannula. However, any number of cannulae may be located in the rod 1821. Referring to FIG. 18C (not to scale), the suprafascial rivet head 1804 may include a corresponding number of cannulae 1848 located on a top surface of the suprafascial rivet head 1804. The cannulae 1848 may run through the wall of the receiving pawl. In some embodiments, the cannulae 1848 may include an opening below the extension cup 1823.

According to embodiments of the present disclosure, the cannulated rod 1821 and cannulated suprafascial rivet head 1804 may include reciprocal notches 1811 and 1814. In this manner, the user may align the cannula 1828 of the cannulated rod 1821 with the cannula 1848 of the cannulated suprafascial rivet head 1804 as described above with respect to FIGS. 17A-17B. The cannulae 1828, 1848 may provide a path for a user to deliver a liquefied matrix or hydrogel when the rod 1821 and the suprafascial rivet head 1804 are aligned such that the cannulae 1828 and cannulae 1848 are in fluid communication. The hydrogel may be provided to fill the bladder 1803, thereby allowing the bladder 1803 to fill the recesses of the wound.

Figure 18D:
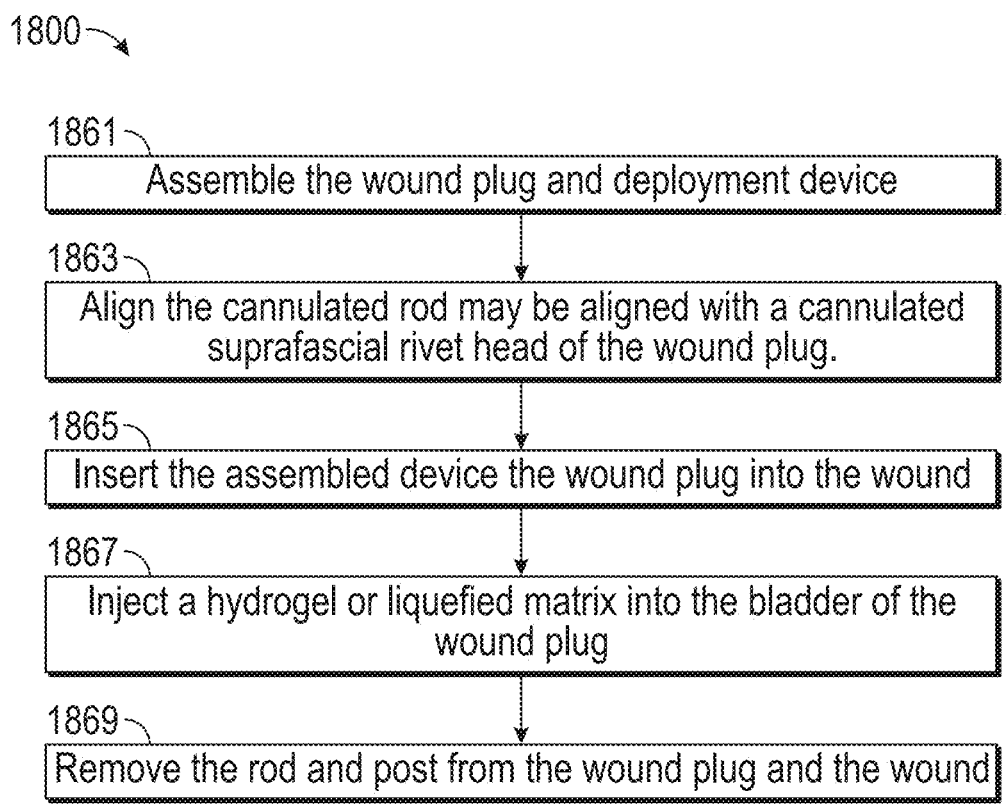
FIG. 18D is a flowchart of a method of deploying a wound plug according to embodiments of the disclosure.

FIG. 18D illustrates a method of using the cannulated rod according to embodiments of the present disclosure. Prior to deployment of the wound plug, the wound plug and deployment device may be assembled (step 1861). For example, the post may be inserted into the cannulated rod. The post may be coupled to the wound plug such that a lower surface of the rod abuts the wound plug. In some embodiments, the cannulated rod may be aligned with a cannulated suprafascial rivet head of the wound plug (step 1863) such that the plurality of cannulae are in fluid communication. The alignment may be performed by rotating the cannulated rod until a protruding notch of the rod mates with a reciprocal notch located in the suprafascial rivet head. The wound plug may be inserted into the wound using the assembled deployment device (step 1865). The deployment device may be used to position the wound plug into the wound, as described, for example, with respect to FIGS. 12A-12C.

Once the wound plug has been inserted, a hydrogel or liquefied matrix may be injected into the bladder of the wound plug (step 1867). A syringe, needleless syringe or other injecting means may be used to inject the hydrogel. As the hydrogel is injected, the bladder of the wound plug may expand laterally to fill recesses in the wound. In some embodiments, the volume of the bladder is known so that a predetermined amount of liquefied matrix or hydrogel may be injected into the wound plug. The matrix or hydrogel may include a biological or synthetic absorbable polymer or copolymer blend. In some embodiments, the hydrogel may also include pharmaceutical agents or enhancers such as analgesics or antibiotics to promote healing and reduce pain and/or inflammation. Once the bladder is filled, the rod and post may be removed from the wound plug and the wound (Step 1869).

Cannulated and Perforated Post

FIG. 19A illustrates a post 1910 according to some embodiments of this disclosure. The post 1910 may include a plurality of perforations 1927 at a first end and a handle 1922 at a second end. The post 1910 may include a cannula 1928 that runs along the longitudinal axis of the post 1910 from the first end to the second end. The cannula 1928 may be in fluid communication with the plurality of perforations 1927. In some embodiments, the first end of the post 1910 may include a suture eye 1929. The suture eye may be configured to receive a suture. In some embodiments, the first end of the post may be swaged (not shown).

FIG. 19B illustrates a cannulated post 1910 sutured to a wound plug 1930 according to embodiments of this disclosure. A suture 1931 may be attached to the cannulated post 1910, for example, by knotting an end of the suture 1931 to the suture eye 1929 of the post 1910. In some embodiments, the suture 1931 may be swaged to the first end of the post 1910. The second end of the suture 1931 may be attached to a wound plug 1930. According to some embodiments, the second end of the suture 1931 may be attached to a wound plug such as those illustrated in FIGS. 16A-16F. For example, wound plug 1930 may include a body (not shown) and a bladder 1903. The suture 1931 may be purse-string stitched around the post receiving opening 1913 of the bladder 1903 of the wound plug 1930. The wound plug may also include a suprafascial rivet head and a subfascial rivet head (not shown). In this manner, when the suture 1931 is pulled taut in a direction away from the wound plug, the purse-string stitch will tighten and close the bladder 1903. One skilled in the art will understand that the suture 1931 may be attached to the wound plug 1930 using an alternate stitch pattern or may be attached as a drawstring around the post receiving opening 1913.

FIG. 19C illustrates an assembled wound plug deployment device 1900 including a cannulated post 1910 sutured to a wound plug 1930 according to embodiments of this disclosure. A suture 1931 may be coupled to the cannulated post 1910, as described above. The first end of the post 1910 may be inserted into the wound plug 1930 through the post-receiving opening 1913 of the bladder 1903 such that the perforations 1927 are located within the bladder 1903. In some embodiments, the perforated end of the post may be disposed through a channel located in the suprafascial rivet head (not shown) of wound plug 1930. In some embodiments, the second end of the post 1910 may also pass through a channel located in the subfascial rivet head (not shown) of the wound plug 1930. The length of suture 1931 located between the post 1910 and the bladder 1903 may be disposed inside the bladder 1903 of the wound plug 1930.

In some embodiments, the post 1910 may not include a suture eye. For example, as illustrated in FIG. 19D, the post may include a first end having a plurality of perforations. The second end may optionally include a handle 1922. According to this embodiment, the corresponding wound plug 1930 may include a post-receiving opening 1913 with a one way valve located therein. The post-receiving opening 1913 may be configured to fit tightly around the circumference of the post 1910. FIG. 19E illustrates an assembled wound plug deployment device 1900. The post 1910 may be positioned through the post-receiving opening 1913. The one way valve 1914 may form a seal around a circumference of the post 1910. According to some embodiments, the post 1910 may be positioned in the wound plug 1930 such that the first end of the post 1910 is near a second end of the wound plug 1930.

In some embodiments, the post 1910 may be manufactured to be coupled to a wound plug 1930 as shown in FIGS. 19B-19C and 19E. For example, a disposable cannulated post 1910 (i.e., single-use posts) may be manufactured to be coupled to the wound plug 1930. In some embodiments, the post 1910 may be provided already inserted into the wound plug 1930, as seen in FIGS. 19C and 19E. In some embodiments the post 1910 may be attached to the wound plug 1930, without being inserted therein, as seen in FIG. 19B. In embodiments where the post 1910 is not inserted into a wound plug 1930, a user may insert the post 1910 into the wound plug 1930 prior to insertion into the wound site. In some embodiments, a disposable cannulated post 1910 may be formed from biodegradable materials and include non-sharp edges. In some embodiments, a reusable cannulated post 1910 may be formed from a material suitable for re-sterilization such as stainless steel, titanium, or any grade of plastic that can withstand the currently used methods of re-sterilization.

The cannulated post 1910 may come in various standardized sizes that correspond to the various port size wound diameters (e.g., 5 mm, 8 mm, 10 mm, 12 mm, and 14 mm). The post 1910 may come in various lengths as well. In some embodiments, the length may correspond to a standard laparoscopic length (e.g., 35 cm-5 cm). This variation in size may allow the cannulated post to be insert the cannulated post and wound plug intra-abdominally, that is, not directly from the surface as described with respect to previous embodiments. Unlike the external method, where the wound plug may be implanted directly through the skin into the wound without an internal or laparoscopic view the implanting procedure, the intra-abdominal or internal method may require visualization, for example, with a laparoscope. The internal method may be useful for mega obese patients where the trajectory of the port site wound cavity is steeply angled and the skin incision may be far away from the wound site. Further, the internal method may provide greater accuracy in implant placement and deployment.

Method of Deployment of Wound Plug with Cannulated Post

Figure 20C:
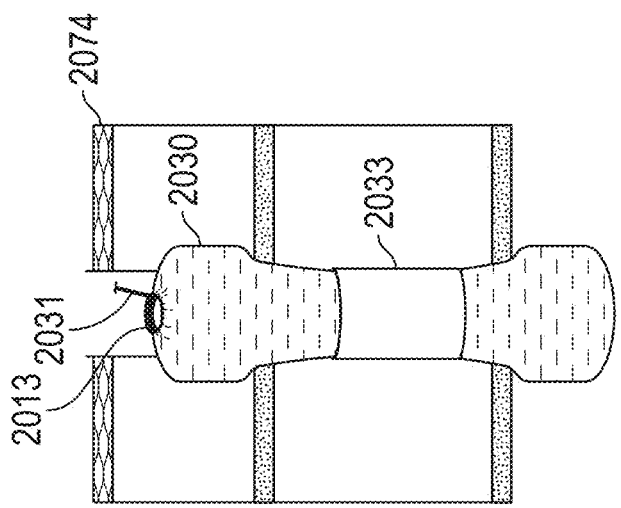
FIGS. 20A-20C illustrate a wound closure apparatus during stages of deployment of the wound plug according to embodiments of the disclosure.
Figure 20B:
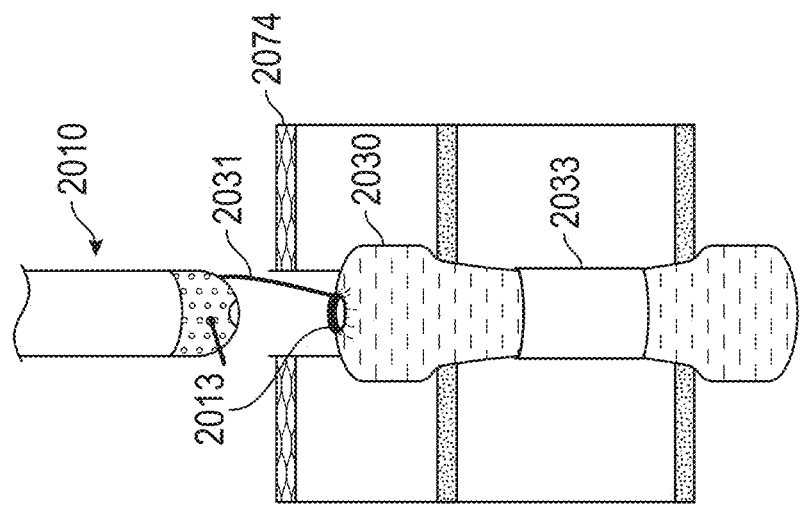
Figure 20A:
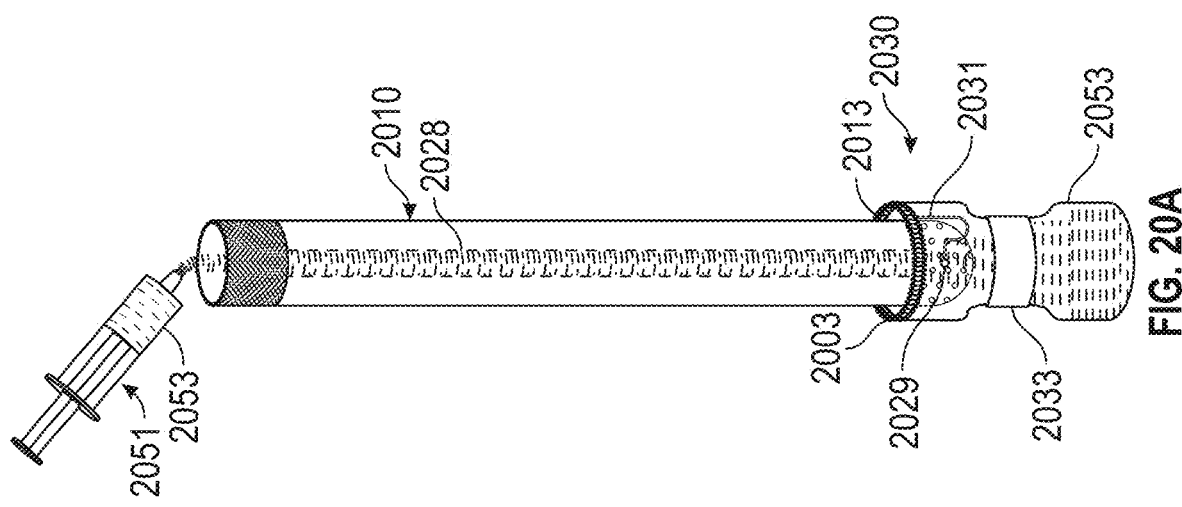
Figure 20D:
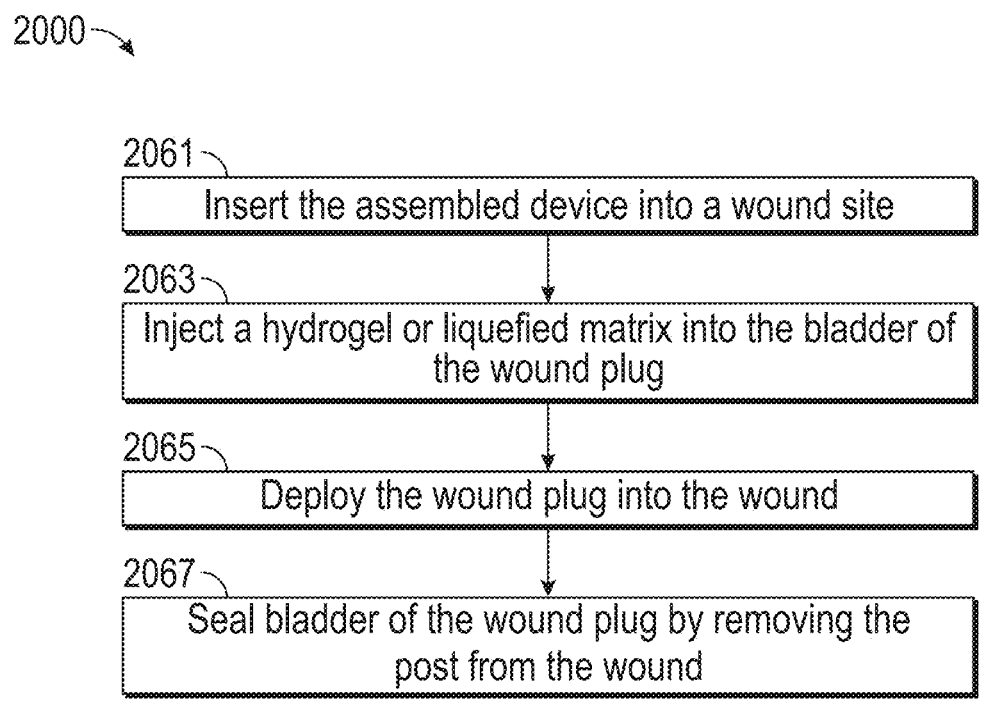
FIG. 20D is a flowchart of a method of deploying a wound plug according to embodiments of the disclosure.

FIGS. 20A-20C illustrate a wound plug implanted according to embodiments of the disclosure. FIG. 20D is a block diagram of a method 2000 for implanting a wound plug according to embodiments of the disclosure. Once the cannulated post 1910 and wound plug 1930 are assembled as illustrated in FIG. 19C, the wound plug 1930 may be implanted into a wound site. For example the assembled device 2000 may be inserted into a wound site (step 2061). The insertion according to both the external and internal methods will be discussed in greater detail below. The assembled device 2000 includes at least a cannulated post 2010 inserted into a wound plug 2030 having a bladder 2003. More details regarding insertion into wound site will be provided below.

Once inserted into the wound site, a syringe 2051 may be used to inject a liquefied matrix or hydrogel 2053 into the cannulated post 2010 (step 2063), thereby filling the bladder 2003. In some embodiments, the syringe 2051 may be filled with a predetermined amount of liquefied matrix 2053 corresponding to the volume of the bladder 1903. In some embodiments, the wound site of the wound plug may be monitored laparoscopically to determine the amount of liquefied matrix 2053 to fill the bladder 1903. The liquefied matrix 2053 may be made from the same material as the bladder, for example, a biological or synthetic absorbable polymer or copolymer blend. Additives such as analgesics and antibiotics may be added to the liquefied matrix to reduce pain and infection.

Filling the bladder 2003 may implant the wound plug 2030 into the wound site as seen in FIG. 20B. The wound plug 2030 may then be deployed (step 2065) as described with respect to embodiments above. For example, the post 2010 may be pulled in a direction away from the wound site, thereby interlocking the subfascial and suprafascial rivet heads (e.g., FIG. 12A-12B). In some embodiments, the wound plug may be deployed during the injection of hydrogel. For example, during the injection, the post may move from its original position toward the post-receiving opening 1913, thereby deploying the wound plug. In some embodiments, the post may stay in its deployment position within the subfascial portion of the balloon as the balloon fills with the hydrogel. During the deployment, the stays and or extension feature (e.g., cup, or stays illustrated in FIGS. 10C-10F and 15A-15C) may deploy, further securing the wound plug 1930 in the wound site.

Continuing to remove the post 2010 from the wound site may seal the bladder 2003 (step 2067). For example, as seen in FIG. 20B in some embodiments, removing the post 2010 from the wound site and away from the wound plug 2030 may pull the suture 2031 taut, thereby closing the post-receiving opening 2013 of the bladder 2003. Once the bladder 2003 is closed, the suture 2031 may be cut below the skin. In some embodiments, removing the post from the bladder of the wound plug may seal the wound plug with, for example a one way valve.

If the post 2010 is disposable, then the post may be discarded. If the post 2010 is reusable, then the post 2010 may be tied to a second wound plug 2030 and inserted into the bladder 2003 to be used in another wound site. For example, a loose end of a second suture 2031 may be knotted to the suture eye 2029 of the post 2010 as described above. In some embodiments, the one-way valve disposed in the post-receiving opening 2013 may seal upon being filled to capacity with the liquefied matrix. In some embodiments, removing the post 2010 from the wound plug 2030 may close the one-way valve disposed in the post-receiving opening 2013 of the bladder 2003, thereby sealing the filled bladder 2003.

FIG. 20C illustrates the wound plug 2030 fully deployed and implanted in a wound site. After the wound plug is deployed, the incision at the skin 2074 may be closed.

External Method of Insertion

Figure 21A:
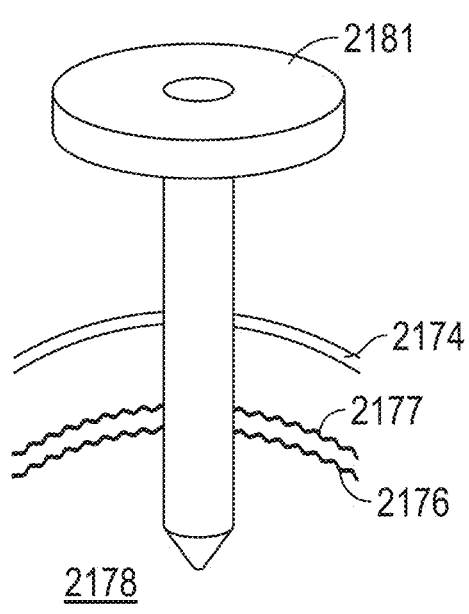
FIGS. 21A-21C illustrate an insertion site of a wound plug apparatus and the wound plug apparatus according to embodiments of the disclosure.
Figure 21B:
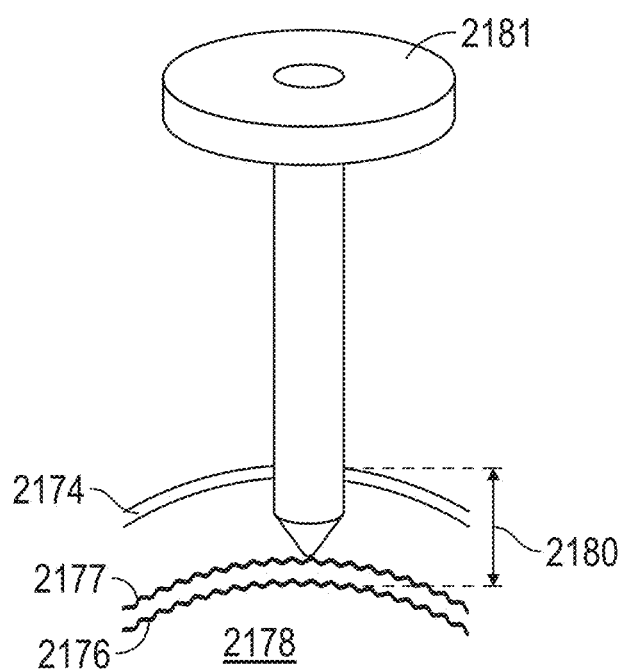
Figure 21C:
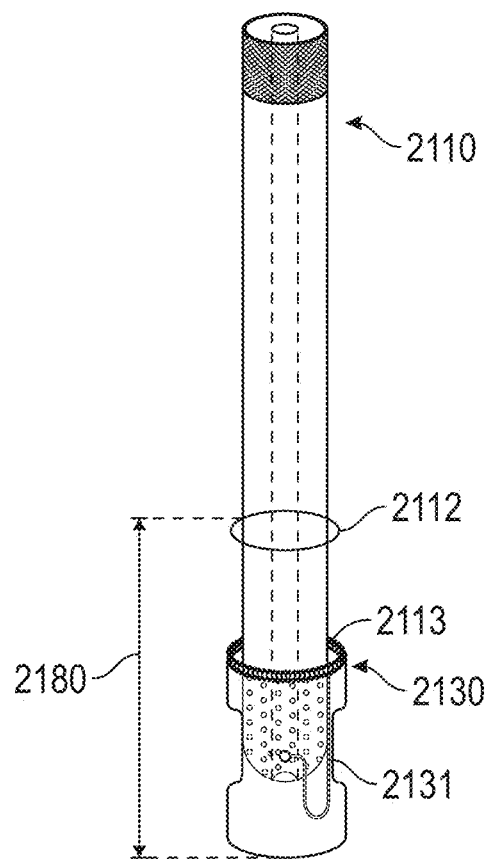
Figure 21D:
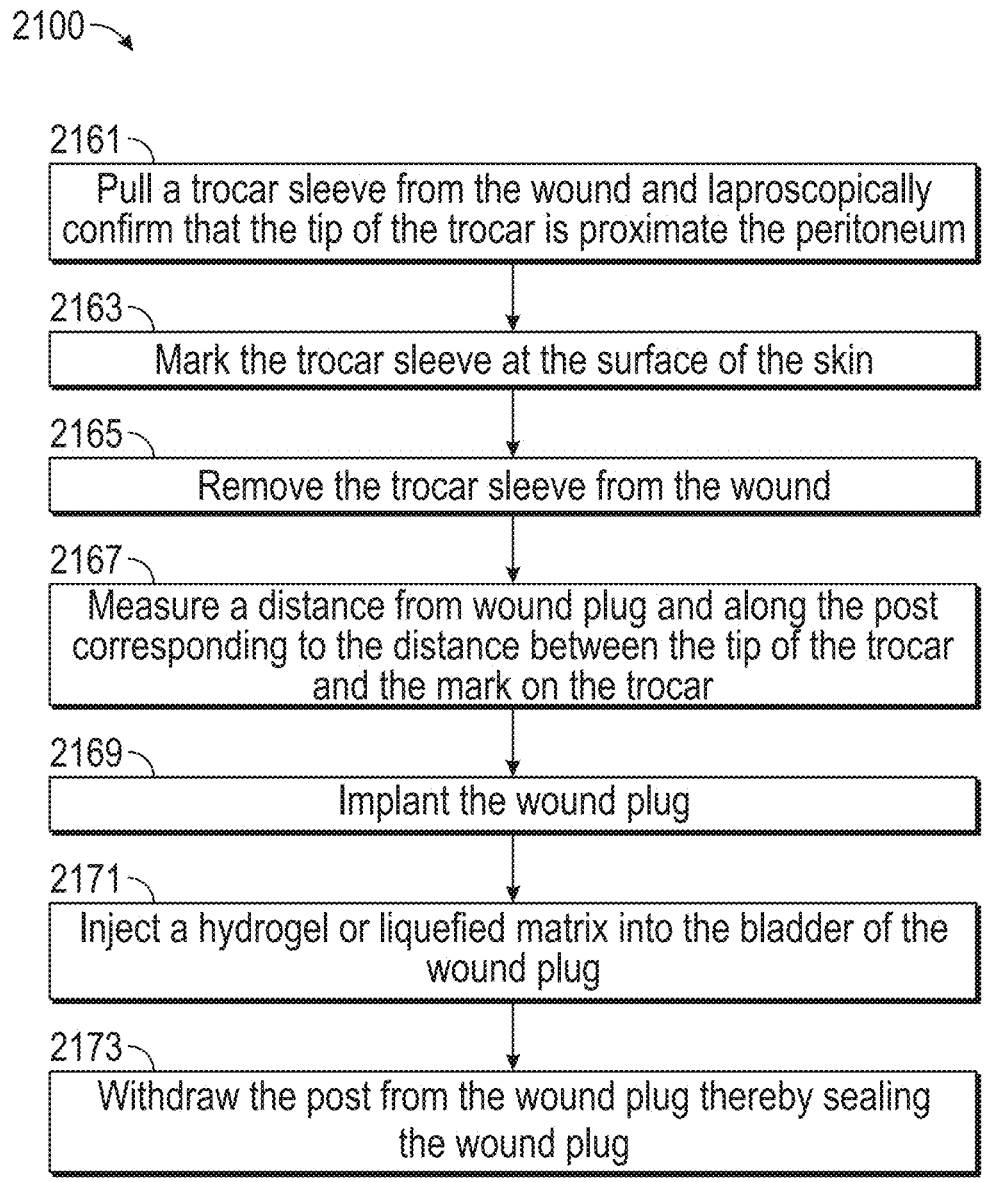
FIG. 21D is a flowchart of a method of inserting a wound plug according to embodiments of the disclosure.

FIGS. 21A-21C illustrate the external method of inserting an assembled post 2110 with a wound plug 2130 according to embodiments of this disclosure. FIG. 21D is an example of the external method 2100 according to embodiments of this disclosure. Referring to FIG. 21A, after performing laparoscopic surgery, a trocar sleeve 2181 may be embedded in the abdomen 2178 of a patient. In order to determine the depth of the peritoneum 2176, according to some embodiments of this disclosure, a user may pull the trocar sleeve 2181 from the wound and laparoscopically confirm that the tip of the trocar 2181 is proximate the peritoneum 2176 (step 2161) as shown in FIG. 21B. The user may then remove the laparoscope (not shown) and any other lines, e.g., $CO_2$.

The user may mark the trocar sleeve 2181 at the surface of the skin (step 2163). The distance 2170 between the mark and the tip of the trocar sleeve 2181 should correspond to the depth of the wound site. The mark may not be a physical mark. For example, the user may use a finger to mark this location on the trocar sleeve 2181. In some embodiments, a user may use a pen or other writing implement to mark this location. The user may then remove the trocar sleeve 2181 from the wound (step 2165). The distance 2180 between the mark and the tip of the trocar sleeve 2181 should correspond to the depth of the peritoneum of the wound site.

The user may then measure distance 2180 along the wound plug 2130 (step 2167). For example, the user may measure the distance 2180 from the second end of the wound plug to a location along the post 2110 to determine the depth that the wound plug should be advanced. Once the distance is measured, the user may mark the post 2110. In some embodiments, the post 2110 may include a movable ring 2112 to mark the distance 2180. In some embodiments the user may mark the distance 2180 with a finger or pen as described above.

The wound plug may then be implanted (step 2169) as described above with respect to FIG. 21D. For example, the wound plug may be advanced to the wound site. A liquefied matrix may be injected through a cannula of the post and into the wound plug (step 2171), thereby filling the bladder of the wound plug. The post may then be withdrawn from the wound plug, thereby closing and sealing the bladder (step 2173).

Internal Method of Insertion

Figure 22A:
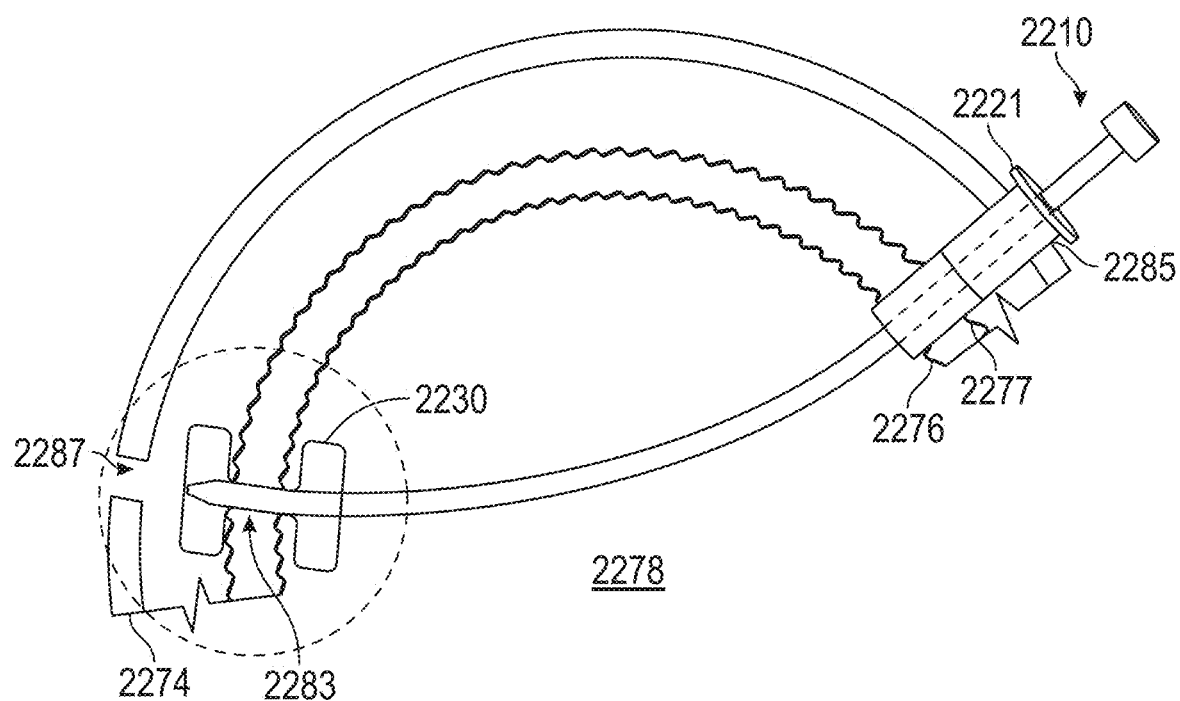
FIGS. 22A-22B illustrate a wound plug apparatus during stages of deployment of the wound plug according to embodiments of the disclosure.
Figure 22B:
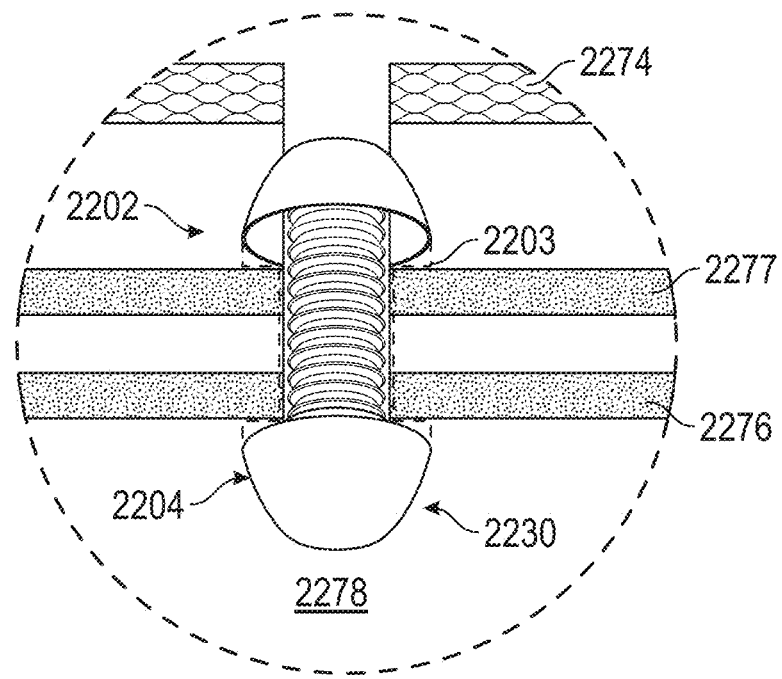
Figure 22C:
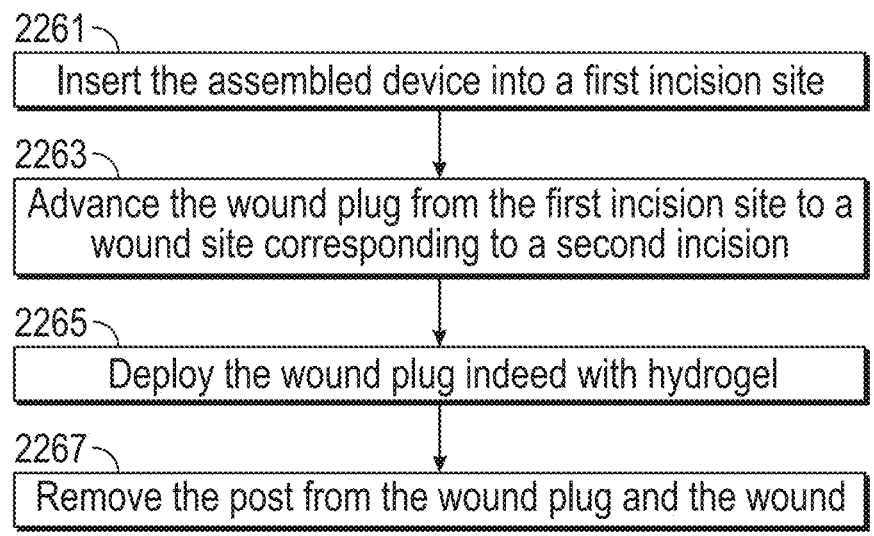
FIG. 22C is a flowchart of a method of implanting a wound plug according to embodiments of the disclosure.

FIGS. 22A-22B illustrate the internal method of inserting and implanting an assembled post 2210 with a wound plug 2230 intra-abdominally according to the embodiments of this disclosure. FIG. 22C is an example of the internal method according to embodiments of this disclosure. Referring to FIG. 22A, an assembled apparatus including a rod 2221 having a laparoscopic length post 2210 disposed there through may be inserted into an incision 2285 (step 2261). The post may have a wound plug 2230 disposed thereon. The post 2110 nay be inserted through a trocar instead of rod 2221, according to some embodiments of this disclosure. The post 2210 may be advanced through a first incision 2285 in the abdominal cavity 2278 toward a wound site 2283 in the peritoneum 2276 corresponding to a second incision site 2287 in the skin 2274 (step 2263). In some embodiments, the second incision site 2287 may be located at an opposite end of the abdominal cavity 2278. A laparoscope (not shown) may be used to monitor the post 2210 so a user may guide the post 2210 to the wound site 2283.

Once the post 2210 is at the wound site 2283 the wound plug 2230 may be injected with the hydrogel and deployed (step 2265) as described above. Referring to FIG. 22C, due to the insertion of the wound plug 2230 intra-abdominally, the orientation of the subfascial rivet head and the suprafascial rivet head with respect to the layers of tissue may be reversed from the embodiment shown in FIG. 20C. For example, the subfascial rivet head may be proximate the skin and abut the anterior fascia 2278 while the suprafascial rivet head abuts the peritoneum 2276.

The post 2210 and rod 2221 may then be withdrawn from the incision 2285 (step 2267). If the post is reusable, the post 2210 may be reassembled with a new wound plug 2230. If the post is disposable, the first post 2210 may be disposed of and a second post may be used to close any additional wound cites. The internal, intra-abdominal method may allow for accurate placement of the wound plug. Moreover, the internal method may reduce the time required to close the wounds following a laparoscopic procedure. For example, as one physician or medical professional is deploying a wound plug laparoscopically, another physician or medical professional may simultaneously be closing the incision at the surface of the skin.

According to some embodiments, both the internal and external methods may be used to close wound sites in a patient. For example, following a laparoscopic procedure, there may be multiple wound sites in the abdominal cavity. According to some embodiments, the internal method may be used to close each of the wound sites in the patient that do not correspond to the incision having the laparoscope. In that way, the laparoscope is available to determine the depth for inserting the wound plug into the tissue. Once the multiple wound sites have been closed, the final wound site corresponding to the previous location of the laparoscope may be closed using the external method.

Rivet Head/Bladder Hybrid Wound Plug

FIGS. 23A-23F illustrate a hybrid wound plug according to embodiments of the present disclosure. According to some embodiments, a wound plug 2330 may include a suprafascial rivet head 2304 that is molded or otherwise coupled to a subfascial bladder 2302. For example, the suprafascial rivet head 2304 and subfascial bladder 2302 may be formed together or formed separately and bonded. Although various examples of the wound plug are illustrated one skilled in the art will understand that are not limited by these examples.

Figure 23A:
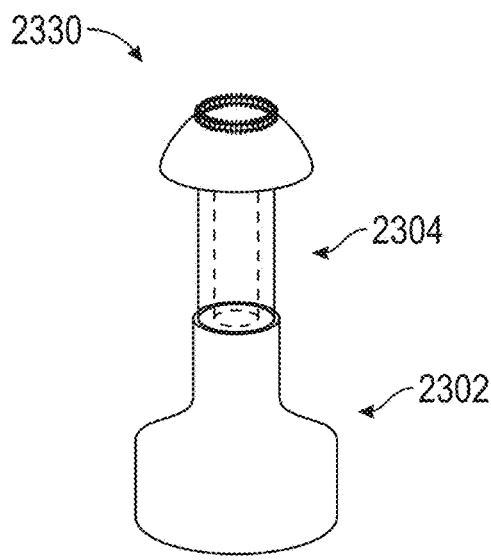
FIGS. 23A-23F illustrate a wound plug according to embodiments of the disclosure.
Figure 23B:
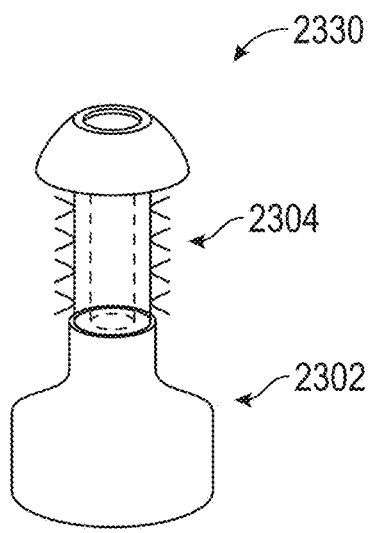
Figure 23C:
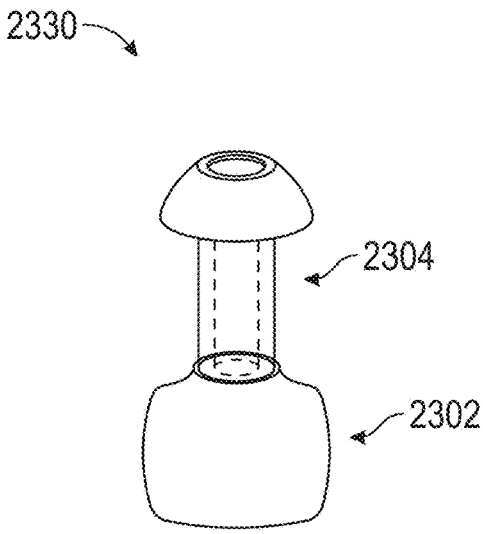
Figure 23D:
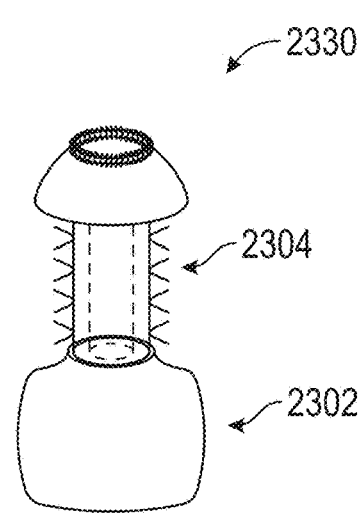
Figure 23E:
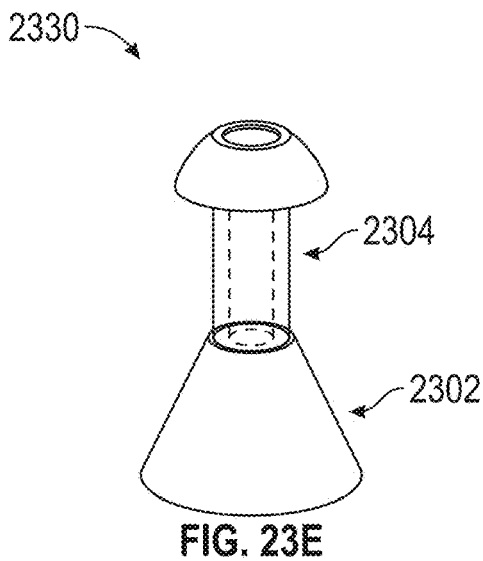
Figure 23F:
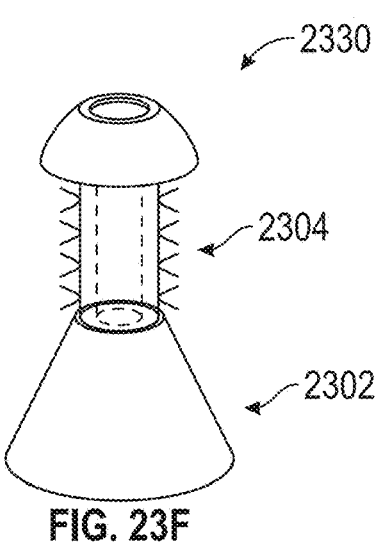
Figure 23G:
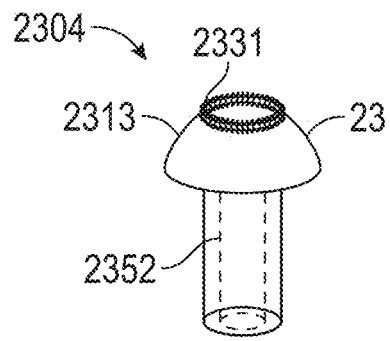
FIGS. 23G-23L illustrate a suprafascial rivet head according to embodiments of the disclosure.

FIG. 23G-23L illustrate suprafascial rivet heads 2304 according to embodiments of the present disclosure. Referring to FIG. 23G, according to some embodiments, the suprafascial rivet head 2304 may include a hollow column portion 2352 molded or otherwise attached to a suprafascial extension at a first end of the suprafascial rivet head 2304. The hollow column portion 2352 may include a post-receiving opening 2313 at a first end and a second end configured to be in fluid communication with a subfascial bladder 2302 (not shown). An interior of the hollow column portion 2352 may be substantially smooth. That is, the hollow column portion may not include interior ridges as described above with respect to, for example, FIGS. 10C-10F.

Figure 23H:
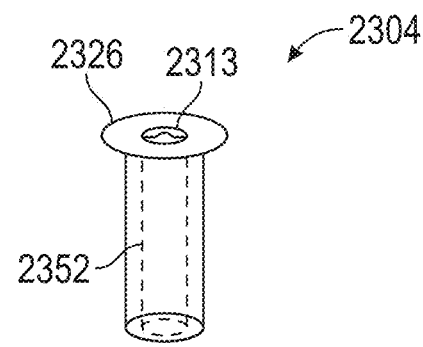

As seen in FIG. 23G, the suprafascial extension may be in the shape of a cup 2323. The extension cup 2323 may be disposed around the post-receiving opening 2313 located at a first end of the suprafascial rivet head 2304. The suprafascial extension cup 2323 may be any size, shape, thickness, or configuration. For example, the suprafascial extension cup 2323 may project at an angle (e.g. 80 or 90 degrees, etc.) from an outer perimeter of the suprafascial rivet head 2304. In some embodiments, the suprafascial extension may be substantially flat. For example, as illustrated in FIG. 23H, the suprafascial extension may be substantially flat in the shape of a plate 2326. One skilled in the art will understand that any shape may be suitable for the suprafascial extension provided the extension may expand radially to cover the wound located in the anterior fascia.

Figure 23I:
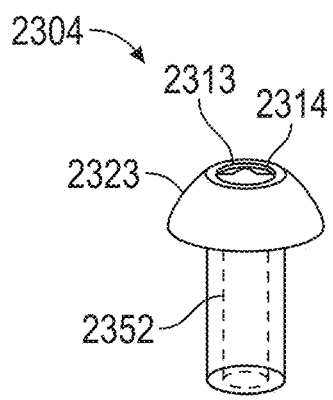

Referring again to FIG. 23G, the post-receiving opening 2313 may include a suture 2331 purse-string stitched around the circumference of the post-receiving opening 2313. According to some embodiments, the suture 2331 may be used to attach the column portion 2352 to the extension cup 2323 of the suprafascial rivet head 2304. For example, the purse-string stich around the post-receiving opening 2313 may stitch together the column portion 2352 and the extension cup 2323. One skilled in the art will understand that the suture 1931 may be attached to the wound plug 1930 using an alternate stitch pattern or may be attached as a drawstring around the post receiving opening 1913. The second end of the suture 2331 may be attached to a cannulated post as described above, for example with respect to FIG. 19B. In some embodiments, the post receiving opening 2313 may include a one-way valve 2314 or trap-door as seen in FIG. 23I. The one-way valve 2314 or trapdoor may be similar to above-discussed one-way valves.

Figure 23J:
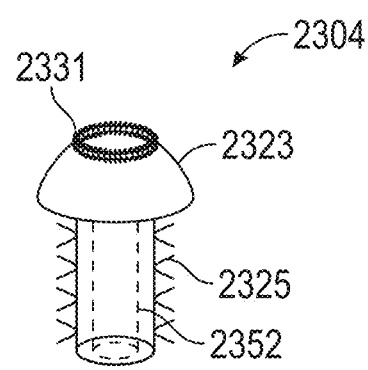

Referring to FIG. 23J, the suprafascial rivet head 2304 may include a hollow column portion 2352 molded or otherwise attached to a suprafascial extension at a first end of the suprafascial rivet head 2304. The hollow column portion 2352 may include a post-receiving opening 2313 at a first end and a second end configured to be in fluid communication with a subfascial bladder 2302 (not shown). An interior of the hollow column portion 2352 may be substantially smooth. An exterior of the hollow column portion 2352 may include a plurality of barbs, according to embodiments of the present disclosure. In some examples, the barbs 2325 may be circumferentially oriented features that project from the surface of the hollow portion 2352. In some embodiments, the barbs 2325 may surround the suprafascial rivet head 2304 of the wound plug 2330 in a spiral orientation (not shown). In some embodiments, the barbs 2325 may be unidirectional, having features pointing in the same direction. In some embodiments, the barbs 2325 may be positioned bi-directional or multi-directional.

Figure 23K:
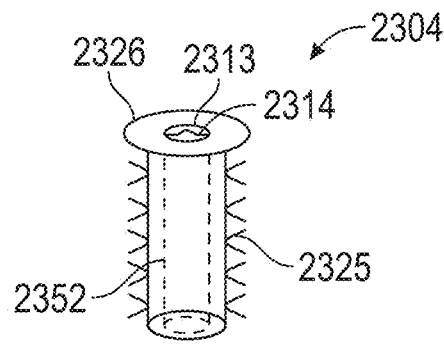

As seen in FIG. 23J, the suprafascial extension may be in the shape of a cup 2323. The extension cup 2323 may be disposed around the post-receiving opening 2313 located at a first end of the suprafascial rivet head 2304 and be similar to extension cups discussed above. In some embodiments, the suprafascial extension may be substantially flat. For example, as illustrated in FIG. 23K, the suprafascial extension may be substantially flat in the shape of a plate 2326. One skilled in the art will understand that any shape may be suitable for the suprafascial extension provided the extension may expand radially to cover the wound located in the anterior fascia.

Figure 23L:
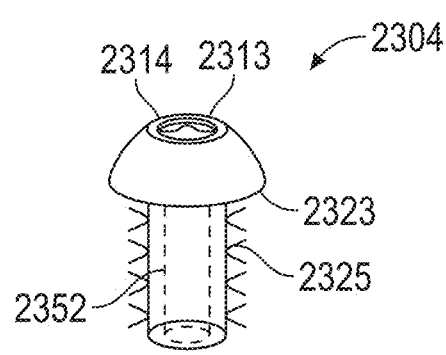

Referring again to FIG. 23J, the post-receiving opening 2313 may include a suture 2331 purse-string stitched around the circumference of the post-receiving opening 2313 as discussed above, e.g., with respect to FIG. 23G. In some embodiments, the post receiving opening 2313 may include a one-way valve 2314 or trap-door as seen in FIG. 23L. The one-way valve 2314 or trapdoor may be similar to above-discussed one-way valves.

The suprafascial rivet head 2304, including the barbs, may be developed from either biological or chemical polymers. For example, the suprafascial rivet head 2304 may be electrospun or dip coated with an absorbable chemical polymer to enhance the full radial expansion of the supra fascial extension, e.g., extension up 2323, on the anterior abdominal fascia. According to some embodiments, once the wound plug 2330 is deployed, the shape memory properties of the suprafascial extension cup 2323 may be affected by the body's temperature and/or pH relative to a pre-determined time interval also inherent in their chemical properties. These physical and biological properties may cause the sides of the suprafascial extension cup 2323 to automatically deploy into a full radial expansion. In some embodiments, the weight of tissue located above the suprafascial extension cup may cause the suprafascial extension cup to flatten. In some embodiments, the suprafascial extension may serve as a biohybrid scaffold. For example, the suprafascial extension may include micro-perforations to allow for native tissue ingrowth and takeover.

Figure 23M:
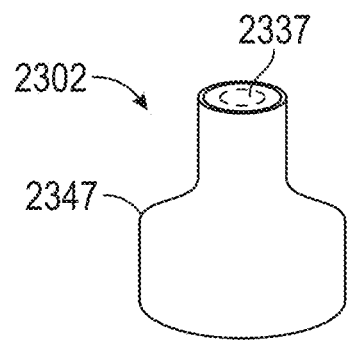
FIGS. 23M-23O illustrate a subfascial bladder according to embodiments of the disclosure.
Figure 23N:
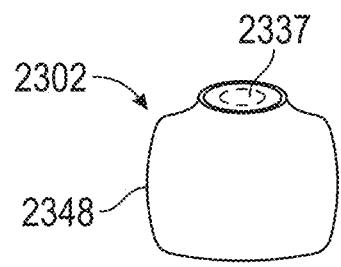
Figure 23O:
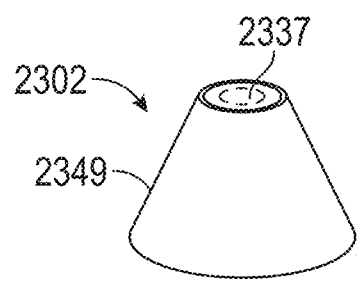

FIGS. 23M-23O illustrate subfascial bladders 2302 according to embodiments of the present disclosure. The subfascial bladder may include an opening 2337 at a first end configured to be in fluid communication with the second end of the subfascial rivet head. The subfascial bladders may come in a variety of shapes. According to some embodiments, the subfascial bladder 2302 may have a wider second end that narrows to its first end where the subfascial bladder 2349 attaches to the suprafascial rivet head 2304. For example as seen in FIG. 23M, the subfascial bladder may be in the shape of an upside-down T 2374. Referring to FIG. 23N, the subfascial bladder may be oval 2348 in the shape. Referring to FIG. 23O, the subfascial bladder may be conical 2349 in the shape. One skilled in the art will understand that any shape may be suitable for the subfascial bladder as long as the subfascial bladder expands radially to cover the circumference of the wound of the peritoneum and/or eliminate deadspace. In some embodiments, the bladder may be formed from the same material as the suprafascial rivet head.

One skilled in the art will understand that a hybrid wound plug, e.g., wound plugs 23A-23F, may include suprafascial rivet head and a subfascial bladder as described above. According to some embodiments, a hybrid wound plug may include a suprafascial bladder and a subfascial rivet head as depicted in FIGS. 24A-24D. Specifically, a hybrid wound plug 2430 may include a suprafascial bladder 2404 attached to a subfascial rivet 2402 head as seen in FIGS. 24A-24D. The suprafascial bladder 2404 and subfascial rivet 2402 may be formed together or in some embodiments may be formed separately and then coupled, e.g., chemically joined. The hybrid wound plugs according to embodiments illustrated in FIGS. 24A-24D may be formed from the same materials as the wound plugs discussed above.

Figure 24A:
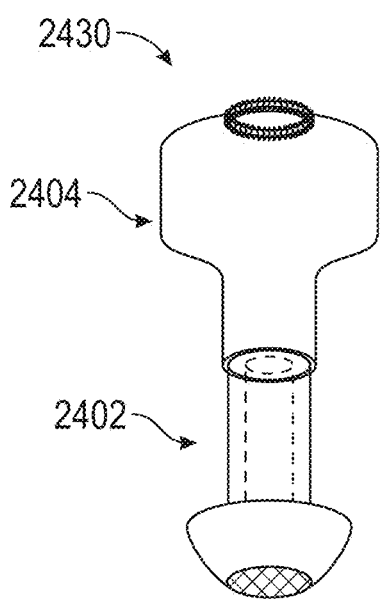
FIGS. 24A-24D illustrate a wound plug according to embodiments of the disclosure.
Figure 24B:
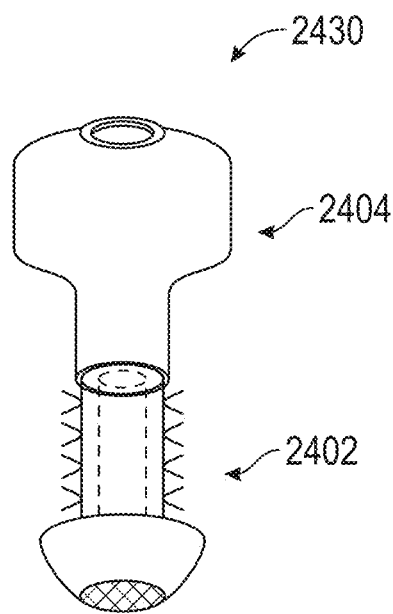
Figure 24C:
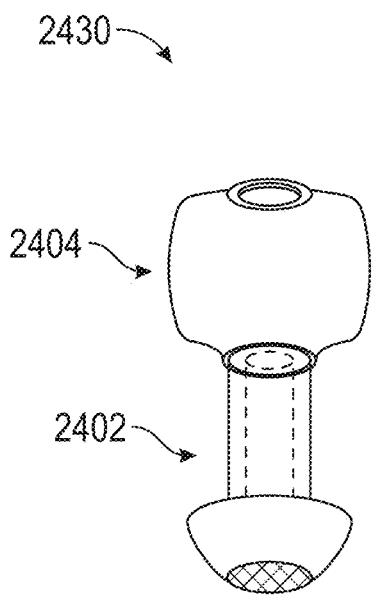
Figure 24D:
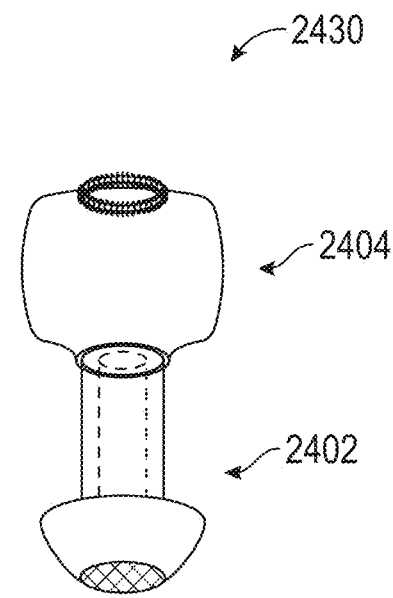
Figure 24E:
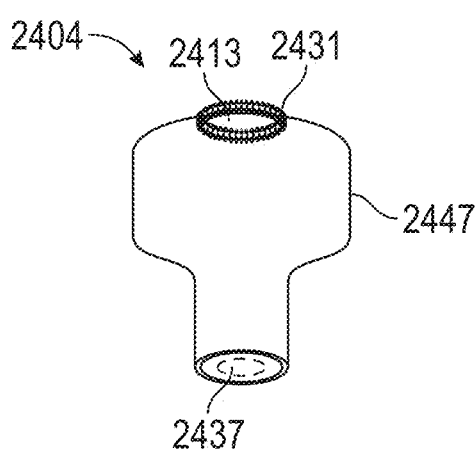
FIGS. 24E-24J illustrate a suprafascial bladder according to embodiments of the disclosure.
Figure 24F:
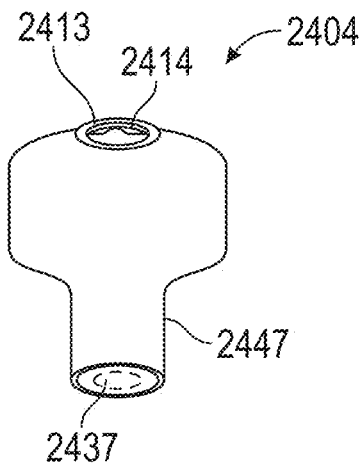

FIGS. 24E-24J illustrate examples of suprafascial bladders 2404 according to embodiments of the present disclosure. Generally, a suprafascial bladder 2404 may include a post-receiving opening 2413 disposed at a first end and a second opening 2443 at a second end. Referring to FIG. 24E, the post-receiving opening 2413 may include a suture 2431 purse-string stitched around the circumference of the post-receiving opening 2413, as described above, e.g., FIG. 23G. In some embodiments, the post receiving opening 2413 may include a one-way valve 2414 or trap-door as seen in FIG. 24F. The one-way valve 2414 or trapdoor may be similar to above-discussed one-way valves. The second opening 2443 is configured to be in fluid communication with a subfascial rivet head, e.g., subfascial rivet head 2402 in FIGS. 24K-24M.

Figure 24G:
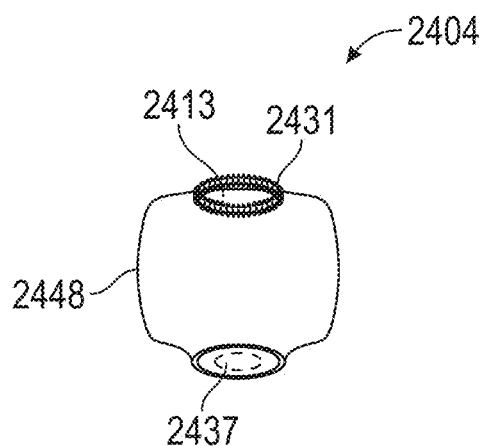
Figure 24H:
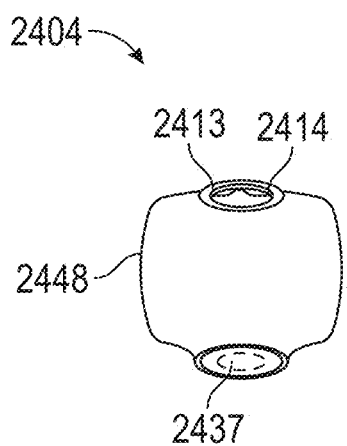
Figure 24I:
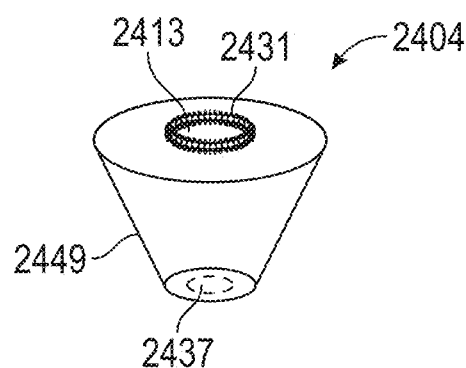
Figure 24J:
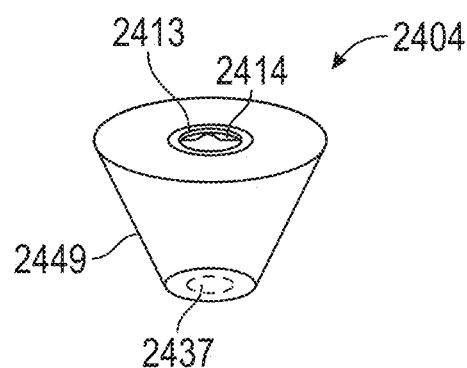

The suprafascial bladders 2404 may come in a variety of shapes. According to some embodiments, the suprafascial bladder 2404 may have a wider second end that narrows to its first end where the suprafascial bladder 2404 attaches to the subfascial rivet head 2402. For example as seen in FIGS. 24E-24F, the suprafascial bladder 2404 may be T-shaped 2447. Referring to FIGS. 24G-24H, the suprafascial bladder 2404 be oval 2448. Referring to FIGS. 24I-24J, the suprafascial bladder 2404 may be conical 2449. One skilled in the art will understand that any shape may be suitable for the suprafascial bladder as long as the suprafascial bladder 2404 expands radially to cover the circumference of the wound in the anterior fascia and/or eliminate deadspace.

Figure 24K:
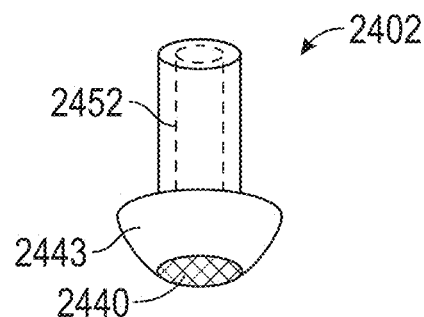
FIGS. 24K-24M illustrate a subfascial rivet head according to embodiments of the disclosure.
Figure 24L:
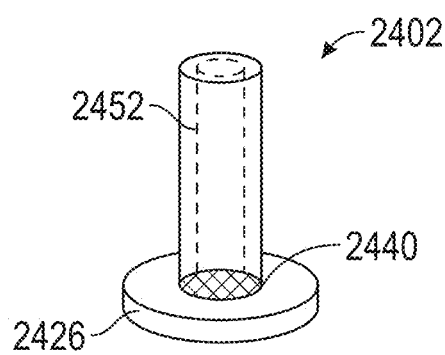
Figure 24M:
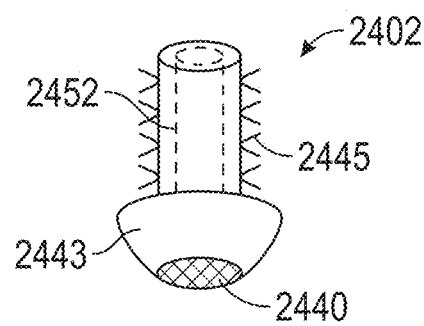

FIGS. 24K-24M illustrate a subfascial rivet head 2402 according to embodiments of the present disclosure. Referring to FIG. 24K, the subfascial rivet head 2402 may include a hollow column portion 2452 and an extension portion. The hollow column portion 2452 may be in fluid communication with the bladder 2447 at a first end and terminate in a bio-hybrid scaffold 2440 at a second end. The bio-hybrid scaffold 2440 may prevent the egress of any biogels or fluids disposed in the wound plug 2430 to the surrounding tissue. The extension portion may be disposed at the second end of the hollow column portion 2452. According to some embodiments, the extension portion may be an extension cup 2423 as described above. According to some embodiments, the extension portion may be a plate 2426, as illustrated in FIG. 24L.

Referring to FIG. 24M, the subfascial rivet head 2402 may include a plurality of barbs 2425disposed on an outer surface of the hollow column portion 2452. In some examples, the barbs 2425 may be circumferentially oriented features that project from the surface of the hollow portion 2452. In some embodiments, the barbs 2425 may surround the subfascial rivet head 2402 in a spiral orientation (not shown). In some embodiments, the barbs 2425 may be unidirectional, having features pointing in the same direction. In some embodiments, the barbs 2425 may be positioned bi-directional or multi-directional.

Figure 25A:
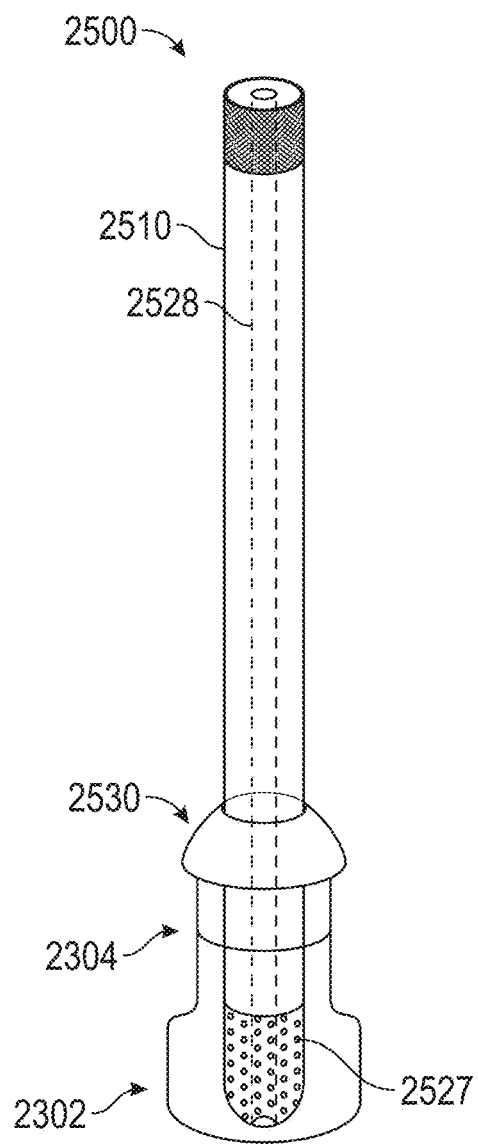
FIG. 25A-25B illustrates a wound closure apparatus according to embodiments of the disclosure.
Figure 25B:
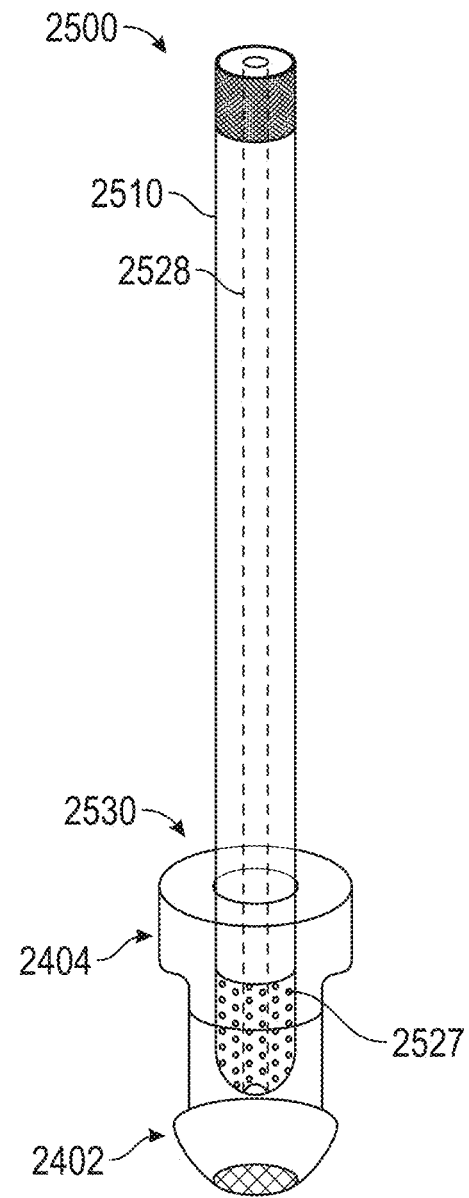

FIG. 25A-25B show assembled wound plug delivery devices according to embodiments of the present disclosure. Referring to FIG. 25A the assembled wound plug delivery device 2500 may include a perforated post 2510 positioned in a hybrid wound plug 2530. The hybrid wound plug 2500 may include a suprafascial rivet head 2304 coupled to a subfascial bladder 2302. The perforated post 2510 may be similar to perforated posts described above. Referring to FIG. 25B the assembled wound plug delivery device 2500 may include a perforated post 2510 positioned in a hybrid wound plug 2530. The hybrid wound plug may include a suprafascial bladder 2404 coupled to a subfascial rivet head 2402. Although the assembled wound plug is shown with two examples of a hybrid wound plug, one skilled in the art will understand that any hybrid wound plug in accordance with embodiments of the present disclosure may be used.

Method of Deployment for Hybrid Wound Plug

Figure 26C:
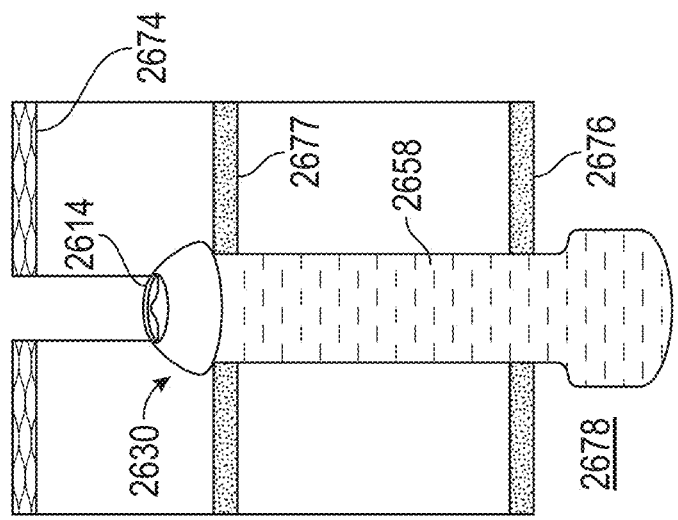
FIGS. 26A-26C illustrate a wound closure apparatus during stages of deployment of the wound plug according to embodiments of the disclosure.
Figure 26B:
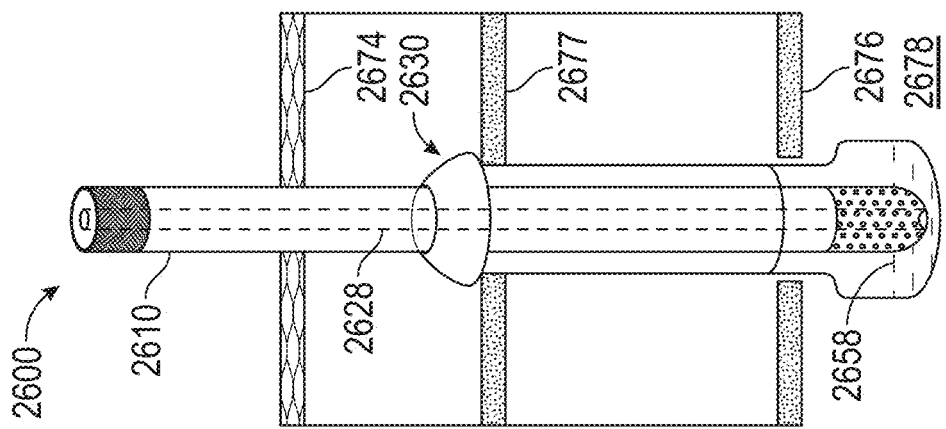
Figure 26A:
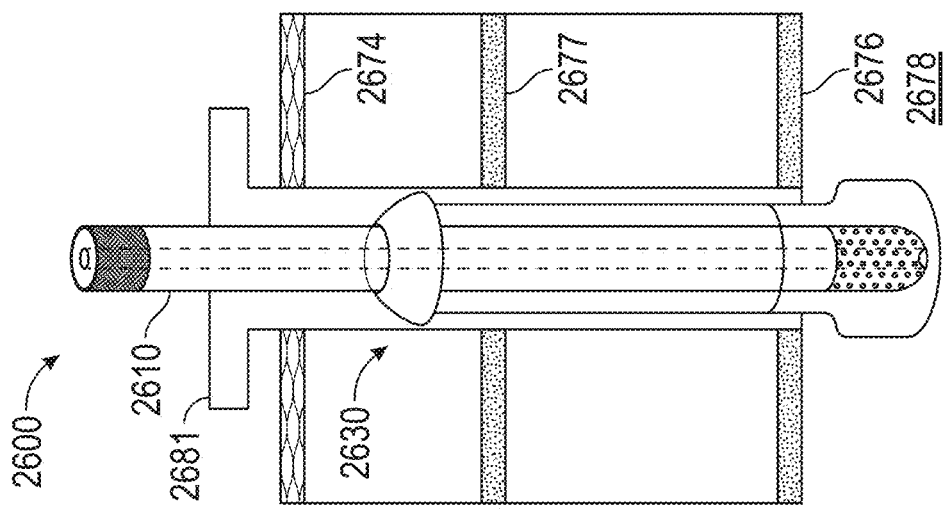
Figure 27:
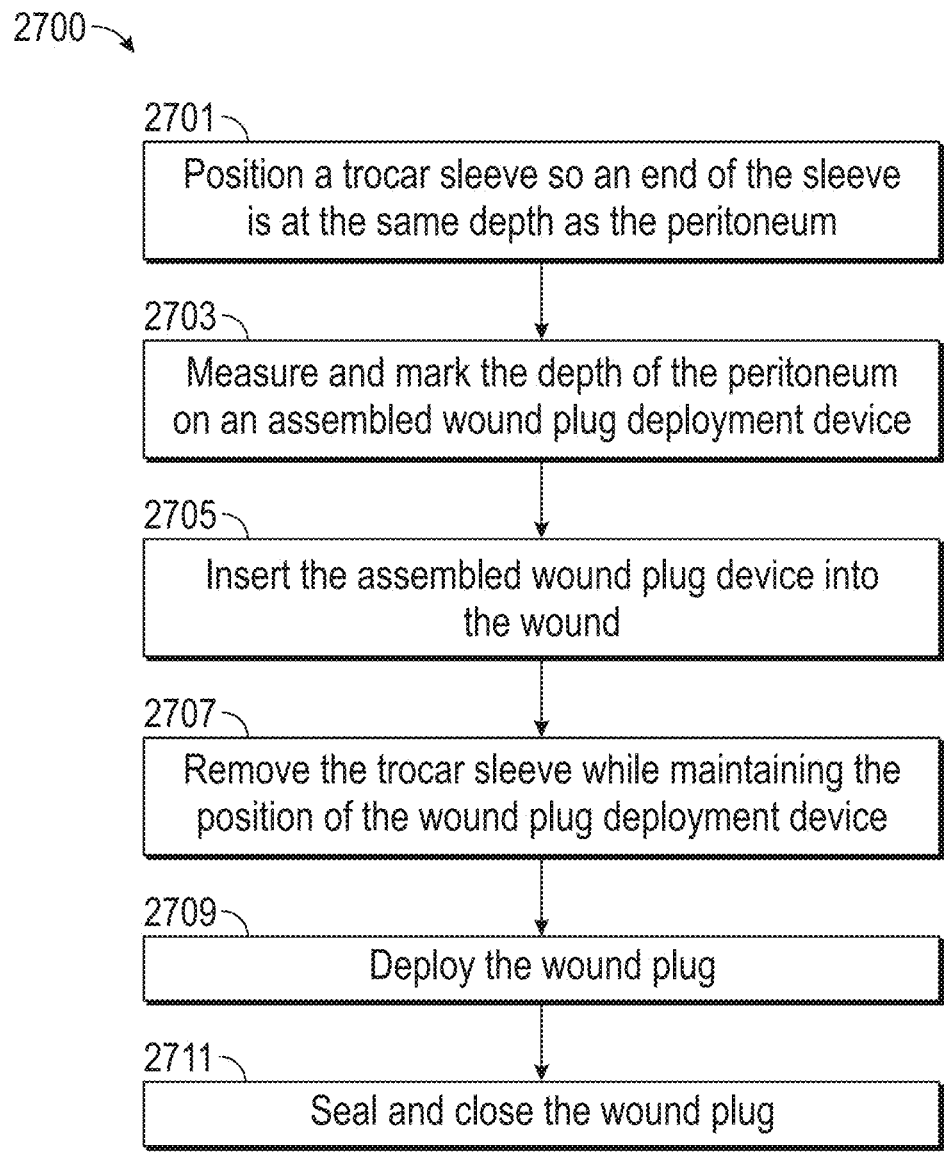
FIG. 27 illustrates is a flowchart of a method of implanting a wound plug according to embodiments of the disclosure.

FIGS. 26A-26C illustrate a hybrid wound plug implanted according to embodiments of the disclosure. FIG. 27 is a block diagram of a method 2700 for implanting a hybrid wound plug according to embodiments of the disclosure.

According to some embodiments, after surgery, a plurality of trocar sleeves e.g., 2681 may be left embedded in the abdomen 2678 of a patient. Each trocar sleeve is inserted in a wound in a patent that may be closed according to embodiments of the present disclosure. Accordingly, the doctor may have a plurality of wound plugs or assembled wound plug deployment devices corresponding to the number of wounds in the patient. The assembled device 2600 may include a hybrid wound plug 2630 and a cannulated post 2610 disposed therein. For example, the device 2600 may be assembled by inserting the cannulated post 2610 through the post receiving opening 2613 in the suprafascial rivet head 2604.

Prior to implanting a wound plug at a wound site, the doctor may determine a depth of the peritoneum at the wound site to know how far to advance the wound plug. In order to determine the depth of the peritoneum 2676, according to some embodiments of this disclosure, a user may pull the trocar sleeve 2681 from the wound and laparoscopically confirm that the tip of the trocar 2681 is at the same depth as the peritoneum 2676 (step 2701). The user may then remove the laparoscope (not shown) and any other lines, e.g., CO2. According to some examples, the length of the trocar sleeve 2681 may be known, as such, a physician may be able to determine the distance to the peritoneum based on the length of the trocar sleeve 2681 that is outside of the skin 2674.

Once the depth of the peritoneum is determined, the physician or medical professional may then measure and mark the depth of the peritoneum on an assembled wound plug deployment device 2600 (step 2703). Specifically, the physician may measure the depth from a first end of the assembled wound plug device 2600, e.g., from a distal end of the wound plug 2630, along the post 2610. The assembled wound plug implantation device 2600 may be then be inserted into the wound through the trocar 2681 (step 2705). The device should be advanced far enough through the trocar 2681 so that the second end of the wound plug 2630, i.e., the subfascial bladder, is out of the trocar 2681 and may expand. In embodiments, having a subfascial rivet head (not shown), the device may be advanced so that the extension cup may radially expand outside the trocar 2681 as shown in FIG. 26A.

The physician may then remove the trocar 2681 while keeping the non-deployed wound plug 2630 in place (step 2707). As seen in FIG. 26B, this may allow the extension cup 2623 of the suprafascial rivet head 2604 to radially expand over the anterior fascia 2677. In embodiments having a suprafascial bladder, the suprafascial bladder may expand over the wound over the anterior fascia 2677. In some embodiments, the depth of insertion of the wound plug may be monitored laparoscopically.

The wound plug 2630 may be deployed by filling the suprafascial rivet head 2604 and subfascial bladder 2647 with a liquefied matrix (step 2709). As the wound plug 3530 fills, the walls of the wound plug may expand and fill deadspace or voids in the wound such that the outer surface of the wound plug 2630 may abuts the tissue around the wound. In some embodiments, the surface of the wound plug may begin to adhere to tissue around the wound. The liquefied matrix may be injected at a first end of cannulated post through cannula 2628. The liquefied matrix may travel down the cannula 2628 and through the perforations 2627 into the wound plug 2630. In some embodiments, a syringe used to inject the liquefied matrix may be filled with a predetermined amount of liquefied matrix 2653 corresponding to the volume of the wound plug 2630. In some embodiments, the wound site of the wound plug may be monitored laparoscopically to determine the amount of liquefied matrix 2653 to fill the wound plug 2630. The liquefied matrix may be made from the same material as the wound plug and may include various additives, as described above.

Once the wound plug 2630, the post may be withdrawn from the wound and wound plug 2630, thereby closing and sealing the bladder (step 2711). In some embodiments, removing the post 2610 will aid in seating the subfascial bladder 2647 against the parietal peritoneum 2676. For example, in embodiments having a one-way valve or trap-door pulling the post from the wound plug may close the one-way valve and properly position the wound plug 2630. In embodiments having a suture, pulling the suture taut with the removal of the post may both seal the wound plug 2630 and abut the subfascial portion against the peritoneum. FIG. 26C illustrates a properly positioned wound plug according to embodiments of the present disclosure. Following deployment of the wound plug, the physician may close the incision at the skin 2674.

Although described here with respect to the external method, one skilled in the art will understand that the hybrid wound plug may be deployed according to the internal method described above. Additionally, although illustrated with respect to a wound plug having a suprafascial bladder and a subfascial rivet head, one skilled in the art will understand that this method may be applied to embodiments of a would plug having a suprafascial rivet head and a subfascial bladder.

In some embodiments, an apparatus for deploying a wound plug may include a post and a wound plug. The post may have a top end, a bottom end, and an interior channel located between the top end and the bottom end. The bottom end of the post may include a plurality of perforations extending from the interior channel to an outer surface of the post. The wound plug may include a body and a bladder, the bladder disposed around the body. In an assembled configuration of the apparatus, the bottom end of the post may be positioned through an opening of the bladder such that the bladder may receive a fluid through the interior channel and the plurality of perforations.

In some embodiments, a cross-section of a central portion of the bladder may have a smaller diameter than a cross-section near a top end of the wound plug and a smaller diameter than a cross-section near a bottom end of the wound plug. In some embodiments, the bladder may include a compressive band positioned around an outer perimeter of the bladder, wherein the compressive band causes a diameter of a central portion of the bladder to be smaller relative to a top portion and a bottom portion of the bladder. In some embodiments, the apparatus may include a suture, wherein a first end of the suture may be coupled to the bottom end of the post, and a second end of the suture may be stitched around the opening of the bladder. In some embodiments, the opening of the bladder may include at least one of: a one-way valve and a trap-door, such that the opening of the bladder is configured to receive the bottom end of the post.

In some embodiments, the body of the wound plug may include a top portion and a bottom portion. The top portion may have a first extended portion disposed at a top end of the wound plug and a plurality of first annular flanges that is circumferentially arranged around the top portion of the wound plug. The bottom portion may have a second extended portion disposed at a bottom end of the wound plug and a plurality of annular grooves arranged circumferentially around the bottom portion of the wound plug. The plurality of annular flanges and the plurality of annular grooves may be configured to interlock in a deployed configuration of the apparatus. According to some embodiments, the first extended portion and the second extended portion may have the same shape. In some embodiments, an outer diameter of the wound plug of the assembled apparatus is at least one selected from 5 mm, 8 mm, 10 mm, 12 mm, and 14 mm.

In some embodiments, an apparatus for deploying a wound plug, may include a post and a wound plug. The post may include a top end, a bottom end, and an interior channel located between the top end and the bottom end. The bottom end of the post may include a plurality of perforations extending from the interior channel to an outer surface of the post. The wound plug may include an opening, a bladder portion and a column portion. The opening may be configured to receive the bottom end of the post. The bladder portion may be configured to receive a fluid through the interior channel and plurality of perforations. The column portion may be coupled to the bladder portion.

In some embodiments, the bladder portion may include the opening configured to receive the bottom end of the post, such that the bladder portion is proximate to the post when the apparatus is in an assembled configuration. In some embodiments, the column portion may include the opening configured to receive the bottom end of the post, such that the column portion is proximate to the post in an assembled configuration of the apparatus. In some embodiments, the apparatus may include a suture, wherein a first end of the suture is coupled to the bottom end of the post, and a second end of the suture is stitched around the opening of the wound plug. In some embodiments, the opening of the wound plug may include at least one of: a one-way valve or a trap-door, such that the opening of the wound plug is configured to receive the bottom end of the post. In some embodiments, the column portion may include at least one of an extended portion and a plurality of barbs disposed on an outer circumference of the column portion.

In some embodiments, a wound plug may be deployed at a wound site. For example, in an assembled configuration of a wound plug apparatus, at least a bottom end of the wound plug apparatus may be inserted into a wound site, wherein the wound plug apparatus includes a post having a wound plug, wherein the wound plug is disposed on the post at the bottom end of the wound plug apparatus. A fluid may be injected into an internal channel disposed in the post, such that the fluid travels through the internal channel and into the wound plug. The post may be removed from the wound plug and the wound. In some embodiments, removing the post from the wound plug seals the wound plug from the wound site. In some embodiments, the injection of fluid expands the bladder of the wound plug laterally into the wound site. In some embodiments, an amount of the injected fluid is predetermined based on a size of the wound plug.

In some embodiments, the insertion of the wound plug apparatus may also include positioning a trocar sleeve disposed through the wound site, such that a tip of the trocar sleeve is proximate to the wound site. The trocar sleeve may be marked at a surface of the skin, such that the mark corresponds to a depth of the wound site. The trocar may then be removed from the wound site. A distance corresponding to the depth of the wound site may then be measured and marked on the wound plug apparatus.

In some embodiments, the insertion of the wound plug apparatus may also include inserting a wound plug apparatus into a first incision site. The wound plug apparatus may then be advanced from the first incision site to a wound site corresponding to a second incision, i.e., beneath a second incision on the skin surface. Proper positioning of the wound plug at the wound site may then be confirmed laparoscopically.

Although the disclosed examples have been fully described with reference to the accompanying drawings, it is to be noted that various changes and modifications will become apparent to those skilled in the art. For example, like numbers connote like features. Although some modifications may described with respect to particular examples, one skilled in the art will understand that the same modifications may be applied to other embodiments though not described with particularity. Such changes and modifications are to be understood as being included within the scope of the disclosed examples as defined by the appended claims.

The invention claimed is:

1. An apparatus for deploying a wound plug, the apparatus comprising:
    a post having a top end, a bottom end, and an interior channel located between the top end and the bottom end, wherein the bottom end of the post includes a plurality of perforations extending from the interior channel to an outer surface of the post; and
    a wound plug including a body and a bladder, the bladder disposed around the body of the wound plug,
    wherein in an assembled configuration of the apparatus, the bottom end of the post is positioned through an opening of the bladder such that the bladder can receive a fluid through the interior channel and the plurality of perforations.

2. The apparatus of claim 1, wherein a cross-section of a central portion of the bladder has a smaller diameter than a cross-section near a top end of the wound plug and smaller diameter than a cross-section near a bottom end of the wound plug.

3. The apparatus of claim 1, wherein the bladder includes a compressive band disposed around an outer perimeter of the bladder, wherein the compressive band causes a diameter of a central portion of the bladder to be smaller relative to a diameter of a top portion of the bladder and relative to diameter of a bottom portion of the bladder.

4. The apparatus of claim 1, further comprising a suture, wherein a first end of the suture is coupled to the bottom end of the post, and a second end of the suture is stitched around the opening of the bladder.

5. The apparatus of claim 1, wherein the opening of the bladder includes at least one of: a one-way valve and a trap-door, wherein the opening of the bladder is configured to receive the bottom end of the post.

6. The apparatus of claim 1, wherein the body of the wound plug includes:
    a top portion having a first extended portion disposed at a top end of the wound plug and a plurality of first annular flanges that is circumferentially arranged around the top portion of the wound plug; and a bottom portion having a second extended portion disposed at a bottom end of the wound plug and a plurality of annular grooves arranged circumferentially around the bottom portion of the wound plug, wherein the plurality of annular flanges and the plurality of annular grooves interlock in a deployed configuration of the apparatus.

7. The apparatus of claim 6, wherein the first extended portion and the second extended portion have the same shape.

8. The apparatus of claim 1, wherein an outer diameter of the wound plug of the apparatus when in the assembled configuration is at least one selected from: 5 mm, 8 mm, 10 mm, 12 mm, and 14 mm.

9. An apparatus for deploying a wound plug, the apparatus comprising:
 a post having a top end, a bottom end, and an interior channel located between the top end and the bottom end, wherein the bottom end of the post includes a plurality of perforations extending from the interior channel to an outer surface of the post;
 a wound plug including an opening configured to receive the bottom end of the post, the wound plug including:
  a bladder portion configured to receive a fluid through the interior channel and the plurality of perforations; and
  a column portion coupled to the bladder portion.

10. The apparatus of claim 9, wherein the bladder portion includes the opening configured to receive the bottom end of the post, such that the bladder portion is proximate to the post when the apparatus is in an assembled configuration.

11. The apparatus of claim 9, wherein the column portion includes the opening configured to receive the bottom end of the post, such that the column portion is proximate to the post when the apparatus is in an assembled configuration.

12. The apparatus of claim 9, further comprising a suture, wherein a first end of the suture is coupled to the bottom end of the post, and a second end of the suture is stitched around the opening of the wound plug.

13. The apparatus of claim 9, wherein the opening of the wound plug includes at least one of: a one-way valve and a trap-door, wherein the opening of the wound plug is configured to receive the bottom end of the post.

14. The apparatus of claim 9, wherein the column portion includes at least one of an extended portion and a plurality of barbs disposed on an outer circumference of the column portion.

* * * * *